US012590340B2

(12) United States Patent
Mahshid et al.

(10) Patent No.: US 12,590,340 B2
(45) Date of Patent: Mar. 31, 2026

(54) MICROFLUIDIC PLASMONIC COLOR READING CHIPS AND METHODS

(71) Applicant: THE ROYAL INSTITUTION FOR THE ADVANCEMENT OF LEARNING/MCGILL UNIVERSITY, Montreal (CA)

(72) Inventors: Sara Mahshid, Dollard-des-Ormeaux (CA); Mahsa Jalali, Montreal (CA); Tamer Abdelwahab, Montreal (CA); Carolina Del Real Mata, Montreal (CA)

(73) Assignee: THE ROYAL INSTITUTION FOR THE ADVANCEMENT OF LEARNING/MCGILL UNIVERSITY, Montreal (CA)

( * ) Notice: Subject to any disclaimer, the term of this patent is extended or adjusted under 35 U.S.C. 154(b) by 947 days.

(21) Appl. No.: 17/662,732

(22) Filed: May 10, 2022

(65) Prior Publication Data

US 2022/0372556 A1 Nov. 24, 2022

Related U.S. Application Data

(60) Provisional application No. 63/186,349, filed on May 10, 2021.

(51) Int. Cl.

| | |
|---|---|
| ***C12Q 1/689*** | (2018.01) |
| ***B01L 3/00*** | (2006.01) |
| ***C12Q 1/6844*** | (2018.01) |

(52) U.S. Cl.

CPC ........ *C12Q 1/689* (2013.01); *B01L 3/502753* (2013.01); *B01L 2200/16* (2013.01);

(Continued)

(58) Field of Classification Search

CPC . C12Q 1/689; C12Q 1/6844; B01L 3/502753; B01L 2200/16;

(Continued)

(56) References Cited

U.S. PATENT DOCUMENTS

| | | | | |
|---|---|---|---|---|
| 2004/0087033 | A1* | 5/2004 | Schembri .............. | B01L 3/5027 435/7.1 |
| 2019/0309346 | A1* | 10/2019 | Stakenborg ............ | C12Q 1/686 |
| 2022/0325363 | A1* | 10/2022 | Broughton .............. | B01L 7/525 |

OTHER PUBLICATIONS

Tamer AbdElSalam AbdElFatah AbdElWahab, "Integrated Microfluidic Device for Efficient Capture of Bacteria and Antimicrobial Susceptibility Testing", McGill University Department of Bioengineering, 2019.

* cited by examiner

*Primary Examiner* — Jennifer Wecker
*Assistant Examiner* — Britney N. Washington
(74) *Attorney, Agent, or Firm* — Norton Rose Fulbright Canada LLP

(57) ABSTRACT

There is provided a microfluidic chip for sensing an analyte in a sample by colorimetry. The microfluidic chip comprises: an inlet adapted to receive the sample; an incubation chamber having an incubation chamber inlet fluidly connected to the inlet downstream thereof, to incubate the analyte in the sample; a filter barrier fluidly connected to the incubation chamber, downstream of the incubation chamber inlet; a sensing chamber fluidly connected to the incubation chamber, downstream of the filter barrier, the sensing chamber having a plasmonic nanosurface, the plasmonic nanosurface including nanostructures protruding from the plasmonic nanosurface, the nanostructures having a size that is smaller than that of the diffraction limit of light, the nanostructures having a metallic layer that is plasmon-supported on top of (Continued)

a back reflector layer; and an outlet fluidly connected to the sensing chamber downstream thereof.

20 Claims, 61 Drawing Sheets

Specification includes a Sequence Listing.

(52) U.S. Cl.
CPC .................. *B01L 2300/0681* (2013.01); *B01L 2300/0883* (2013.01); *B01L 2300/1805* (2013.01); *C12Q 1/6844* (2013.01)

(58) Field of Classification Search
CPC ..... B01L 2300/0681; B01L 2300/0883; B01L 2300/1805; B01L 2200/10; B01L 2300/0816; B01L 2300/0896; B01L 2300/168; B01L 2300/1827; B01L 2400/086; B01L 3/5027; G01N 21/25; G01N 2021/258
See application file for complete search history.

D= 200 nm

D= 400 nm

D= 600 nm

D= 750 nm

D= 1000 nm

Methicilin-resistant *S. Aureus* Colorimetric Signal Change at 0.2 ng/μL

*P.Aeruginosa* Colorimetric Signal Change at 0.2 ng/μL

Amplex Red

Resorufin

SEQUENCE LISTING

<160> NUMBER OF SEQ ID NOS: 18

<210> SEQ ID NO 1
<211> LENGTH: 18
<212> TYPE: DNA
<213> ORGANISM: Artificial Sequence
<220> FEATURE:
<223> OTHER INFORMATION: E coli primer F3

<400> SEQUENCE: 1
gccatctcct gatgacgc 18

<210> SEQ ID NO 2
<211> LENGTH: 18
<212> TYPE: DNA
<213> ORGANISM: Artificial Sequence
<220> FEATURE:
<223> OTHER INFORMATION: E coli primer B3

<400> SEQUENCE: 2
atttaccgca gccagacg 18

<210> SEQ ID NO 3
<211> LENGTH: 42
<212> TYPE: DNA
<213> ORGANISM: Artificial Sequence
<220> FEATURE:
<223> OTHER INFORMATION: E coli primer FIP

<400> SEQUENCE: 3
cattttgcag ctgtacgctc gcagcccatc atgaatgttg ct 42

<210> SEQ ID NO 4
<211> LENGTH: 40
<212> TYPE: DNA
<213> ORGANISM: Artificial Sequence
<220> FEATURE:
<223> OTHER INFORMATION: E coli primer BIP

<400> SEQUENCE: 4
ctggggcgag gtcgtggtat tccgacaaac accacgaatt 40

<210> SEQ ID NO 5
<211> LENGTH: 24
<212> TYPE: DNA
<213> ORGANISM: Artificial Sequence
<220> FEATURE:
<223> OTHER INFORMATION: E coli primer LF

<400> SEQUENCE: 5
ctttgtaaca acctgtcatc gaca 24

<210> SEQ ID NO 6
<211> LENGTH: 25
<212> TYPE: DNA
<213> ORGANISM: Artificial Sequence
<220> FEATURE:
<223> OTHER INFORMATION: E coli primer LB

<400> SEQUENCE: 6

-continued atcaatctcg atatccatga aggtg 25

<210> SEQ ID NO 7
<211> LENGTH: 18
<212> TYPE: DNA
<213> ORGANISM: Artificial Sequence
<220> FEATURE:
<223> OTHER INFORMATION: Methicillin resistant S aureus primer F3

<400> SEQUENCE: 7
ggctcaggta ctgctatc 18

<210> SEQ ID NO 8
<211> LENGTH: 23
<212> TYPE: DNA
<213> ORGANISM: Artificial Sequence
<220> FEATURE:
<223> OTHER INFORMATION: Methicillin resistant S aureus primer B3

<400> SEQUENCE: 8
ttgttattta acccaatcat tgc 23

<210> SEQ ID NO 9
<211> LENGTH: 49
<212> TYPE: DNA
<213> ORGANISM: Artificial Sequence
<220> FEATURE:
<223> OTHER INFORMATION: Methicillin resistant S aureus primer FIP

<400> SEQUENCE: 9
atgccataca taaatggata gacgtcaaac aggtgaatta ttagcactt 49

<210> SEQ ID NO 10
<211> LENGTH: 45
<212> TYPE: DNA
<213> ORGANISM: Artificial Sequence
<220> FEATURE:
<223> OTHER INFORMATION: Methicillin resistant S aureus primer BIP

<400> SEQUENCE: 10
ccgaagataa aaaagaacct ctgctttttt gagttgaacc tggtg 45

<210> SEQ ID NO 11
<211> LENGTH: 19
<212> TYPE: DNA
<213> ORGANISM: Artificial Sequence
<220> FEATURE:
<223> OTHER INFORMATION: Methicillin resistant S aureus primer LF

<400> SEQUENCE: 11
catatgaagg tgtgcttac 19

<210> SEQ ID NO 12
<211> LENGTH: 20
<212> TYPE: DNA
<213> ORGANISM: Artificial Sequence
<220> FEATURE:
<223> OTHER INFORMATION: Methicillin resistant S aureus primer LB

<400> SEQUENCE: 12
caagttccag attacaactt 20

<210> SEQ ID NO 13
<211> LENGTH: 18
<212> TYPE: DNA

-continued

<213> ORGANISM: Artificial Sequence
<220> FEATURE:
<223> OTHER INFORMATION: P aeruginosa primer F3

<400> SEQUENCE: 13
gcgttgccgc caacaatg 18

<210> SEQ ID NO 14
<211> LENGTH: 17
<212> TYPE: DNA
<213> ORGANISM: Artificial Sequence
<220> FEATURE:
<223> OTHER INFORMATION: P aeruginosa primer B3

<400> SEQUENCE: 14
catgcgggca acctctc 17

<210> SEQ ID NO 15
<211> LENGTH: 35
<212> TYPE: DNA
<213> ORGANISM: Artificial Sequence
<220> FEATURE:
<223> OTHER INFORMATION: P aeruginosa primer FIP

<400> SEQUENCE: 15
gttgtcaccc cacctccggg cggcaacgtt cctcc 35

<210> SEQ ID NO 16
<211> LENGTH: 34
<212> TYPE: DNA
<213> ORGANISM: Artificial Sequence
<220> FEATURE:
<223> OTHER INFORMATION: P aeruginosa primer BIP

<400> SEQUENCE: 16
ctccgtgcag ggcgaactgc aggcgagcca actc 34

<210> SEQ ID NO 17
<211> LENGTH: 17
<212> TYPE: DNA
<213> ORGANISM: Artificial Sequence
<220> FEATURE:
<223> OTHER INFORMATION: P aeruginosa primer LF

<400> SEQUENCE: 17
acctgccgtg ccatacc 17

<210> SEQ ID NO 18
<211> LENGTH: 19
<212> TYPE: DNA
<213> ORGANISM: Artificial Sequence
<220> FEATURE:
<223> OTHER INFORMATION: P aeruginosa primer LB

<400> SEQUENCE: 18
gttcatgcag ctccagcag 19

MICROFLUIDIC PLASMONIC COLOR READING CHIPS AND METHODS

CROSS-REFERENCE TO RELATED APPLICATIONS

This present patent application claims priority to U.S. Provisional Patent Application No. 63/186,349 filed on May 10, 2021, the entire content of which is incorporated herein by reference.

TECHNICAL FIELD

This disclosure generally relates to the field of microfluidic colorimetric sensing chips, methods of fabricating same, and methods of detection using same.

BACKGROUND OF THE ART

Colorimetric assays may be used at the point of need because they offer many key advantages such as ease of operation, ability to implement in low resource settings, and reduced requirements for expensive reagents. Examples of colorimetric assays include nucleic acid amplification assays. Nucleic acid amplification can be used, for example, in the genotypic detection of pathogens. Another example of a colorimetric assay at the point of need is a bacterial culture test to determine whether a patient is infected with an antibiotic resistant bacteria. Generally, clinicians may either make rapid decisions on empirical antibiotic treatment of infectious syndromes without knowing whether causative pathogen(s) are drug-susceptible or drug-resistant or hold for at least 48 hours to receive the results of susceptibility from conventional clinical approaches. Using traditional approaches, it may take about 24 hours for procuring growth of clinical specimens, followed by an additional 24 hours for down-stream isolate characterization such as biochemical identification, and phenotypic susceptibility testing. There remains improvements in colorimetric assays at least to alleviate such drawbacks and/or achieve sensitive and rapid testing.

SUMMARY

In a first aspect, there is provided a microfluidic chip for sensing an analyte in a sample by colorimetry, the microfluidic chip includes: an inlet adapted to receive the sample; an incubation chamber having an incubation chamber inlet fluidly connected to the inlet downstream thereof, to incubate the analyte in the sample; a filter barrier fluidly connected to the incubation chamber, downstream of the incubation chamber inlet; a sensing chamber fluidly connected to the incubation chamber, downstream of the filter barrier, the sensing chamber having a plasmonic nanosurface, the plasmonic nanosurface including nanostructures protruding from the plasmonic nanosurface, the nanostructures having a size that is smaller than that of the diffraction limit of light, the nanostructures having a metallic layer that is plasmon-supported on top of a back reflector layer; and an outlet fluidly connected to the sensing chamber downstream thereof.

In a second aspect, there is provided a method of sensing an analyte in a sample including: providing a microfluidic chip as defined in the present disclosure; providing the sample at the inlet; incubating the sample in the incubation chamber for a predetermined period of time; flowing the sample across the filter barrier to the sensing chamber; and analyzing a plasmonic color change of the sample.

In a third aspect, there is provided a method of fabricating a microfluidic chip comprising: providing a base layer coated with a negative photoresist; patterning the chip using a mask that delineates an inlet, an incubation chamber, a barrier, a sensing chamber, an outlet and microchannels in between; creating a self-assembling monolayer of nanoparticles on a surface of the sensing chamber; coating the nanoparticles with a back reflector and with a plasmon-supported metal; and sealing the fabless microfluidic chip.

Further in accordance with the third aspect, for instance, sealing the microfluidic chip including curing a transparent polymer to seal the microfluidic chip.

Many further features and combinations thereof concerning the present improvements will appear to those skilled in the art following a reading of the instant disclosure.

DETAILED DESCRIPTION

Figure 1A:
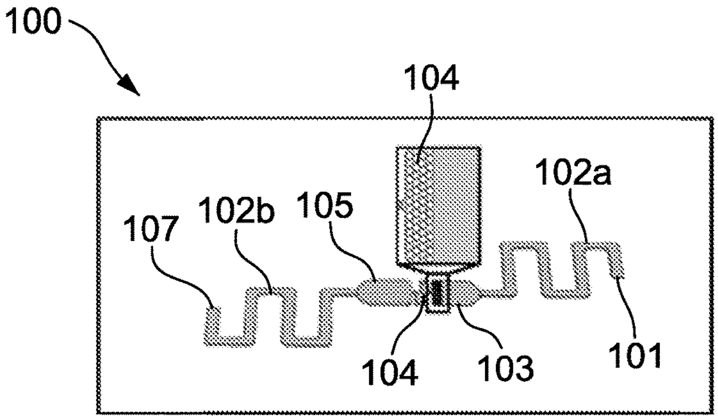
FIG. 1A is a schematic top view of a microfluidic chip according to an embodiment.

There is provided microfluidic chips to perform rapid and sensitive testing of analytes by colorimetry. A multitude of analytes can be detected with the microfluidic chips disclosed herein, as long as there is a colorimetric sensor corresponding to the analyte. For instance, as will be described later, the microfluidic chips may be used for detection of antibiotic resistant bacteria, genotypic detection of pathogens, detection of nucleic acid sequences by nucleic acid amplification (e.g. polymerase chain reaction (PCR), reverse transcription loop-mediated isothermal amplification (RT-LAMP) or a rolling circle amplification (RCA)), and sensing of cancerous cells.

The microfluidic chips integrate plasmonic meta-surfaces with fluidic sample delivery to directly monitor the conversion of a colorimetric assay. Expensive instrumentation and highly skilled operators may therefore not be required to utilize the microfluidic chips of the present disclosure. The microfluidic chips may not require dedicated external fluid actuation facilities such as syringe pumps or pressurized pneumatic lines. It may allow high-throughput, highly parallel, rapid and quantitative measurements, making the disclosed chips a point of need approach for assessing drug resistance profiles and monitoring metabolic reactions, for example. Furthermore, the reduced volume compared to non-microfluidic colorimetric assays may allow for a rapid run time with high sensitivity. The lower volume may further advantageously reduce the required amounts of reagents thereby reducing assay costs. As will be described in further details herein below, a high sensitivity may be achieved by using plasmonic platforms/surfaces to facilitate the rapid detection of a change in color of the colorimetric sensor.

Microfluidic chips as generally presented above will now be described according to various embodiments. The microfluidic chips may receive and/or contain a sample to be tested. Exemplary tests, samples and applications involving the microfluidic chips will also be described.

Samples may include a colorimetric sensor. For example, a sample and a colorimetric sensor can be provided in the same inlet of the microfluidic chip. In another example, the sample and the colorimetric sensor are mixed to obtain a mixture of the sample and the colorimetric sensor and then that mixture is provided at an inlet of the microfluidic chip. Alternatively, the colorimetric sensor may be provided in an inlet separate from another inlet in which the sample is provided. In such embodiments, the colorimetric sensor may mix with the sample within the microchannels of the microfluidic chip. The colorimetric sensor may be any appropriate colorimetric sensor that is specific to an analyte of interest so that the colorimetric sensor changes the color of the sample if the analyte is present. The colorimetric sensor may be a salt that reacts with a metabolic enzyme such as the NADH/NADPH cellular oxidoreductase enzymes. Examples of such salts include resazurin (metabolized to resorufin) and tetrazolium salts that are metabolized to formazan due to the disruption of the tetrazole ring. The tetrazolium salt can be selected from the group consisting of MTT (3-(4,5-dimethyl-thiazol-2-yl)-2,5-diphenyltetrazolium bromide), XTT (2,3-bis-(2-methoxy-4-nitro-5-sulfophenyl)-2H-tetrazolium-5-carboxanilide inner salt), MTS (3-(4,5-dimethylthiazol-2-yl)-5-(3-carboxymethylphenyl)-2-(4-sulfophenyl)-2H-tetrazolium), and WST (water-soluble tetrazolium salts). The colorimetric sensor may be a 3,3',5,5'-Tetramethylbenzidine or TMB which is a chromogenic substrate that can used in staining procedures in immunohistochemistry as well as a visualizing reagent exploited in enzyme-linked immunosorbent assays (ELISA). TMB is a white solid that forms a pale blue-green liquid in solution with ethyl acetate. The colorimetric sensor may be a pH sensitive dye in the fluid media that changes color when the pH changes. For example the colorimetric sensor may be phenol red, methyl blue, bromothymol blue, p-nitrophenol (formed by alkaline phosphatase from p-nitrophenol phosphate) and other similar colorimetric acid-base indicators. The colorimetric sensor can also be a $H_2O_2$ sensitive media that changes color with the concentration of $H_2O_2$ such as iodide or titanium based $H_2O_2$ indicators and the Amplex® Red reagent which reacts with $H_2O_2$ to produce the red-fluorescent oxidation product, resorufin. In addition, color-sensitive nanoparticles may be used, including Au, Ag, AuPd and other nanoparticles possessing colors in the range of red to the blue.

Figure 1B:
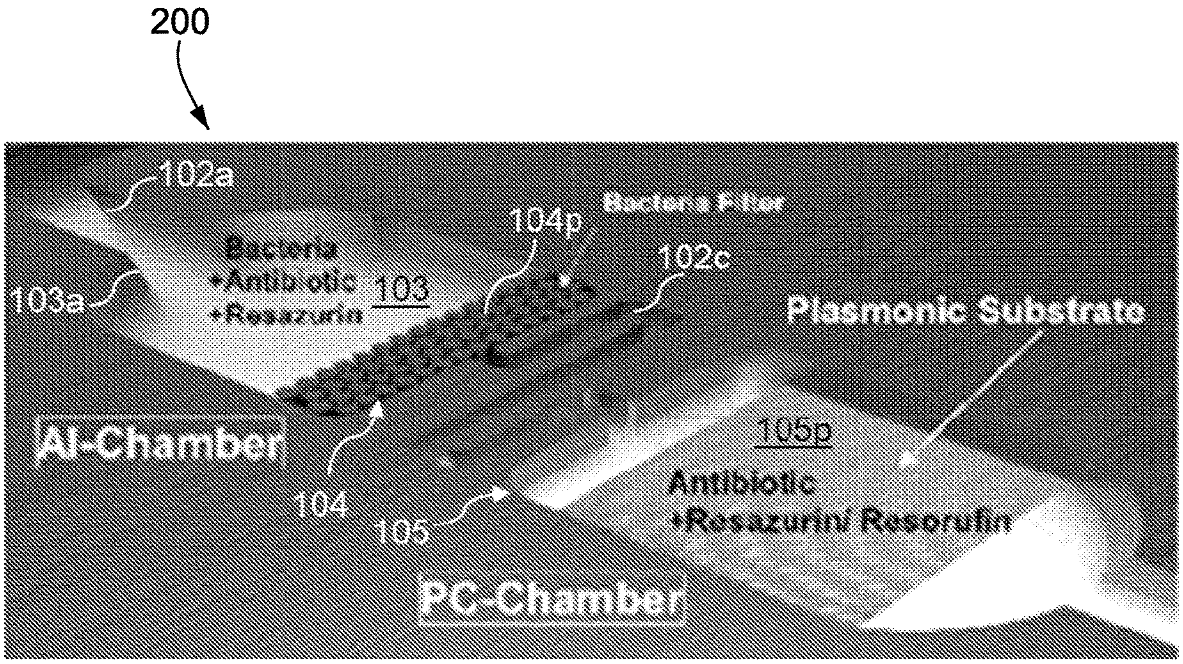
FIG. 1B is a schematic side elevation view of the microfluidic chip of FIG. 1A.

FIGS. 1A-1B illustrate a microfluidic chip 100 according to an embodiment of the present disclosure. The microfluidic chip 100 has an inlet 101 adapted to receive a sample, such as the exemplary samples discussed above. An inlet microchannel 102*a* is defined between the inlet 101 and an incubation chamber 103. The inlet microchannel 102*a* fluidly connects to an incubation chamber inlet 103*a*. The incubation chamber inlet 103*a* may be defined at a junction between the inlet microchannel 102*a* and the widening portion of the chamber 103. In the embodiment shown, the microfluidic chip 100 has a single inlet microchannel 102*a*. A plurality of inlet microchannels 102*a* may be contemplated in other embodiments. The microchannel 102*a* may be shaped so as to promote mixing in the flowing sample upstream of the incubation chamber 103. As shown, in some embodiments, the microchannel 102*a* has a serpentine shape. The microchannel 102*a* may include a plurality of hairpin bends. The number of hairpin bends may vary depending on the embodiments. The number of hairpin bends may be selected so as to obtain a desired level of mixing. In at least some embodiments, there is at least three hairpin bends. There may be between two and twelve hairpin bends in some embodiments. There could be more in other embodiments. The microchannel(s) 102*a* may have other shape/geometry adapted to promote mixing in the flowing sample. The microchannel 102*a* may have a uniform cross-section or a variable cross-section. For example, the microchannel 102*a* may define one or more mixing chambers or widening section(s) and/or bottleneck section(s) there along. This may create turbulence within the flowing sample, by a change in geometry or pressure differential within the flowing sample, which may promote mixing. The microchannel(s) 102*a* may be linear (straight) in other embodiments, with or without such mixing chambers and/or sections. The microchannel 102*a* may have a cross-sectional shape(s) and size(s) selected based on an inlet pressure required to deliver the sample. The inlet pressure may be such that the sample may flow across the microfluidic chip 100 at a flow rate that would not hinder the sensitivity of the assay when the sample flows into and through a sensor chamber 105 (described later) downstream of the incubation chamber 103.

In one embodiment, the inlet microchannel 102*a* is embedded within a filter paper. In instances where the sample is a blood sample, such a filter paper may pre-filter the blood sample to remove at least part of the impurities in the blood sample before the sample reaches the incubation chamber 103. The filter paper is only one possibility. Other pre-filtering features/techniques may be contemplated such as straining or centrifuging the sample before providing the sample to the inlet 101.

The incubation chamber 103 may receive/contain the mixed (or unmixed) sample. When the sample is contained in the incubation chamber 103 with the colorimetric sensor, the sample may be subjected to conditions that promote the colorimetric reaction to change the color of the sample. For example, heating may be applied.

As shown, a barrier 104, which may also be referred to as a barrier filter, is located downstream of the incubation chamber inlet 103*a*. The barrier 104 may restrict the flow (e.g., reduce the flow rate) from exiting the incubation chamber 103. In the embodiment shown, the incubation chamber 103 includes the barrier 104. After incubation, the sample may be pushed (e.g., by pressure differential) through the barrier 104 and into the sensing chamber 105. The barrier 104 may occupy a portion of the incubation chamber 103. The proportion of the incubation chamber 103 occupied by the barrier 104 may vary depending on the embodiments. In some embodiments, the barrier 104 may take up less than 50% of a total volume of the incubation chamber 103. Other proportions, i.e., between 50% and 70% could also be contemplated. The sample may be substantially or entirely retained in the incubation chamber 103 thanks to the barrier 104. In this context, the term “substantially” may be defined as having at least 80%, at least 85%, at least 90%, at least 95% or at least 99% of the volume of the sample being retained in the incubation chamber 103 for an incubation period. The barrier 104 may be enclosed within the incubation chamber 103 in a downstreammost portion of the incubation chamber 103, as can be seen in FIG. 1B. This is only one possibility. The barrier 104 may be located downstream of the incubation chamber 103, such as in a separate “filter chamber” fluidly connected to the incubation chamber 103 downstream thereof as another example.

The barrier 104 may entrap debris, undesirable particles, cells, such as bacteria, or other microscopic bodies before the flowing sample reaches the sensing chamber 105. In at least some embodiments, the barrier 104 includes an array of protruding microstructures 104*p*. In an embodiment, the protruding microstructures 104*p* are substantially cylindrical in shape (such as micropillars), however other shapes may be contemplated. The protruding microstructures 104*p* are spaced apart to define a minimal distance between two protruding microstructure 104*p* or between a protruding microstructure 104*p* and a wall of the incubation chamber 103. The protruding microstructures 104*p* may all have substantially the same size or there can be a variation in the size between the different protruding microstructures 104*p*. The protruding microstructures can be arranged such that a flow of sample across the barrier 104 has to go through at least one minimal distance. This minimal distance can be referred to as the filter pore size. The minimal distance may be a range of values as the distance between two protruding microstructures 104*p* may not be exactly constant. Solid particles, organisms or molecules that are larger than the minimal distance may not go through the barrier 104 and may thus be entrapped in the incubation chamber 103. For simplicity, the minimal distance between protruding microstructures 104*p* of the barrier 104 will be referred to herein as the pore size of the barrier 104 filter. The pore size can be in the nanoscale range and can prevent the passage of bacteria and certain viruses, molecules and/or polymers. In some embodiments, the pore size is less than 1000 nm, less than 900 nm, less than 800 nm, less than 700 nm, less than 600 nm, less than 500 nm, less than 400 nm, between 100 nm and 1000 nm, between 200 and 900 nm, between 200 and 800 nm, between 200 and 700 nm, between 200 and 600 nm, between 200 and 500 nm or between 200 and 400 nm. In some embodiments, the protruding microstructures 104*p* have a size of from 5 to 50 μm or from 5 to 40 μm. For example, the protruding microstructures 104*p* can be micropillars having a diameter from 5 to 50 μm or from 5 to 40 μm. The spacing between the micropillars is preferably sufficiently large so as to allow a substantially laminar flow of the sample across the barrier 104. In some embodiments, the barrier 104 comprises at least two rows of protruding microstructures 104*p* spaced apart so as to define a minimal distance being the pore size as described above. In some embodiments, the barrier 104 can comprise at least 3, at least 4, at least 5, at least 6, from 2 to 20, from 2 to 15, or from 2 to 10 of rows of protruding microstructure 104*p*.

As shown in FIG. 1B, the incubation channel 103 and the sensing chamber 105 are fluidly connected via a microchannel 102*c*. As shown, the microchannel 102*c* extends between the incubation chamber 103 and the sensing chamber 105. In the embodiment shown, the microchannel 102*c* has a serpentine shape, which may further promote mixing of the filtered sample once it flowed through the barrier 104. There may be more microchannels 102*c* fluidly connecting the chambers 103, 105 in other embodiments, and/or microchannel 102*c* may have other shapes, similar to the inlet microchannel 102*a* discussed above, for example. Returning to FIG. 1A, downstream of the sensing chamber 105 is an outlet microchannel 102*b*. The outlet microchannel 102*b* is shown as a single serpentine channel 102*b*. Other shapes/geometry may be contemplated. The outlet microchannel 102*b* may channel the sample out of the chip 100 through outlet 107. The sample may be drained through the outlet 107. A plurality of outlet microchannels 102*b* fluidly connected to the sensing chamber 105 downstream thereof may be contemplated. More than one outlet 107 may also be contemplated in other embodiments.

As shown in FIG. 1B, the sensing chamber 105 has a plasmonic nanosurface 105*p*, which may be referred to as plasmonic substrate, to allow increased sensitivity to the change in color of the colorimetric sensor. The color-generation strategy of plasmonic color printing involves the patterning of various geometrical metallic nanostructures. The nanostructures have a size that is smaller than that of the diffraction limit of light. The nanostructures and materials thereof are designed to resonate at a specific optical frequency leading to the production of different colors across the visible spectrum. The nanostructures act as nanoantennas when exposed to an electromagnetic field of light that resonate to increase a color gamut between the changes in color of the colorimetric sensor.

Figure 2A:
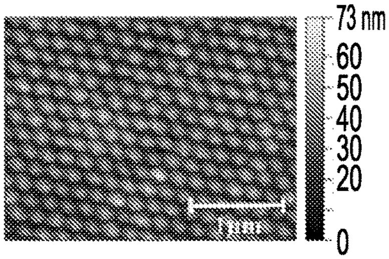
FIG. 2A is a microscopy image acquired by tapping mode atomic force microscopy (AFM) performed to characterize the morphology of different plasmonic platforms of silicon pieces a self-assembled monolayer (SAM) of nanoparticles of 200 nm.
Figure 2B:
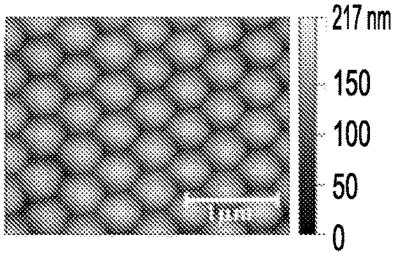
FIG. 2B is a microscopy image acquired by tapping mode AFM performed to characterize the morphology of different plasmonic platforms of silicon pieces a SAM of nanoparticles of 400 nm.
Figure 2C:
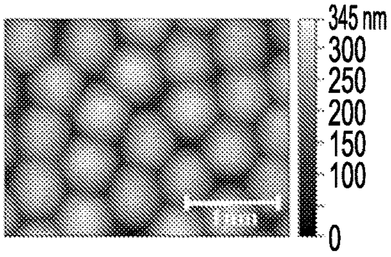
FIG. 2C is a microscopy image acquired by tapping mode AFM performed to characterize the morphology of different plasmonic platforms of silicon pieces a SAM of nanoparticles of 600 nm.
Figure 2D:
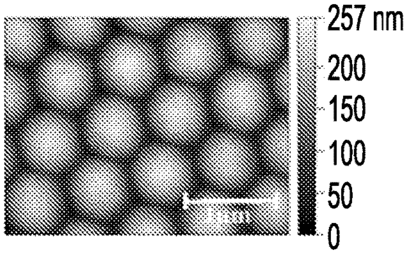
FIG. 2D is a microscopy image acquired by tapping mode AFM performed to characterize the morphology of different plasmonic platforms of silicon pieces a SAM of nanoparticles of 750 nm.
Figure 2E:
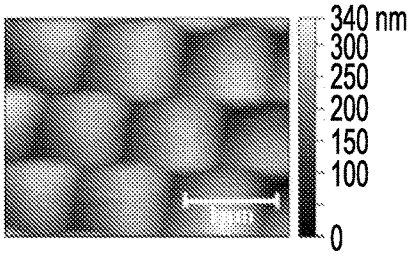
FIG. 2E is a microscopy image acquired by tapping mode AFM performed to characterize the morphology of different plasmonic platforms of silicon pieces a SAM of nanoparticles of 1000 nm.
Figure 2F:
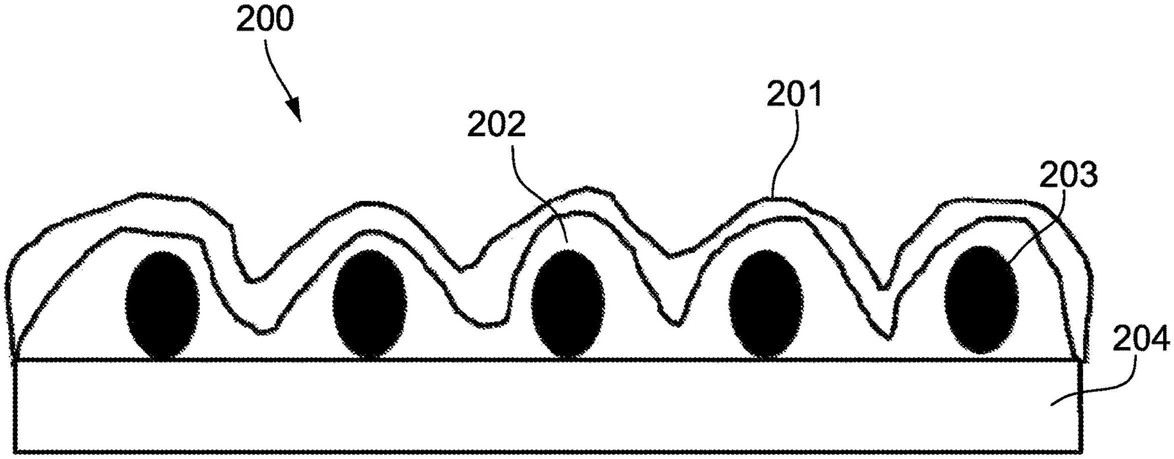
FIG. 2F is a schematic cross section view of nanostructures according to one embodiment.

The nanostructures protrude from the nanosurface 105*p*. The nanostructures may be in the shape of nanodisks, ellipses, nanocubes and/or multimers. In one embodiment, the nanostructures may have a diameter between 200 nm and 1000 nm. Examples of nanostructures are shown in FIGS. 2A-2E. FIGS. 2A, 2B, 2C, 2D and 2E show tapping mode atomic force microscopy (AFM) images of nanostructures obtained by a self-assembled monolayer (SAM) of nanoparticles having a diameter of 200, 400, 600, 750, and 1000 nm respectively. The interparticle gap spacing (gap between adjacent protruding nanostructures) can be considered to act as a plasmonic nanocavity. The interparticle gap length in FIGS. 2A-2E vary from 20 nm to 500 nm (±5 nm or ±5%) or 73 nm and 340 nm (±5 nm or ±5%) with increasing nanostructures diameter (or maximum transverse dimension if diameter does not apply). With decreasing color change in the assay, smaller gaps (below 200 nm) generate more enhanced electromagnetic field. In a least some embodiments, as illustrated in FIG. 2F, the nanostructures 200 have a plasmon-supported metallic layer 201 with the ability to provide tunable localized surface plasmon resonance. The plasmon-supported metallic layer 201 may provide high-resolution plasmonic color with a white background. For example, the plasmon-supported metallic 201 surface is one of gold, silver, and aluminum or alloys thereof such as AuAg, AuAl, and AgAl. The plasmon-supported metallic layer 201 may also be a bimetallic of Au, Ag, and Al such as AuPd, AgPd, AuNi, AuCu, AgCu, AuNiCu. In at least some embodiments the plasmon-supported metallic layer 201 is a layer of 5 nm to 100 nm, 10 to 50 nm, 15 to 25 nm or 10 to 25 nm. Under the plasmon-supported metallic layer 201 the nanostructures 200 may have a back reflector layer 202. In some embodiments, the back reflector layer 202 has a thickness from 10 nm to 400 nm, 50 nm to 130 nm or from 60 nm to 120 nm. The back reflector layer 202 covers nanoparticles 203 that are deposited on the surface 204 of the sensing chamber 105. The back reflector material may advantageously be deposited using sputtering, ebeam deposition and/or spin coating. In one embodiment the back reflector layer 202 comprises or consists of one of ZnO, $TiO_2$, hydrogen silsesquioxane (HSQ), AZ MiR™, or polymethyl methacrylate (PMMA). In one example the nanoparticles are made of polystyrene and have a diameter of between 200 to 1000 nm. The nanoparticles may be in any suitable shape, preferably a spheroidal shape such as a sphere. Unlike organic-dye color filters, the plasmonic color filters may offer advantages such as high color tunability, sensitive color changing based on medium permittivity and low color degradation rate.

Figure 3A:
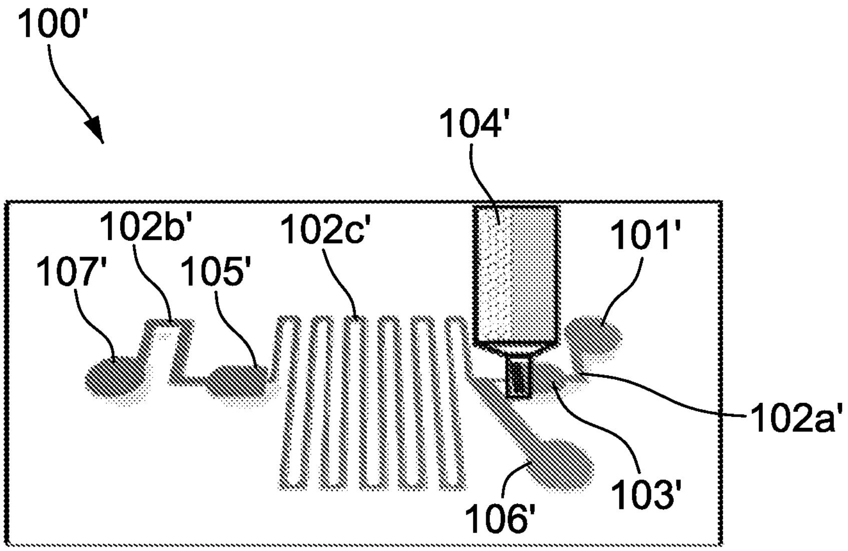
FIG. 3A is a schematic top view of a microfluidic chip according to an embodiment.
Figure 3B:
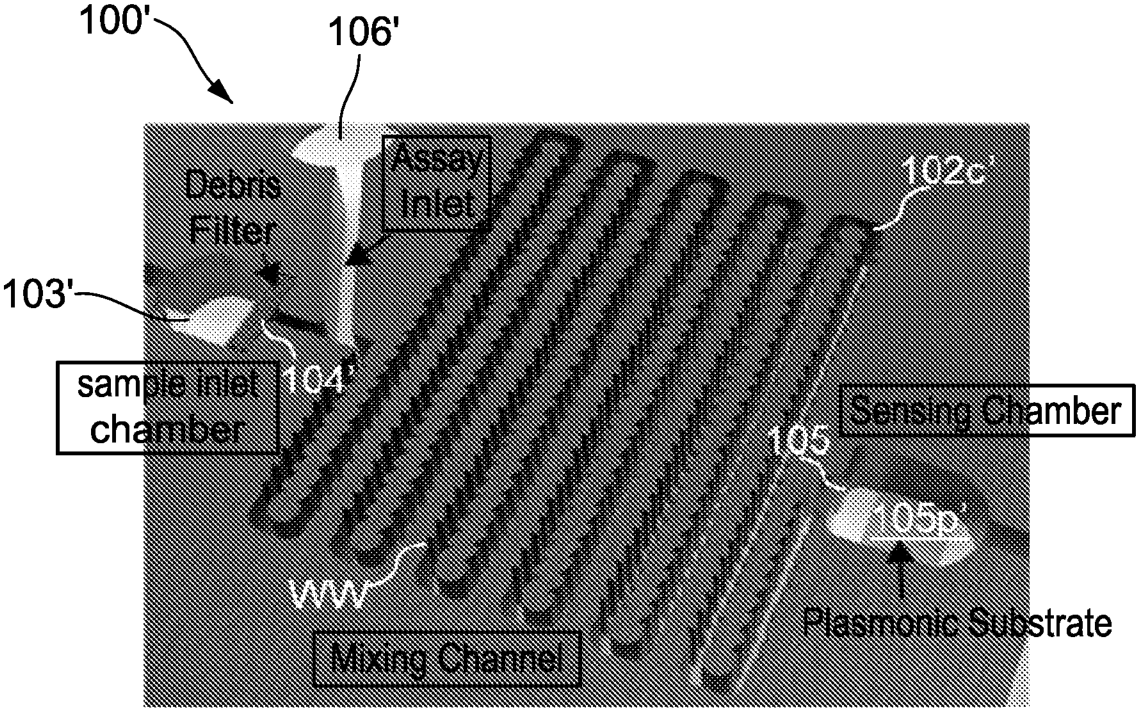
FIG. 3B is a schematic side elevation view of the microfluidic chip of FIG. 3A.

Referring to FIGS. 3A-3B, a variant of the chip 100 of FIGS. 1A-1B will be presented. Like features bear the same reference number for ease of reference, with prime added. Characteristics of the features described with respect to the chip 100 may similarly apply to chip 100' of FIGS. 3A-3B, hence they will not be repeated in whole for conciseness. For example, in FIGS. 3A-3B, the barrier 104' is enclosed in the incubation chamber 103' and occupies a portion of the total volume thereof. This is given as an example.

As illustrated in FIGS. 3A and 3B, the colorimetric sensor may be added within the sample downstream of the inlet 101', inlet microchannel 102*a*' and incubation chamber 103'. In the variant shown, the microfluidic chip 100' includes a second inlet 106'. The second inlet 106' is located downstream of the incubation chamber 103'. The second inlet 106' may be adapted to receive the colorimetric sensor. The second inlet 106' may also be used to provide other reagents into the flowing sample, such as, without limitation, nucleic acids, primers, enzymes, buffers, salts. In embodiments where the colorimetric sensor is provided after the sample has gone through the incubation chamber 103, i.e., downstream of the incubation chamber 103', it may be desirable to perform further mixing of the sample before it reaches the sensing chamber 105'. As shown, a microchannel 102*c*' fluidly interconnects the incubation chamber 103' and inlet 106', at an upstream end of the microchannel 102*c*', and the sensing chamber 105' at a downstream end of the microchannel 102*c'*

The microchannel 102*c*' defines a mixing zone between the incubation chamber 103' and the sensing chamber 105' adapted to provide sufficient mixing of the sample with the colorimetric sensor and sufficient time for the colorimetric reaction to occur at a predetermined flow rate. As it is being mixed, the flowing sample may change color before reaching the sensing chamber 105'. The mixing zone, also referred to as mixing channel, may be a serpentine or any other suitable shape as described above, for example with or without mixing sub-chambers, one or more microchannels 102*c*', etc. As can be seen in the magnified view of FIG. 3B, in an embodiment, the walls of the microchannel 102*c*' have an outline adapted to promote mixing. Mixing may be performed by creating a turbulent flow. In an embodiment, such as shown, the side walls WW of the microchannel 102*c*' have a toothed outline. The toothed outline may define a series of arrows or serially distributed triangularly shaped sections. Other outlines may be contemplated, such as an outline defining discontinuities, bends, waves, or irregular patterns, for example. As another mixing parameter, surface roughness of the walls WW may also contribute to the mixing. Other configurations may be contemplated. While such toothed outline is described with reference to microchannel 102*c*', it should be understood that any one of the microchannels (102*a*, 102*b*, 102*c*, 102*a*' and 102*b*') identified in FIGS. 1A-1B, and FIGS. 3A-3B may have such configurations described with respect to microchannel 102*c'*.

The sensing chamber 105' downstream of the microchannel 102*c*' includes a plasmonic nanosurface 105*p*'. The plasmonic nanosurface 105*p*' may have features as that described above with respect to substrate 105*p*.

Figure 4A:
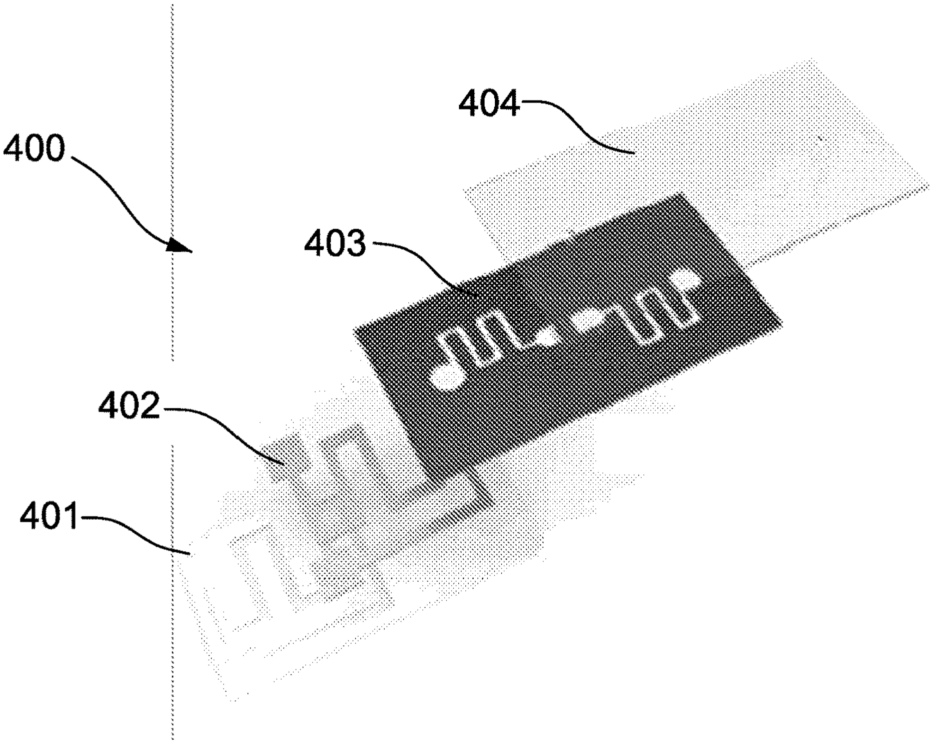
FIG. 4A is a schematic of an exploded view of a microfluidic chip according to an embodiment
Figure 4B:
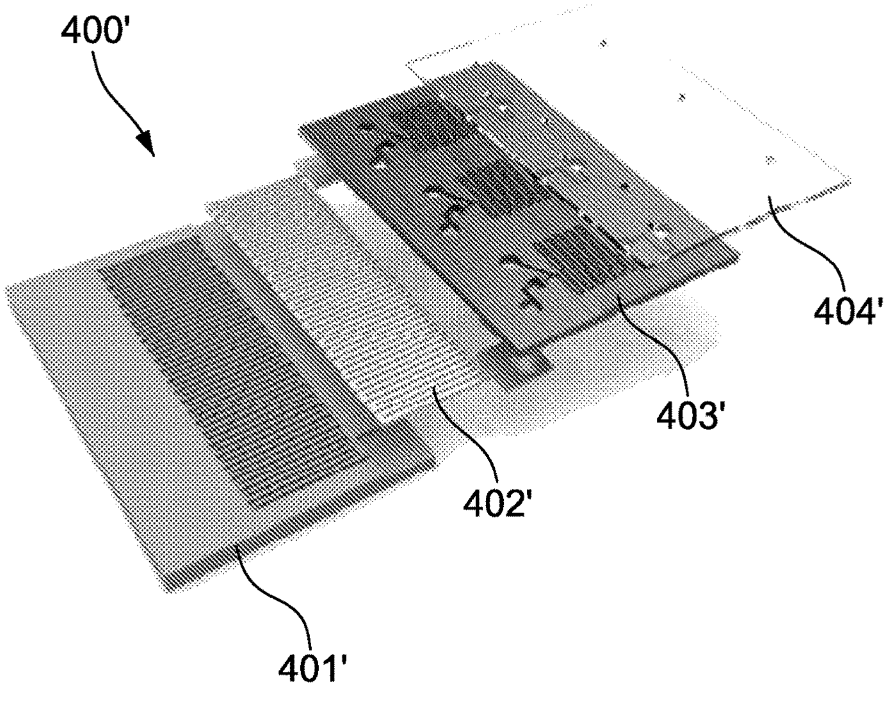
FIG. 4B is a schematic of an exploded view of a set of microfluidic chips on a unitary piece according to one embodiment.
Figure 4C:
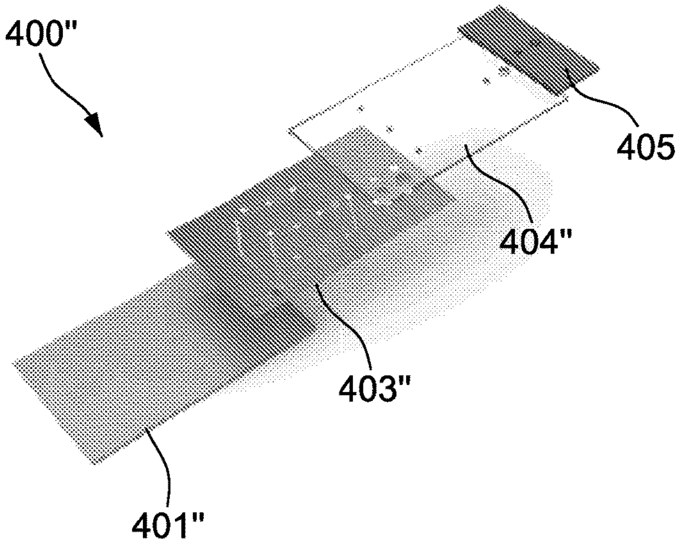
FIG. 4C is a schematic of an exploded view of a microfluidic chip according to an embodiment.

In at least some embodiments, the microfluidic chips disclosed herein may further comprise a heater element. FIGS. 4A-4C show microfluidic chips 400, 400' and 400" according to the present disclosure. These microfluidic chips 400, 400' and 400" may include features similar or identical to that described above with respect to chips 100, 100' and will not be repeated in whole for conciseness.

The microfluidic chips 400, 400' and 400" may be suitable for performing a nucleic acid amplification in the incubation chamber. The base layer 401, 401' may be a silicon base layer or any other appropriate material known in the art. A heater element 402, 402' is placed between the base layer 401, 401' and the fluid layer 403, 403'. The fluid layer 403, 403' may be composed of an epoxy-based negative photoresist (e.g., SU-8 photoresist series from KAYAKU™) or other suitable photoresist. The fluid layer 403, 403' is sealed with a layer 404, 404' of curable transparent polymer such as polydimethylsiloxane (PDMS), Flexdym™, and plastic thin sheets (e.g. polystyrene) or thin glass slides. Fluid layer 403, 403' is named as such as the inlet, outlet, microchannels and chambers discussed above, which may receive the flowing sample, may be defined in such layer.

In some embodiments, as illustrated in FIG. 4B, the microfluidic chip 400' may comprise multiple instances of the incubation chamber, as items 103, 103' and the sensing chamber, as items 105, 105', each receiving the sample from a different inlet 101, 101' for a detection multiple samples on the same microfluidic chip 400'. In further embodiments, as illustrated in FIG. 4C, the microfluidic chip 400" can comprise multiple instances of the incubation chamber 103, 103' and the sensor chamber 105, 105' fluidly connected to the same inlet 101, 101'. An additional layer 405 containing the PDMS suction buttons, to displace liquid, such as samples, store reagents may be included. Such a configuration may be particularly useful in reducing the statistical error by allowing a multiplicate measurement (e.g. duplicate or triplicate as illustrated in FIG. 5C). Those multiple instances may be located side to side (or in "parallel"), as shown, though other configurations may be contemplated, such as in series (instances longitudinally aligned).

The microfluidic chips of the present disclosure can be fabricated by a method comprising the steps of:

- Providing a base layer coated with negative photoresist. Alternatively, an uncoated base layer can be provided and the base layer is then coated with negative photoresist. Optionally, the base layer is washed prior to coating with the negative photoresist. The base layer may be a silicon wafer, for example.
- Patterning the chip using a mask that delineates an inlet, an incubation chamber, a barrier, a sensing chamber, an outlet and microchannels in between (e.g. inlet microchannels, mixing microchannels and outlet microchannels), as those described above with respect to various embodiments. The mask can be a UV mask aligner or any other appropriate mask with the design to provide the features of the inlet, the incubation chamber, the barrier, the sensing chamber, the outlet and the microchannels. The size of the chambers and/or the microchannels may vary depending on the application of the microfluidic chip and the analyte of interest. In an embodiment, the radius of inlet ports are equal to or larger than 1 mm (±0.5 mm) to allow the use of a pipette tip at the inlet. In an embodiment, the microchannel width is larger than 50 μm to reduce hydraulic resistance. In an embodiment, the detection chamber is at least 1.5 mm wide to be wide enough to make it easier to integrate the sensing platform. Those parameters may be different in other embodiments.

Creating a self-assembling monolayer (SAM) of nanoparticles at the water/air interface on a surface of the sensing chamber. Other fabless options include sacrificial polymeric nanoparticle templates and laser interference lithography. A generic approach at the water/air interface may be used which is selectively patterned to the color reading chamber upon the subsequent drying of the water droplet. Other methods include the Langmuir-Blodget method and dip-coating method. In one embodiment, the nanoparticles are polymeric such as polystyrene, silica nanoparticles, metallic nanoparticle, Janus nanoparticles or hollow spheres. The nanoparticles may be of any 3 dimensional geometry. In one embodiment, the nanoparticles have a diameter between 200 and 1000 nm or between 200 to 700 nm. The size of the nanoparticles will vary depending on the colorimetric sensor and the absorbance wavelength of its colors.

Coating the nanoparticles with a back reflector and then with a plasmon-supported metal. For example, the back reflector can be ZnO, HQS, AZ MiR™ or PMMA. In one embodiment, the plasmon-material is selected from the group consisting of gold, silver, aluminum, alloys thereof and bimetallic compositions thereof. The back reflector layer may have a thickness of 10 to 500 nm. The plasmon supported metal layer may have a thickness of 5 nm to 100 nm.

Sealing the microfluidic chip by curing a transparent polymer onto the fluid layer of the fabless microfluidic chip or by depositing a thin glass slide. The transparent polymer can be selected from the group consisting of polydimethylsiloxane, thiol-ene polymer, and Flexdym™.

Figure 5A:
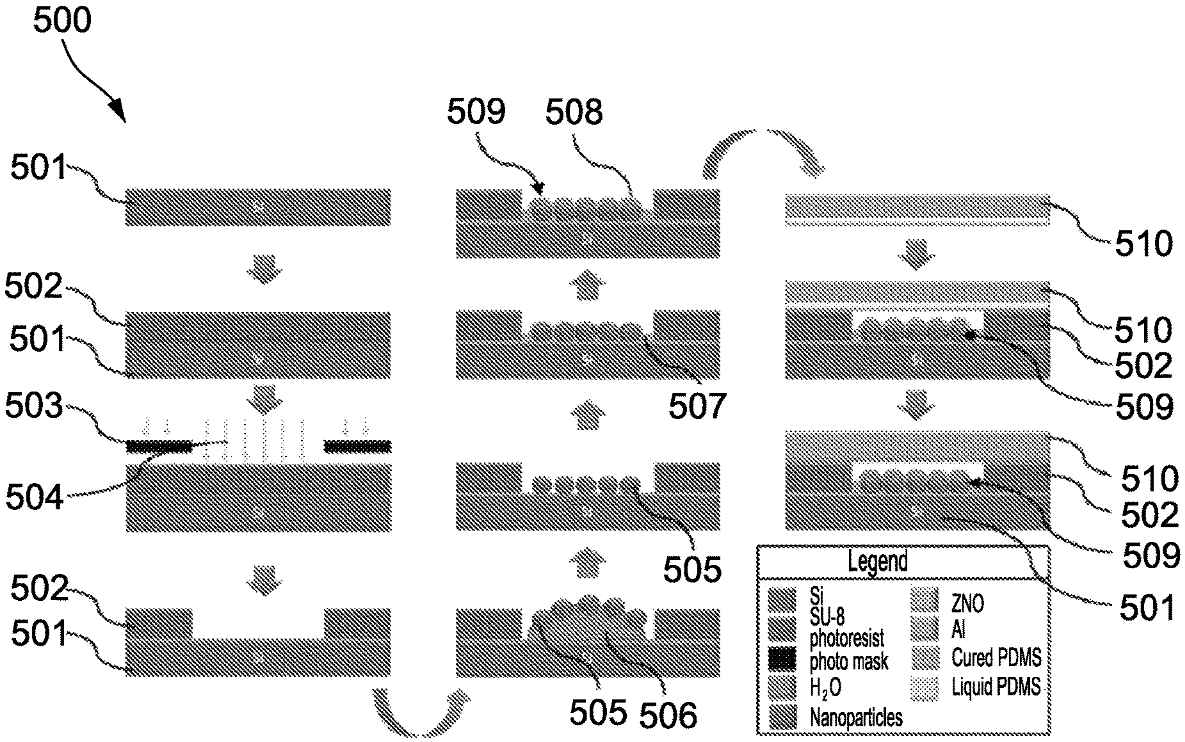
FIG. 5A is a schematic representation of cross sections of a sensing chamber of a microfluidic chip as in FIGS. 1A-1B, 3A-3B and 4A-4C at various steps during the formation of the nanostructures according to one embodiment.

FIG. 5A illustrates a cross section of the sensing chamber during a fabrication method according to one embodiment. The method is a fabrication procedure for a plasmonic enhanced microfluidic chip 500 according to an embodiment. This method may apply to any embodiment of the chips described herein. The first step is to wash a silicon wafer 501 with deionized water and then blow dry it with a nitrogen gun. Consequently spin-coating the silicon wafer 501 with a negative photoresist 502 that is SU-8 2015, and soft baking at 95° C. for 3 minutes. Next, patterning the chip design using a UV mask aligner and the design mask 503 and subsequent development with SU-8 developer with UV light 504. The next step is to form a self-assembled monolayer of nanoparticles 505 using a generic approach at the water/air interface which is selectively patterned to the color reading chamber upon the subsequent drying of the water droplet 506. The following step includes the deposition of ZnO (120 nm) 507 and aluminum (10 nm) 508 using a BJD 1800 e-beam evaporator to form nanostructures 509. Lastly, the fluid layer 502 is sealed using a cured PDMS slap 510 which is pushed for interfacing. The PDMS slap 510 is put in contact with a thin layer of freshly mixed PDMS solution, then put in contact with the fluid layer 502 with no applied pressure and left to dry at room temperature for 48 hours.

Figure 5B:
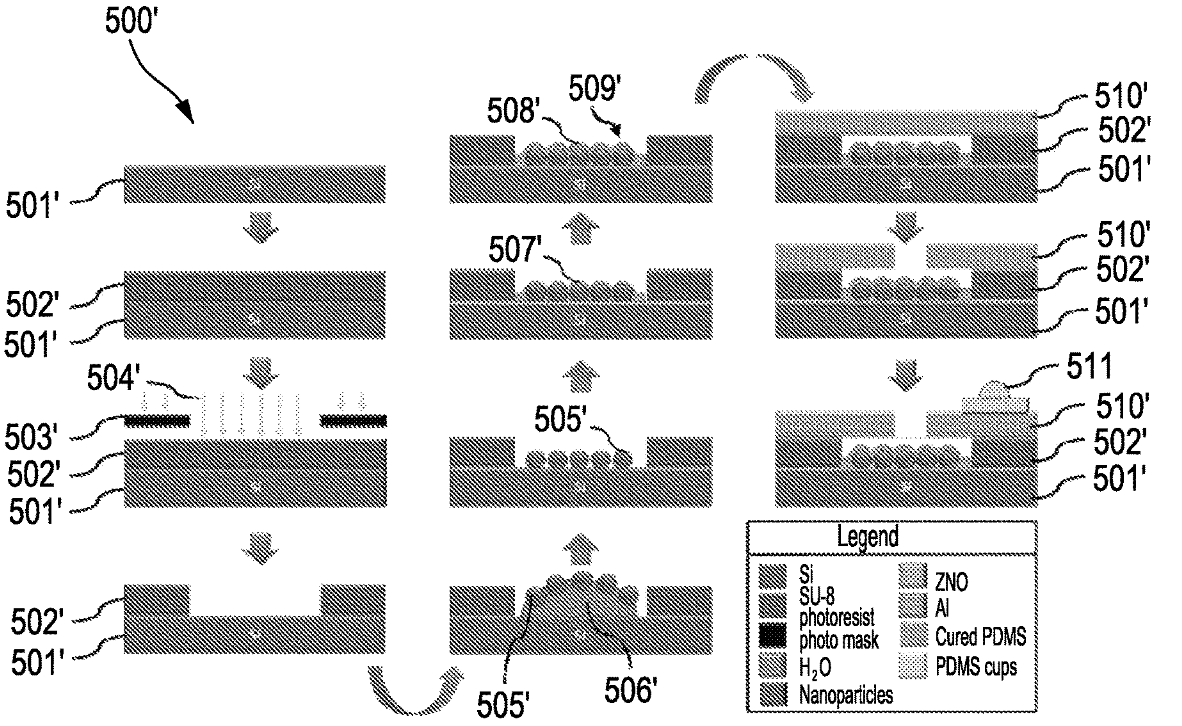
FIG. 5B is another schematic representation of cross sections of a sensing chamber of a microfluidic chip as in FIGS. 1A-1B, 3A-3B and 4A-4C at various steps during the formation of the nanostructures according to one embodiment.
Figure 5C:
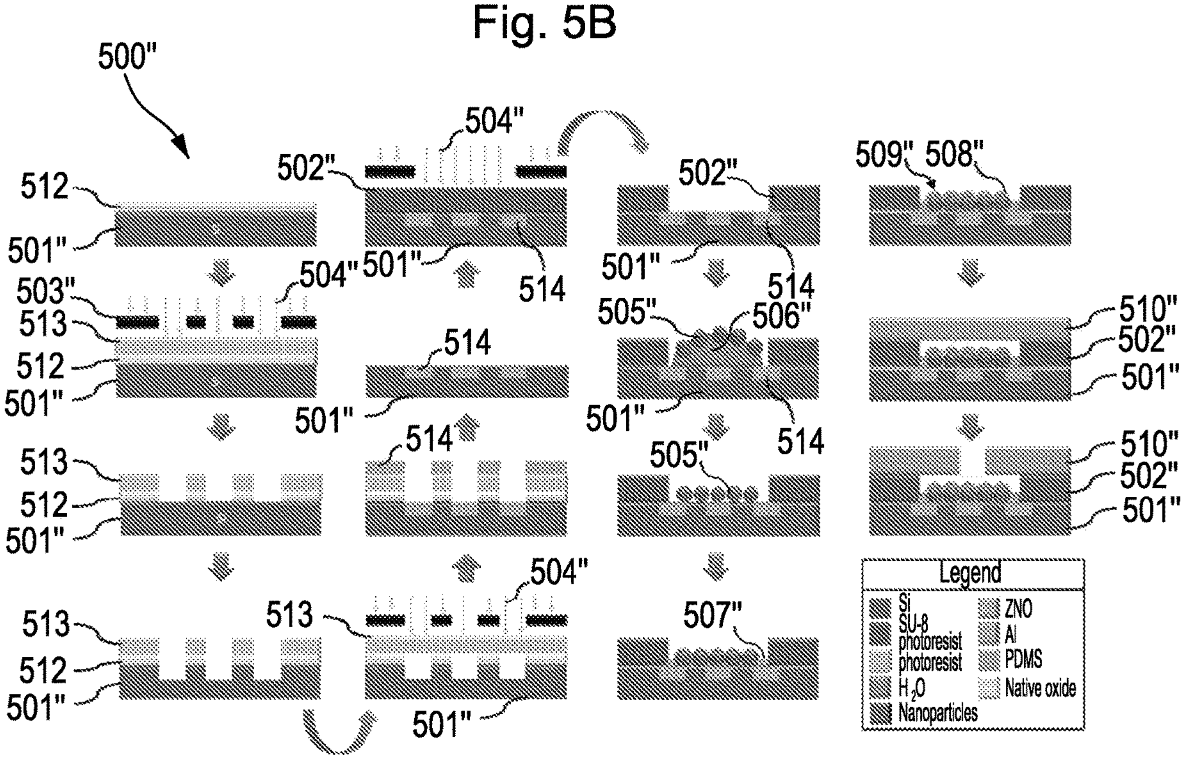
FIG. 5C is yet another schematic representation of cross sections of a sensing chamber of a microfluidic chip as in FIGS. 1A-1B, 3A-3B and 4A-4C at various steps during the formation of the nanostructures according to one embodiment.

Referring to FIGS. 5A-5C, the cross section 500 presented in FIG. 5A, and the cross sections 500' and 500" of FIGS. 5B-5C have like features that bear the same reference number for ease of reference, with prime added. Characteristics of the features described with respect to the cross section 500 may similarly apply to cross section 500' and 500" of FIGS. 5B-5C, hence they will not be repeated in whole for conciseness.

FIG. 5B illustrates a cross section 500' of the sensing chamber (as described above) with steps of a fabrication method according to another embodiment. The method is a fabrication procedure for a plasmonic enhanced microfluidic chip, as chips 100, 100', 400, 400', 400" described above, according to an embodiment. Microchannels (e.g., width: 400 μm, height: 50 μm) are patterned using a UV photolithography process, with a SU-8 layer (SU-8 2050) 502' on a silicon substrate. A plasmonic platform/surface is integrated into the chip followed by sequential thin film deposition of 120 nm ZnO 507' and 10 nm Al 508'. A thin layer of PDMS 510' (10:1, PDMS SYLGARD 184 silicone elastomer) is bonded via a standard plasma-activated process (Harrick Plasma cleaner, PDC-32G (115V), 18W). PDMS based suction cups layer 511 is fabricated using Stereolithography (SLA) printed molds (Form 3, Formlabs, USA). The suction cups 511 are subsequently bonded to the fluidic-PDMS layer 510' by plasma-activated bonding.

FIG. 5C illustrates a cross section 500" of the sensing chamber during fabrication according to another embodiment. The method is a fabrication procedure for a plasmonic enhanced microfluidic chip according to an embodiment. A three-step lithography process is utilized to pattern the embedded heater element and the microfluidic features on a silicon chip 501" with a native oxide layer 512. First, a lithography step is carried out to transfer the heater (width: 400 μm), and pad (Length: 5 mm, width: 2 mm) features to a photoresist layer 513 through a photomask 503' with the desired patterns. This is followed by a buffered oxide etch to remove native oxide 512 and a potassium hydroxide etch for a 200 nm silicon etch. Next, a lift-off process for selective deposition of the heater elements 514 in the etched grooves is carried out. This starts with a second lithography step followed by an electron-beam deposition of 240 nm aluminum using the Temescal BJD 1800. Accordingly, the lift-off is completed by submersion in suitable remover. The last lithography step is carried out to pattern the fluidic chip features including inlet/outlet ports (Φ 2 mm), lysis chamber (e.g., length: 1.74 mm, width: 1.5 mm, depth: 50 μm), mixing channels (e.g., width: 200 μm, height: 50 μm), and plasmonic window (e.g., length: 1.94 mm, width: 1.5 mm, height: 50 μm) into a SU-8 layer (SU-8 2050). In some embodiments, the fabrication methods described herein produce multiple chips on a unitary piece which can then be diced into individual chips (e.g., length: 26.5 mm, width: 35 mm) using a Disco DAD 3240 dicing saw, for example. Polydimethylsiloxane (PDMS) 510" is prepared using a 10:1 ratio of elastomer to crosslinker, degassed in a desiccator, and incubated at 65° C. The cured PDMS 510" is cut in the size of the microfluidic chip, inlet/outlet ports are punched using a PDMS puncher (Thermofisher), for example, and used to seal the chips. The sealing process includes a 50-second plasma treatment followed by incubation at 105° C.

In an application, the microfluidic chip 100, 100', 400, 400', 400" as disclosed herein may be used to detect antibiotic resistant bacteria. The chip 100, 100', 400, 400', 400" may include an antibiotic infusing (AI) chamber, which may correspond to the incubation chambers 103, 103' described above, having bacteria entrapping micropillars, which may correspond to the micropillars 104*p*, 104*p*' of the barriers 104, 104' discussed above, and a plasmonic color-sensitive (PCS) chamber, which may correspond to the sensing chambers 105, 105' discussed above. The Al chamber is connected to an inlet, as inlet 101, 101', by an inlet microchannel, as 102*a*, 102*a*'. The Al chamber is connected to a mixing microchannel as 102*c*, 102*c*' and are separated by the micropillar barrier which may entrap bacteria in the Al chamber and prevent them from passing through into the sensing PCS chamber. The sample is incubated in the incubation chamber for a time sufficient to allow a reaction between an agent indicating the presence or absence of bacteria and the bacteria. In one embodiment, the agent can be the colorimetric agent. In another embodiment, the agent may react with a colorimetric agent based on the presence or absence of bacteria. The colorimetric sensor can be provided in a second inlet as inlet 106' illustrated in FIG. 3B downstream of the Al chamber.

Figure 6A:
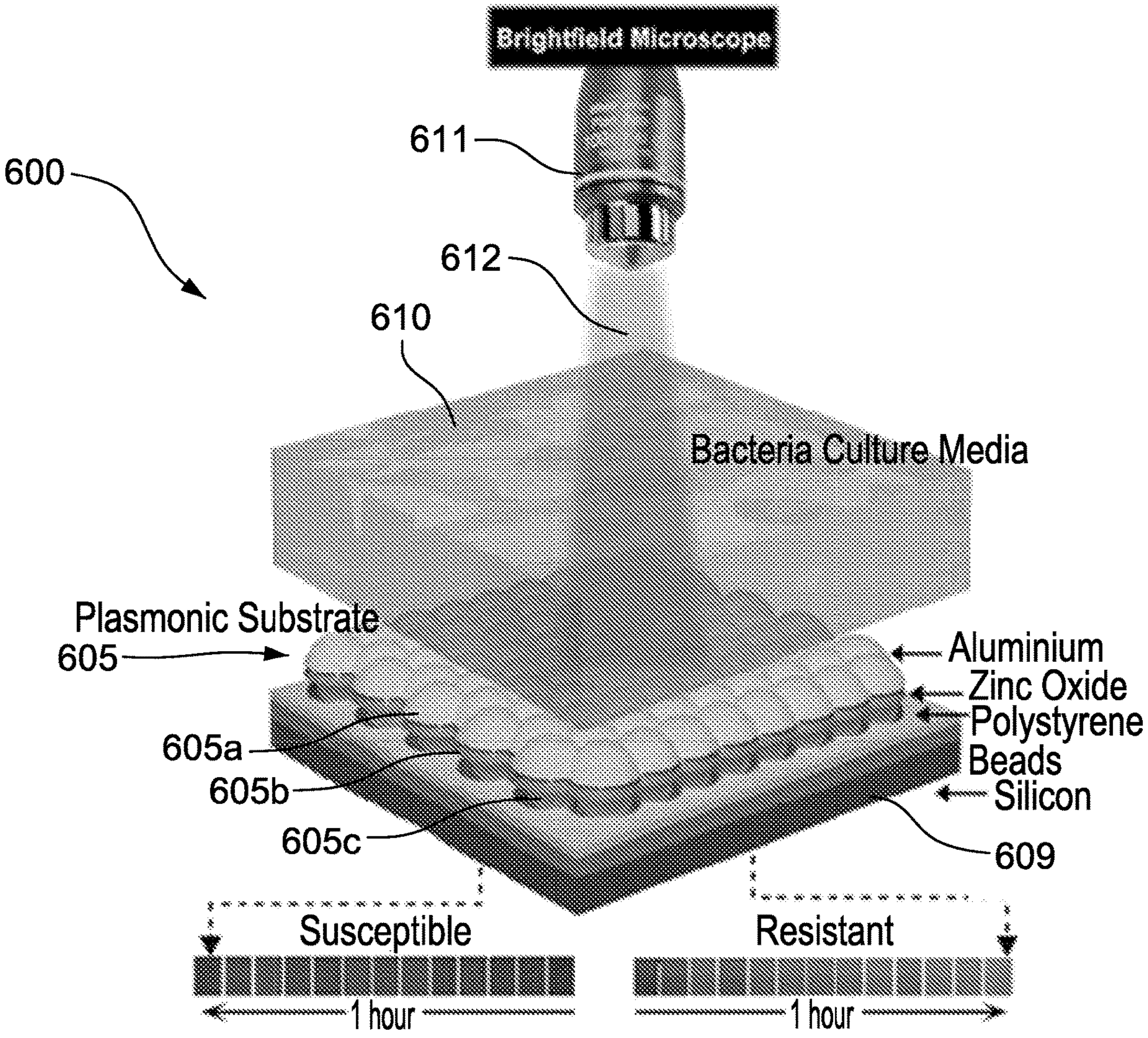
FIG. 6A is a schematic expanded exploded view of nanostructures on the surface of a sensing chamber of a microfluidic chip according to one embodiment.

FIG. 6A illustrates an expanded exploded cross section view of an exemplary plasmonic nanosurface 600 as that referred to above at item 105*p*, 105*p*'. In some embodiments, the plasmonic nanosurface 105*p*, 105*p*', 600 has a surface area of at least 250 $nm^2$. In some embodiments, the surface area is between 250 and 350 $nm^2$, between 250 and 500 $nm^2$, between 250 and 1000 $nm^2$, between 250 and 2000 $nm^2$. In other embodiments, the size of the plasmonic nanosurface can be larger than 350 $nm^2$, such as 2000 $nm^2$ or even more. The exemplary plasmonic nanosurface 600 is shown in use during the sensing of bacteria. The exemplary plasmonic surface includes nanostructures 605 on a silicon base 609. The nanostructures 605 can be fabricated via a self-assembly monolayer method using polystyrene nanoparticles 605*c* with a variety of sizes (d=200-1000 nm). A thin layer (120 nm) of ZnO and a layer of 20 nm of aluminum can be deposited on the hexagonal close-packed (HCP) lattice of the nanoparticles 405*c* as back-reflector layer 605*b* and metallic layer 605*a*, respectively. In some embodiments, using ZnO as a back-reflector 605*b* instead of the commonly used hydrogen silsesquioxane (HSQ) allows for reducing the toxicity of the color-sensitive chamber 105, 105' to minimize the risk of manipulating antibiotic effect by the microfluidic chip. The media 410 from the Al chamber 103, 103' is injected to the PCS chamber 105, 105' for colorimetric sensing. The generation of colors via plasmonic metasurfaces may produce high-resolution, durable, and sensitive colors. Conceptually the sub-wavelength nanostructures 605 act as nanoantenna when exposed to the electromagnetic field of the light 612 which can be demonstrated using Maxwell equations through finite difference time domain simulation. The resonance of the nanoantenna according to the refractive index of the media 610 identifies the absorption of light 612 and consequently the generation of the colors. The plasmonic color change may be sensitively captured in the PCS chamber 105, 105' via a brightfield microscope 611 which reflects the changes in the refractive indexes of media 610 entering the PCS chamber 105, 105'. The red-green-blue (RGB) values of the plasmonic colors can be analyzed to quantify the changes in the colors.

Figure 6B:
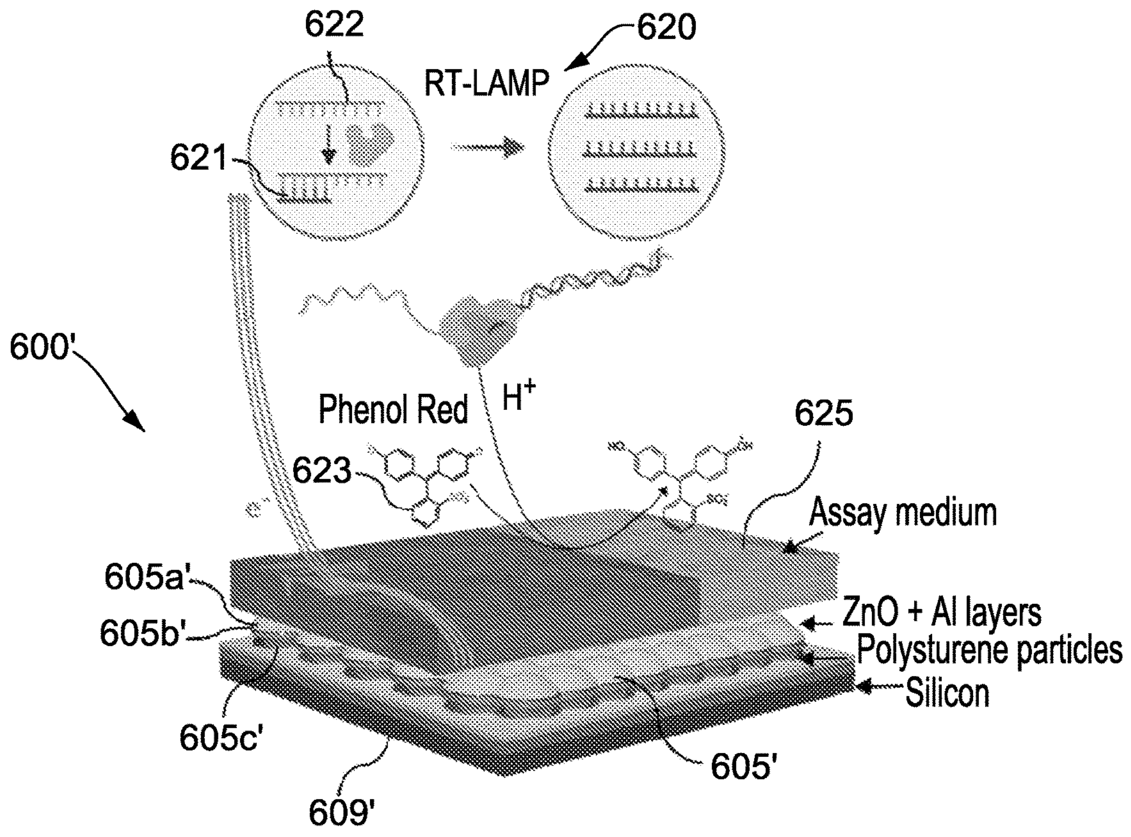
FIG. 6B is a schematic expanded exploded view of nanostructures on the surface of a sensing chamber of a microfluidic chip in use for pathogen genotypic detection through a colorimetric nucleic acid detection assay assisted by a nanopatterned plasmonic surface according to one embodiment.
Figure 6C:
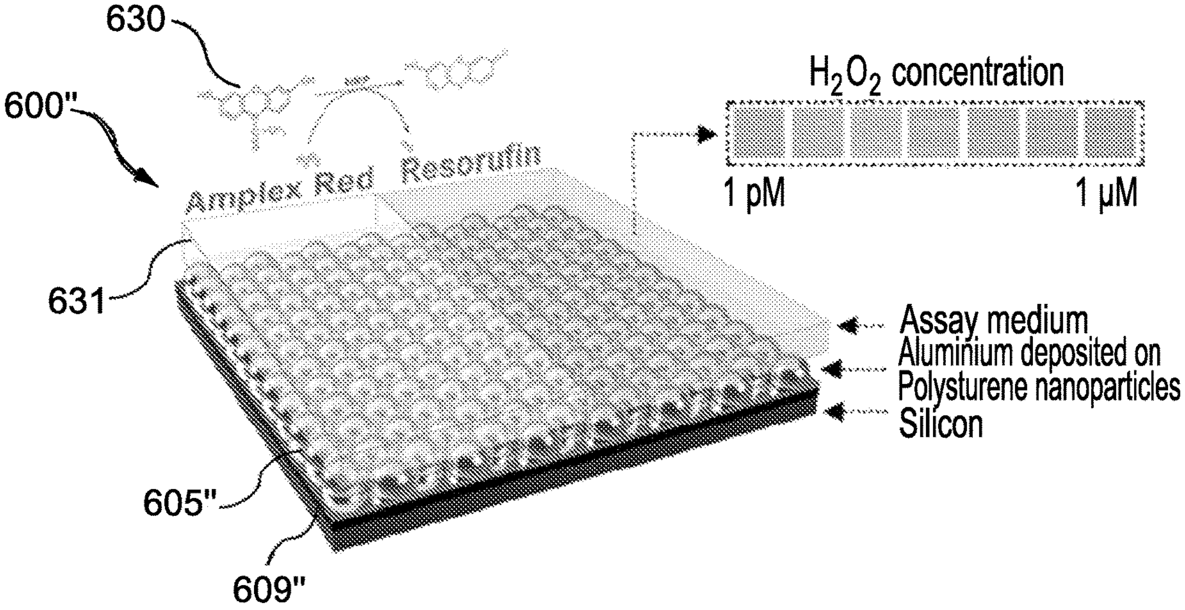
FIG. 6C is a schematic expanded exploded view of nanostructures on the surface of a sensing chamber of a microfluidic chip in use for $H_2O_2$ detection through amplex red colorimetric assay assisted by a nanopatterned plasmonic surface according to one embodiment.

Referring to FIGS. 6A-6C, the plasmonic surface 600 presented in FIG. 6A, and the plasmonic surface 600' and 600" of FIGS. 6B-6C have like features that bear the same reference number for ease of reference, with prime added. Characteristics of the features described with respect to the plasmonic surface 600 may similarly apply to plasmonic surface 600' and 600" of FIGS. 6B-6C, hence they will not be repeated in whole for conciseness.

In yet another application, the microfluidic chips disclosed herein such as chips 400, 400', 400", may be used to detect nucleic acid sequences by nucleic acid amplification (such as PCR, RT-LAMP and RCA). In FIG. 6B, an exemplary plasmonic nanosurface 600' is shown in use during the sensing of nucleic acids. Even though traditional PCR may provide accurate and sensitive detection of nucleic acids, the test protocol is complex, expensive and is mainly suited to centralized diagnostic laboratories. PCR may require at least 4 to 6 hours before results are available due to the many thermal cycles required for the amplification. Above all, in situations where there is a shortage of RNA extraction reagents such as in a pandemic situations like the SARS-CoV-2 pandemic the disadvantages of traditional PCR are clear. In some embodiments, the microfluidic chips of the present disclosure may integrate a PCR 620 in the incubation chamber with primers 621 specific to a target nucleic acid sequence 622 (in this case the analyte). In such embodiments, a pH sensitive colorimetric sensor can be used, such as phenol red 623. The microfluidic chips 100, 100', 400, 400', 400" as disclosed herein may reduce the consumption of reagents (cost) as well as the number of cycles (time) while maintaining the sensitivity and accuracy of traditional PCR assays. The microfluidic chip can employ various established amplification assay to amplify the target nucleic acid sequence (e.g. RNA) such as a reverse transcription loop-mediated isothermal amplification (RT-LAMP) assay or a rolling circle amplification (RCA) assay which is particularly suitable for single nucleotide polymorphism (SNP) detection. The amplifications release protons (H+) that change the solution pH and the color of the media 625 in the presence of a pH-sensitive dye 623. In some embodiments, a single-step amplification is sufficient to obtain adequate sensitivity. More cycles may be performed for increased sensitivity at the expense of the assay run time.

In yet another embodiment, the microfluidic chip disclosed herein can be used to sense cancerous cells. In FIG. 6C, an exemplary plasmonic nanosurface 600" is shown in use during the sensing of cancerous cells. As previously described, a micropillar barrier can be used in the chip to retain the cells and a colorimetric dye 630 sensitive to $H_2O_2$ reveals the presence of cancer cells by inducing a change in the media 631 with the change in $H_2O_2$. A multitude of analytes can be detected with the present microfluidic chip 100, 100', 400, 400', 400" as long as there is a corresponding colorimetric sensor for the analyte.

In one aspect of the present disclosure, there is provided a method to sense an analyte which can be performed using the microfluidic chips 100, 100', 400, 400', 400" of the present disclosure and has the following steps. First, the sample can be prepared by mixing the sample with a colorimetric sensor and the necessary reagents if applicable (primers and reverse transcriptase in the case of PCR for example). The sample may be mixed prior to being provided at the inlet 101, 101' of the microfluidic chip 100, 100', 400, 400', 400" or the sample and other reagents may be provided at the inlet 101, 101' and subsequently mixed in the microfluidic channels 102*a*, 102*a*', 102*c*' of the chip 100, 100', 400, 400', 400". The sample flows to the incubation chamber 105, 105' where it is incubated for a predetermined period of time. The incubation period depends on the analyte and assay performed. In one embodiment, the incubation period is less than 1 h 30 mins, less than 1 h, less than 45 mins, less than 30 mins, less than 25 mins, less than 20 mins, less than 15 mins or less than 10 mins. After the incubation, the sample is pushed across the barrier and into the sensing chamber, for example with a pressure differential. In one embodiment, the sample is pushed by adding more liquid at the inlet 101, 101'. The plasmonic color change is analyzed in the sensing chamber 105, 105' using a detection device such as a brightfield microscope 611. In one embodiment the total run time of the device is less than 1 h 30 mins, less than 1 h, less than 45 mins, less than 30 mins, less than 25 mins, less than 20 mins, less than 15 mins or less than 10 mins.

The data acquired can be conveniently converted to the feasible CIE color gamut, each picture of the data set loaded to a program to be read as a 3 layer matrix, each pixel having 3 components, one per layer, corresponding to its red (R), green (G) and blue (B) value. The processing may involve image cropping and a sample selection. A simple average calculation can be run individually to get an overall value for R, G and B components for each of the samples. Then, the mean across the collection can be calculated.

In one embodiment, there is provided a method of sensing a nucleic acid analyte, for example a viral DNA or RNA (e.g. SARS-CoV-2) with the microfluidic chip 100, 100', 400, 400', 400" of the present disclosure. When the analyte is a nucleic acid, the microfluidic chip 100, 100', 400, 400', 400" preferably includes a heating element as illustrated in the chips 400 and 400' of FIGS. 4A and 4B. The microfluidic chip includes a plasmonic nanosurface 105*p*, 105*p*' prepared with nanoparticles having a diameter between 200 and 700 nm. In some embodiments, the sample is prepared with phenol red as the colorimetric sensor, a RT-LAMP and primers specific to the target nucleic acid analyte, for example the ORF1ab gene of SARS-CoV-2. The reaction volume can be mixed in the microchannels 102*a*, 102*a*' of the microfluidic chip and incubated at around 65° C. (e.g. ±5%) using embedded on-chip heating elements in the incubation chamber 103, 103'. Preferably, a one-step amplification occurs in the incubation chamber 103, 103' but multiple amplification cycles are also contemplated herein. The incubation time may be less than 1 h, less than 45 mins, less than 30 mins, less than 25 mins, less than 20 mins, less than 15 mins or less than 10 mins. In the presence of the target nucleic acid analyte, such as the ORF1ab gene of SARS-CoV-2, amplification will occur thereby releasing $H^+$ protons in the media and acidifying the pH. The sample is then flowed to the sensing chamber 105, 105' where the plasmonic color change is analyzed using a brightfield microscope. In a preferred embodiment the chip run time is 10 minutes or less. The present method can avoid multiple thermal cycles and operates at the microscale. Therefore, compared to traditional PCR the consumption and cost of reagents as well as the assay time are reduced. The reduction of volume of reagents can be estimated to be 10 times lower than off-chip RT-LAMP (20 μl per reaction) and conventional RT-PCR (50 μl per reaction). The colorimetric assisted microfluidic chip 100, 100', 400, 400', 400" based on one step RNA amplification is time efficient and cost-effective test method for point of care diagnostics and routine screenings of target nucleic acid analyte, for example bacterial or viral nucleic acids.

In some embodiments, the microfluidic chip 100, 100', 400, 400', 400" can be used for the sensing of bacteria, such as antibiotic resistant bacteria. In such embodiments, the operational procedure of the chip 100, 100', 400, 400', 400" can be to inject the bacteria containing growth media along with antibiotic of interest and a resazurin solution at the inlet 101, 101'. The growth media and resazurin solution can be mixed in the microchannels 102*a*, 102*a*' before reaching the incubation chamber 103, 103'. The microfluidic chips can be incubated for one hour through time intervals of 5 minutes. After incubation, the liquid in the incubation chamber 103, 103' is pushed towards the sensing chamber 105, 105' while the bacteria remains entrapped behind the barrier 104, 104' which preferably contains micropillars 104*p*.

In another embodiment the microfluidic chip 100, 100', 400, 400', 400" is used for genotypic detection of pathogens. The chip operates based on two characteristic chambers previously described, the incubation chamber 103, 103' and the sensing chamber 105, 105'. The chip includes a mixing microchannels channels 102*a*, 102*a*', 102*c*, 102*c*' for mixing the incoming sample solution with a nucleic acid assay solution in a fixed ratio. In such embodiments, the operational procedure of the chip can be to inject the pathogen containing media from the inlet 101, 101'. The media will flow to the incubation chamber 103, 103' where a thermal lysis at 95° C. for 5 mins to release the pathogens nucleic acid can occur. Next, the samples are pushed to the mixing channels 102*c*, 102*c*' along with the nucleic acid assay solution to get mixed. When the mixture reaches the sensing chamber, 105, 105', the microfluidic chips are heated for one hour through variable time intervals (1, 3, 7, 10, 15, 20, 30, 40, 50, 60 minutes). After each time interval, the color of the liquid in the PCS chamber can be determined.

Example I

When bacteria is the analyte to be detected, the resazurin assay can be used to determine the presence or concentration of bacteria. Resazurin assays can be used to study the susceptibility of the pathogenic bacteria against antibiotic infusion. Indeed, the resazurin assay is a well-known colorimetric assay that is widely used in clinical colorimetric read-out systems to identify the viability of the cells. The resazurin assay functions in two steps. First, the assay is absorbed by the membrane of the cell and second, over the metabolic reactions in the live cells the resazurin molecule is reduced to resorufin. The chemical structures of these two molecules are shown below.

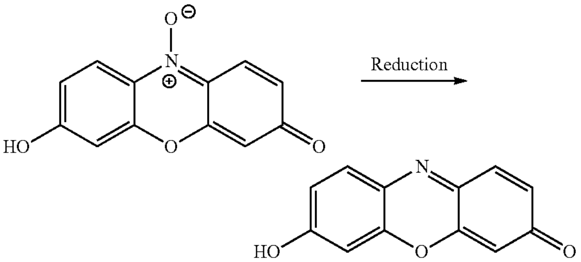

As more resazurin molecules is reduced to resorufin, the color of the cell medium changes from navy blue to light pink. The duration of color change depends on the absorption of resazurin by cells, the viability of the cells to reduce the assay, and the concentration of the cells. Despite the ease of handling and abundance of resazurin assay colorimetry, this method suffers from low sensitivity, being time-consuming, and non-quantifiable in terms of the readout signal. In this example, a fabless plasmonic color microfluidic chip was successfully used in the sensing of bacteria. More specifically, the microfluidic chip of the present disclosure was able to detect a color change during the NADH-controlled conversion of resazurin to resorufin which is an indicator of cell viability in presence of different chemicals.

Ampicillin resistant *Escherichia coli* strain (Amp resistant *E. coli,* #211540, Merlan scientific, Ontario, Canada) was cultured overnight at 37° C. in Luria broth (LB) media supplemented with 100 μg/mL Ampicillin (#216858, Merlan scientific, Ontario, Canada). Next, the bacterial concentration was determined by optical density technique using a Spectronic 21D spectrophotometer. Subsequently, aliquots of different concentrations were prepared for the antibiotic susceptibility testing experiments.

For resistant bacterial samples, aliquots were prepared of different concentration of Amp resistant *E. coli* ($5\times10^5$ CFU/mL, $10^3$ CFU/mL, $10^2$ CFU/mL, and 50 CFU/mL), MRSA (5×105 CFU/mL), and Ciprofloxacin (Cipro) resistant PA ($5\times10^5$ CFU/mL). A resazurin solution of 0.02% resazurin (R7017, Millipore Sigma, Ontario, Canada) supplemented with 100 μg/mL Ampicillin, 4 μg/mL Oxacillin, and 2 ug/mL Ciprofloxacin for Amp. Resistant *E. coli*, MRSA, and Cipro. Resistant PA respectively was used. The aliquots were incubated at 37° C. for different periods of time starting from 0 minutes incubation to a 60 minutes with a time step of 5 minutes. For susceptible bacterial samples, aliquots of Amp resistant *E. coli* were prepared ($5\times10^5$ CFU/mL, $10^3$ CFU/mL, $10^2$ CFU/mL, and 50 CFU/mL), MRSA ($5\times10^5$ CFU/mL), and Cipro. Resistant PA ($5\times10^5$ CFU/mL). A resazurin solution of 0.02% resazurin supplemented with 50 μg/mL Kanamycin, 1 ug/mL Ciprofloxacin, and 4 ug/mL Gentamicin for Amp. Resistant *E. coli*, MRSA, and Cipro. Resistant PA respectively was used. The aliquots were incubated at 37° C. different periods starting from 0 minutes incubation till 60 minutes with a time step of 5 minutes.

For the minimum inhibitory concentration (MIC) study, aliquots of $5\times10^5$ CFU/mL Amp resistant *E. coli* with resazurin/kanamycin solution were used. Solutions with different kanamycin concentrations of 1 μg/mL, 2 μg/mL, 4 μg/mL, 8 μg/mL, 16 μg/mL, 32 μg/mL, and 50 μg/mL were used to determine the MIC dose. $5\times10^5$ CFU/mL MRSA aliquots were prepared using resazurin/oxacillin solution using different concentrations of oxacillin antibiotic (16 μg/mL, 32 μg/mL, and 64 μg/mL). Then $5\times10^5$ CFU/mL Cipro. Resistant PA aliquots were prepared using resazurin/ciprofloxacin solution using different concentrations of ciprofloxacin antibiotic (8 μg/mL, 16 μg/mL, and 32 μg/mL).

For the Clinical & Laboratory Standards Institute (CLSI) MIC protocol bacteria were streaked on LB agar overnight and resuspended in water aliquot. The aliquot was measured, and the bacteria concentration was adjusted to $10^6$ CFU/mL in LB media. A 96 well plate with an antibiotic gradient from 128 μg/ml to 0.125 μg/ml in a 2-fold concentration dilution step was prepared with a positive control with no antibiotics. Next, the bacteria were introduced to each well of the 96 well plate for a final bacteria concentration of $5\times10^5$ CFU/mL. The well plates were cultured overnight. The minimum inhibitory concentration was determined as the antibiotic concentration that did not show any signs of bacterial growth.

For the spiked human sample experiment, human urine was centrifuged at 5000 rcf for 5 minutes to remove large particles. It was subsequently spiked with $5\times10^5$ CFU/mL and mixed with a solution of resazurin to a final concentration of 0.02%. No antibiotics were added for the control aliquots, 100 μg/mL ampicillin was added for resistant aliquots and 50 μg/mL Kanamycin was added for susceptible aliquots. The aliquots were incubated at 37° C. different periods starting from 0 minutes incubation till 60 minutes with a time step of 5 minutes.

For the spiked human sample experiment, human whole blood was centrifuged in two steps first at 150 rcf for 10 minutes followed by 7000 rcf for 3 min. It was subsequently spiked with 100, 50 or 20 CFU/mL and mixed with a solution of resazurin to a final concentration of 0.01%. No antibiotics were added for the control aliquots, 32 μg/mL ampicillin was added for resistant aliquots and 16 μg/mL kanamycin was added for susceptible aliquots. The aliquots were incubated at 37° C. different periods starting from 0 minutes incubation till 150 minutes with a time step of 5 minutes.

To rapidly detect the sample color change on the platform the reflectance spectra was measured using a Lambda 750 UV/Vis/NIR Spectrophotometer (PerkinElmer). The incident and collected light beams had normal incidence to the platform. Further, optical imaging was performed under highly controlled environment using Nikon Eclipse LV150 (Nikon) with a ×100, 0.9 NA air objective and Nikon digital sight ds-fil CCD camera with a white reference of R:0.75 G:1.0 B:2.36.51.

The microfluidic chip used was similar to that illustrated in FIG. 1B, having two characteristic chambers 1) antibiotic infusing chamber (AI) 103 equipped with bacteria entrapping micropillars 104*p*; and 2) plasmonic color-sensitive chamber (PCS) 105. The operational procedure of the microfluidic chip was to inject the bacteria containing growth media along with an antibiotic of interest and 0.02% resazurin solution from the inlet to get mixed in the Al mixing and entrapment chamber. Microfluidic chips were incubated for one hour through time intervals of 5 minutes. After incubation, the liquid in the Al chamber 103 was pushed towards the PCS chamber 105 sensing chamber while the bacteria was entrapped behind the micropillars 104*p*.

The plasmonic nanosurface 105*p* in the PCS chamber 105 was fabricated via a self-assembly monolayer method using polystyrene nanoparticles with a variety of sizes (d=200-1000 nm). A thin layer (120 nm) of ZnO and 20 nm of aluminum was deposited on the hexagonal close-packed (HCP) lattice of the nanoparticles as back-reflector and metallic layer, respectively. Using ZnO as a back-reflector instead of the commonly used HSQ allowed for reducing the toxicity of the color-sensitive chamber to minimize the risk of manipulating antibiotic effect by the nanosurface. The media from the Al chamber 103, 103' was injected to the PCS chamber 105, 105' for colorimetric sensing. The generation of colors via plasmonic metasurfaces produced high-resolution, durable, and sensitive colors. Conceptually the sub-wavelength nanostructures act as nanoantenna when exposed to the electromagnetic field of the light which can be demonstrated using Maxwell equations through finite difference time domain simulation. The resonance of the nanoantenna according to the refractive index of the media identifies the absorption of light and consequently the generation of the colors. In this example, the goal of the microfluidic chip tested was to sensitively capture the plasmonic color change in the PCS chamber 105 via a brightfield microscope 611 which reflects the changes in the refractive indexes of media entering the PCS chamber 105. The RGB values of the plasmonic colors were then analyzed to quantify the changes in the colors.

To conveniently convert the microscopy results to the feasible CIE color gamut, each picture of the data set loaded to MATLAB was read as a 3 layer matrix, each pixel has 3 components, one per layer, corresponding to its R, G and B value. The processing involved image crop and a sample selection. A simple average calculation was run individually to get an overall value for R, G and B components for each of the 5 samples generated. Following that, the mean across the collection was calculated. The error bar was computed at 1 standard deviation.

The conversion to XYZ color systems was made through a software function, using as white point reference the CIE standard illuminant pair: D50, [0.9642, 1.0000, 0.8251] also known as 'horizon light' which is correlated color temperature of 5003 K.

The x and y values were calculated following the equations (1 and 2) afterward they were used as coordinates to indicate the overall color value of each picture in the data set into the International Commission on Illumination color space widely known as CIE 1931 to evaluate the total spanning of the resazurin color change.

$$x = \frac{X}{X + Y + Z} \quad (1)$$

$$y = \frac{Y}{X + Y + Z} \quad (2)$$

All images were processed and analyzed through a MATLAB™ script which allowed the analysis of multiple images simultaneously. The TIFF files were loaded and cropped to 80% of their original dimensions to avoid the coffee-ring effect. An option for the manual crop was also available. For each image, five samples of 480×480 pixels were randomly selected. Subsequently, for each the R, G and B values were averaged followed by the calculation of the mean RGB value and error across them. Succeeding their conversion to XYZ and x, y color systems. The RGB values of each image with its corresponding error bar were plotted against time. Additionally, the x and y values were scattered on the CIE1931 color space to analyze the color change through time.

Figure 7A:
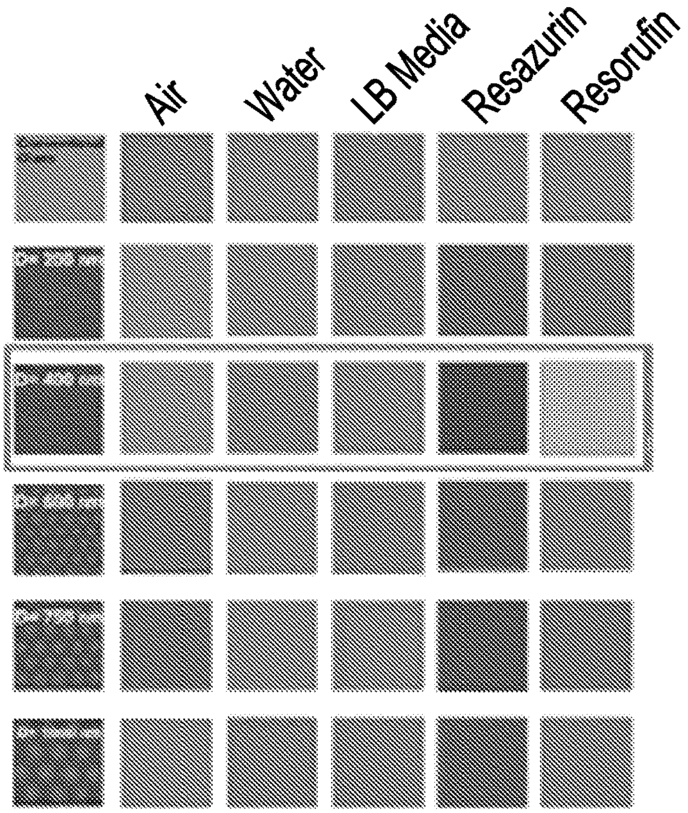
FIG. 7A is a bright-field microscopy of different platforms (glass, 200 nm, 400 nm, 600 nm, 750 nm, and 1000 nm nanoparticles diameter) under D50 white light. Different media were used including air, water, Luria Broth (LB) media (RI. 1.338), resazurin, and resorufin.
Figure 7B:
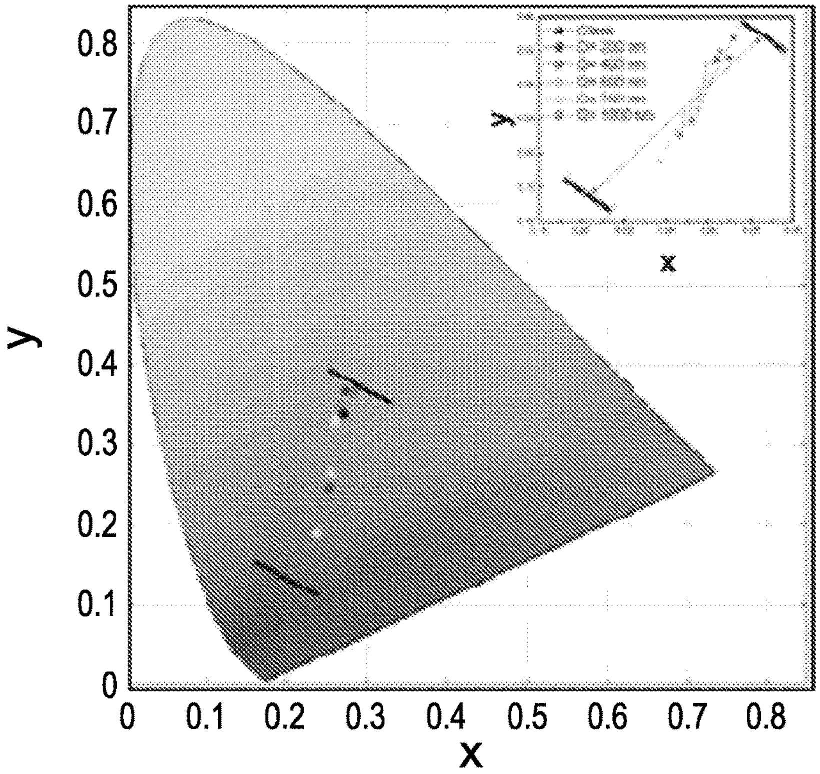
FIG. 7B is a 2D CIE 1931 chromaticity diagram showing the color change between the resazurin and resorufin for different platforms.
Figure 7C:
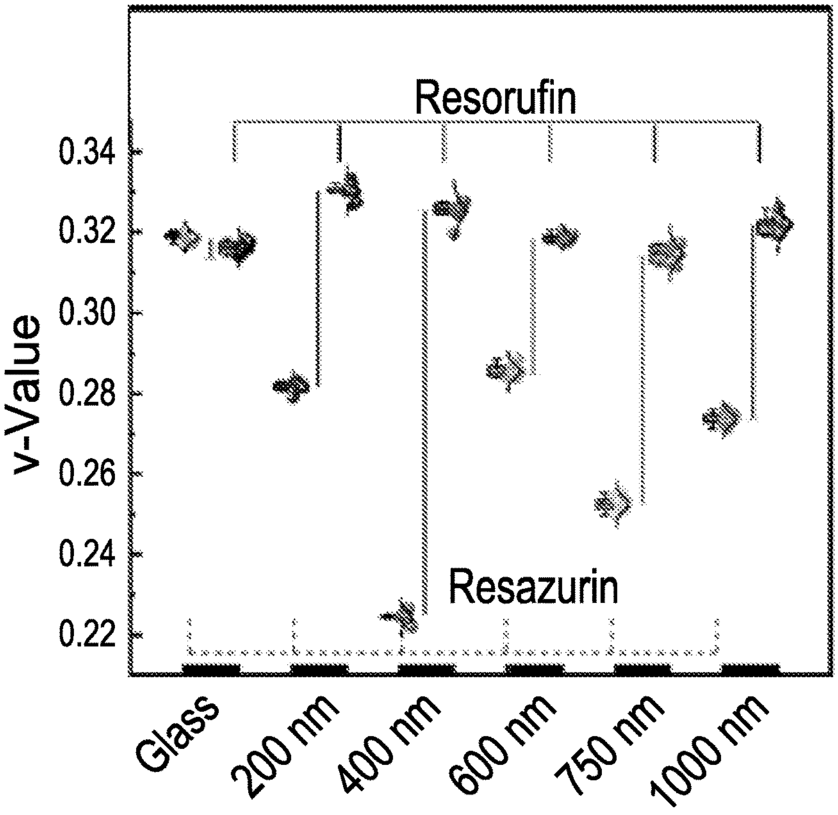
FIG. 7C is a dot-plot graph of y-value of 30 random points derived from each platform in resazurin and resorufin.

One of the objectives of the microfluidic chip was sensing the viability of bacteria infused with antibiotics in the presence of resazurin. The characteristics of the PCS nanosurface were optimized experimentally and theoretically for that objective. The color of the plasmonic nanosurface of the sensor chamber other than the refractive index of the media depends on geometrical features of the plasmonic nanostructures i.e. size and pitch of nanoparticles. In a close-packed lattice of the self-assembled nanoparticles, the diameter of the nanoparticles also determines the pitch of the lattice, therefore, nanosurfaces made with polystyrene nanoparticles with diameters from 200 nm to 1000 nm were investigated and compared with conventional glass substrate in different media. The optimized geometrical size of the plasmonic monolayer was investigated. First, the color of the plasmonic polystyrene monolayers in different media; air, water, luria broth (LB), resazurin, and resorufin, was captured via a 100× objective of brightfield microscope. The absorption efficiency of the plasmonic nanoparticles in each medium with a specific refractive index determined the vitality of the generated color. The energy of the beam incident is removed from the beam path upon its interaction with plasmonic matter by absorption and scattering. FIG. 7A shows the color sensitivity of the plasmonic surface against the diameter of the polystyrene nanoparticles. In each media, the same self-assembled plasmonic substrate was used to eliminate the shape factors, structural defects, and other matrix effects. To investigate the wideness of color gamut between the resazurin and resorufin, RGB values were extracted from the microscopy images and converted to x-y coordinates on standard CIE 1931 chromaticity diagram using standard conversion models (FIG. 7B). The lattice made by 400 nm nanoparticles demonstrated a larger color gamut between resazurin (navy-blue) to resorufin (cyan-green). To confirm that, the y-value of 30 random points was derived from each platform in resazurin and resorufin and plotted via a dot-plot graph (FIG. 7C) demonstrating the highest distance between y-value of the platform in resazurin versus in resorufin was attributed to 400 nm polystyrene nanoparticles.

Figure 7D:
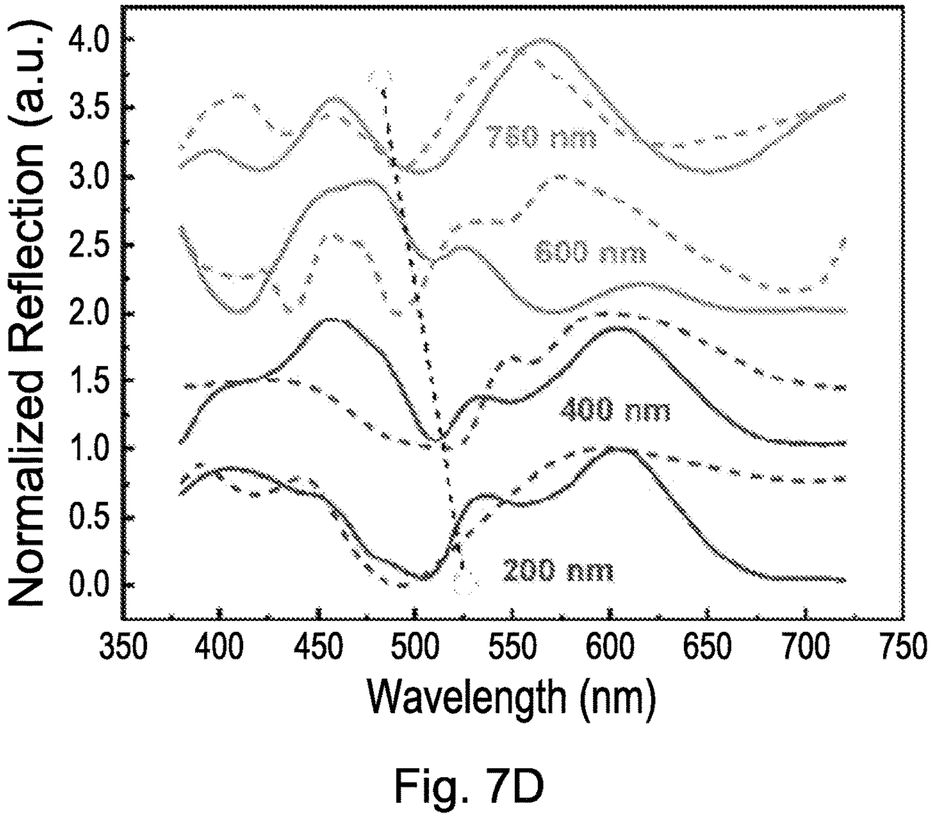
FIG. 7D is a simulated and experimental reflectance spectra of plasmonic substrates with different diameters.
Figure 7E:
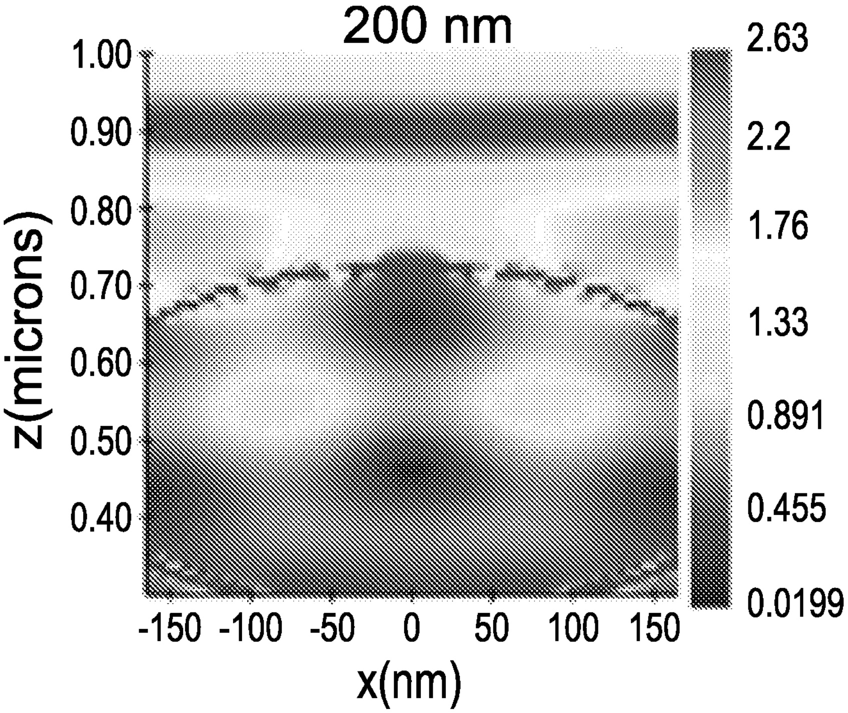
FIG. 7E shows the electric field distribution in nanocavities having a size 200 nm.
Figure 7F:
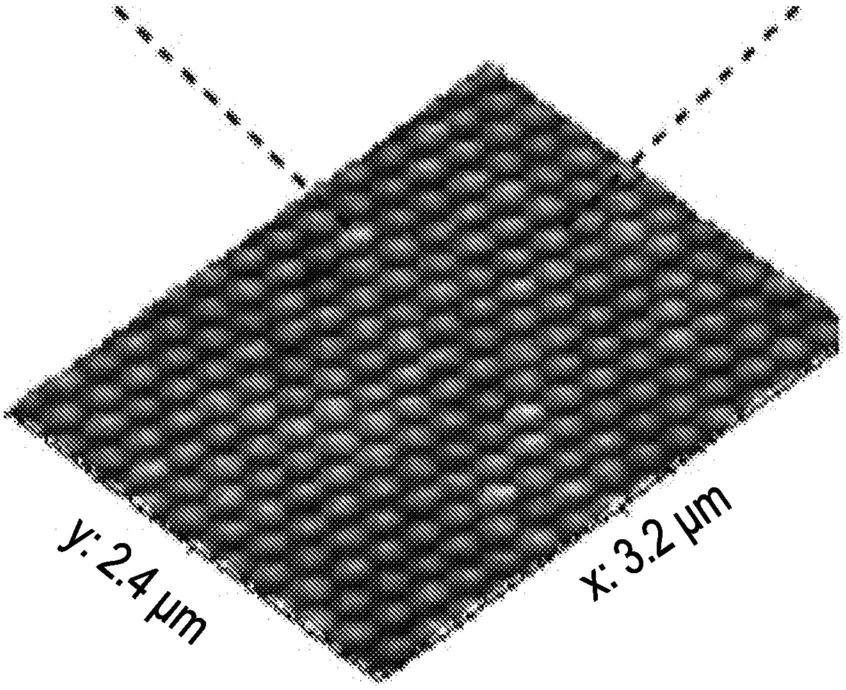
FIG. 7F is an AFM image of the nanocavities of FIG. 7E.
Figure 7G:
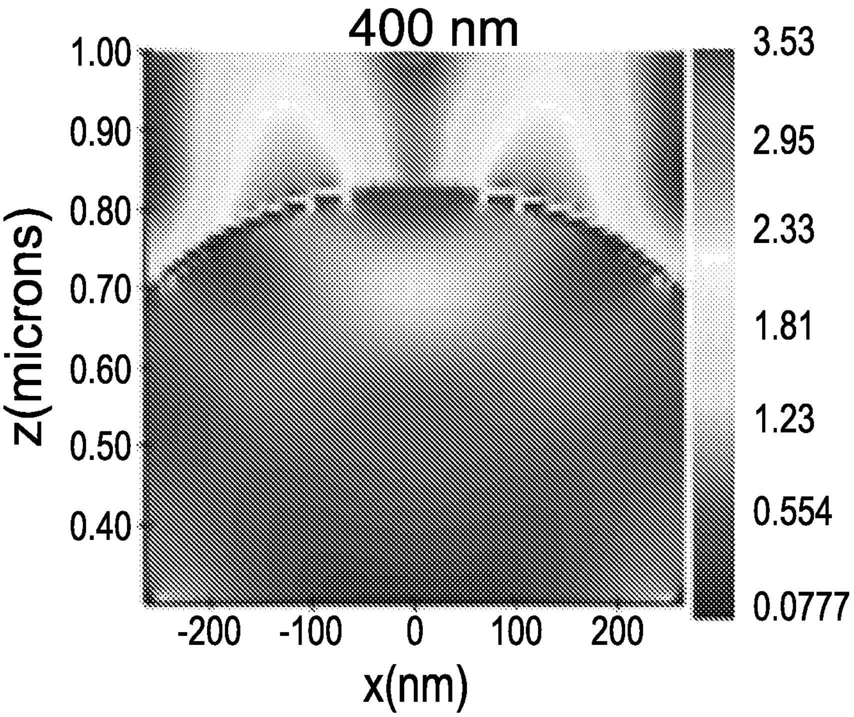
FIG. 7G shows the electric field distribution in nanocavities having a size of 400 nm.
Figure 7H:
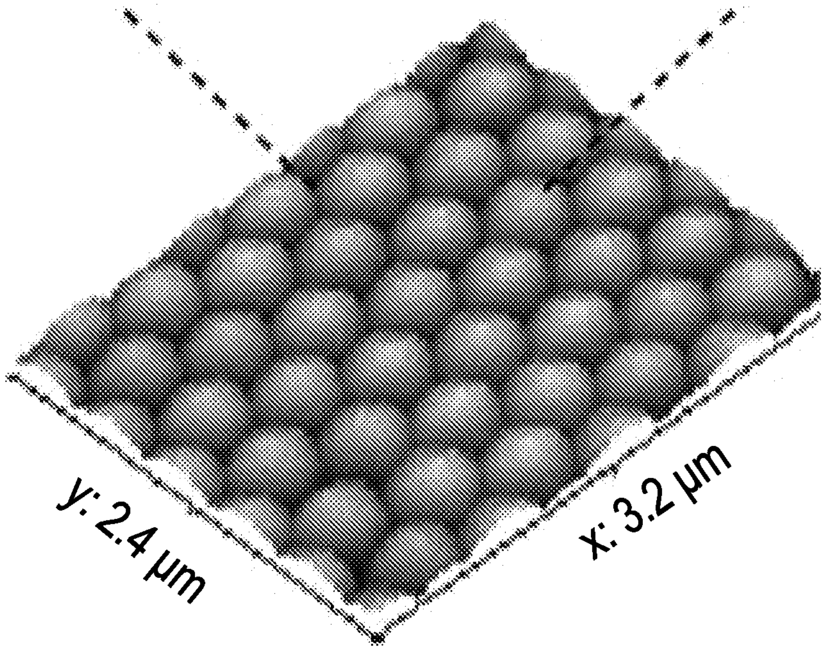
FIG. 7H is an AFM image of the nanocavities of FIG. 7G.
Figure 7I:
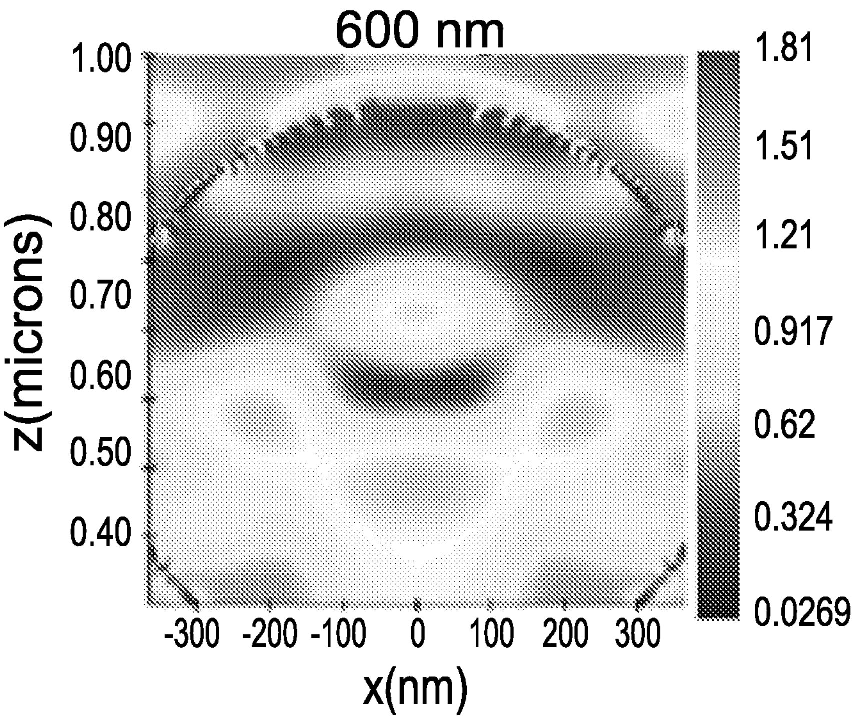
FIG. 7I shows the electric field distribution in nanocavities having a size of 600 nm.
Figure 7J:
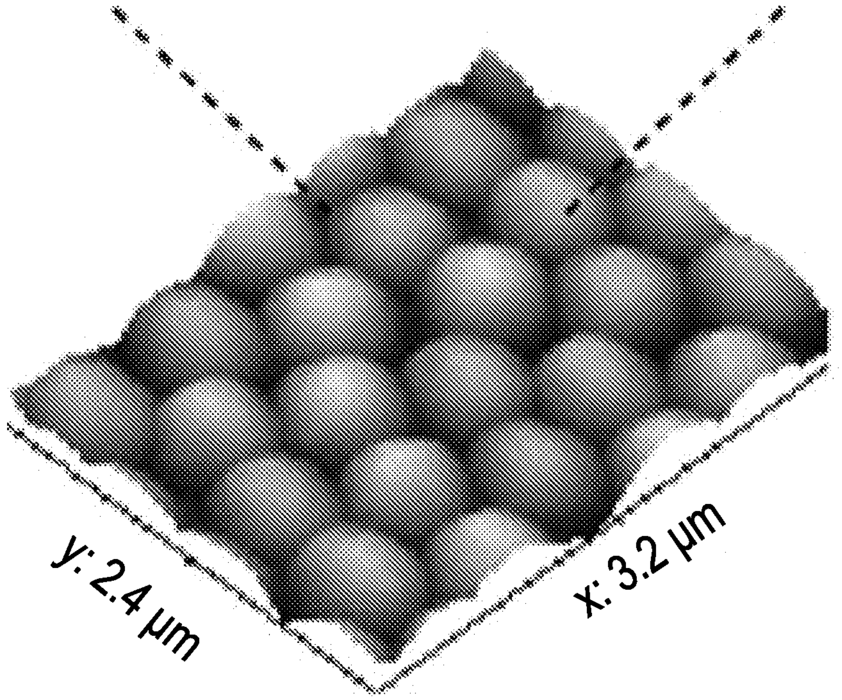
FIG. 7J is an AFM image of the nanocavities of FIG. 7I.
Figure 7K:
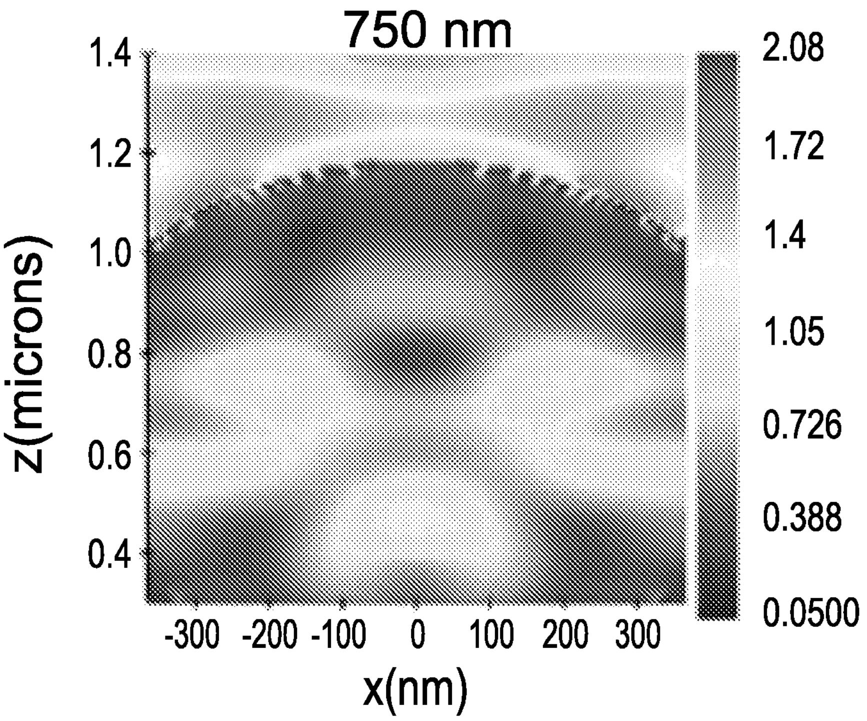
FIG. 7K shows the electric field distribution in nanocavities having a size of 750 nm.
Figure 7L:
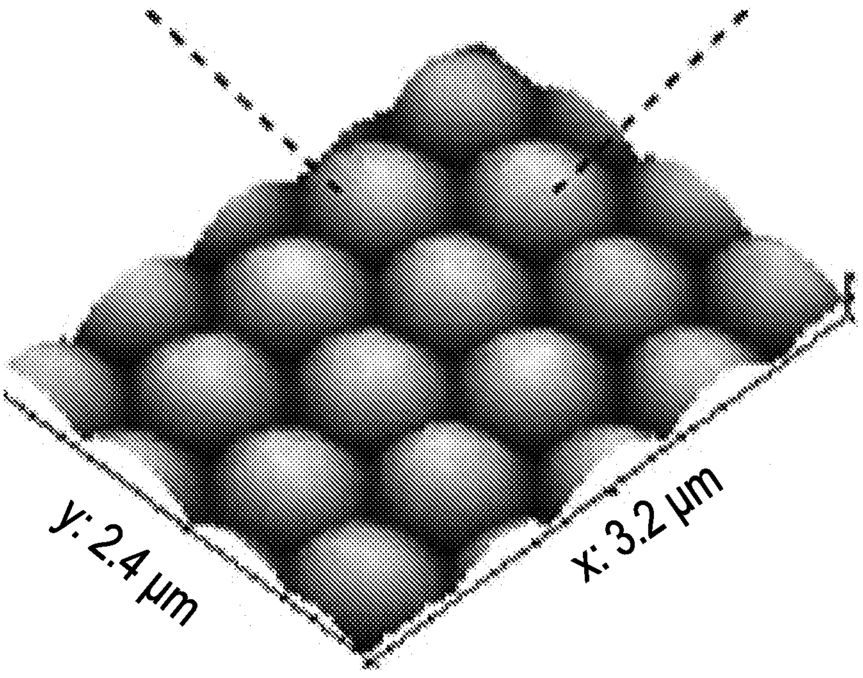
FIG. 7L is an AFM image of the nanocavities of FIG. 7K.

The conventional metric to study the superiority of the structure is the absorption efficiency which is the ratio of the absorption cross-section to the geometric cross-section. The absorption efficiency for a cylindrical particle illuminated along its axis is given by:

$$Q_{abs} = \frac{4\sigma_{abs}}{\pi d^2}$$

where d is the diameter of the nanoparticle and $\sigma_{abs}$ is the absorption cross-section which can be calculated with dividing the power absorbed by nanoparticle over the incident irradiance. Based on the absorption cross-section and the absorption efficiency for different sizes of nanoparticles the electric field distribution is changed on the plasmonic surface which can be simulated using the FDTD module of the LUMERICAL software package. To theoretically study the electric field of plasmonic platforms, a series of simulations were performed. The experimental and simulated broadband reflectance spectra (FIG. 7D) shown analogues spectra demonstrating a sharp absorption between 500-540 nm correlated to the diffraction mode. For polystyrene (PS) nanoparticles with a diameter larger than 250 nm the diffraction mode blueshifts when D increases, as governed by the dispersion characteristics of surface plasmon resonance (SPR). The peaks in the measured spectra were broader than the corresponding simulation results, likely due to ensemble averaging and higher scattering losses in the Al layer. FIGS. 7E, 7G, 7I, and 7K show the 2D color map of the electric field distribution as a function of self-assembly nanoparticles diameter (D). The electric field distribution was simulated in the plane-wave excitation with a wavelength of 380 nm-720 nm for D varying from (i) 200, (ii) 400 nm, (iii) 600 nm (iv) 750 nm with the correlated AFM images of the fabricated plasmonic platforms, respectively FIGS. 7F, 7H, 7J and 7L. The higher intensity of the electric field dispersion when D=400 nm demonstrated that 400 nm is likely the ideal size to achieve the strong SPR effect for color-sensitive projection.

Figure 8A:
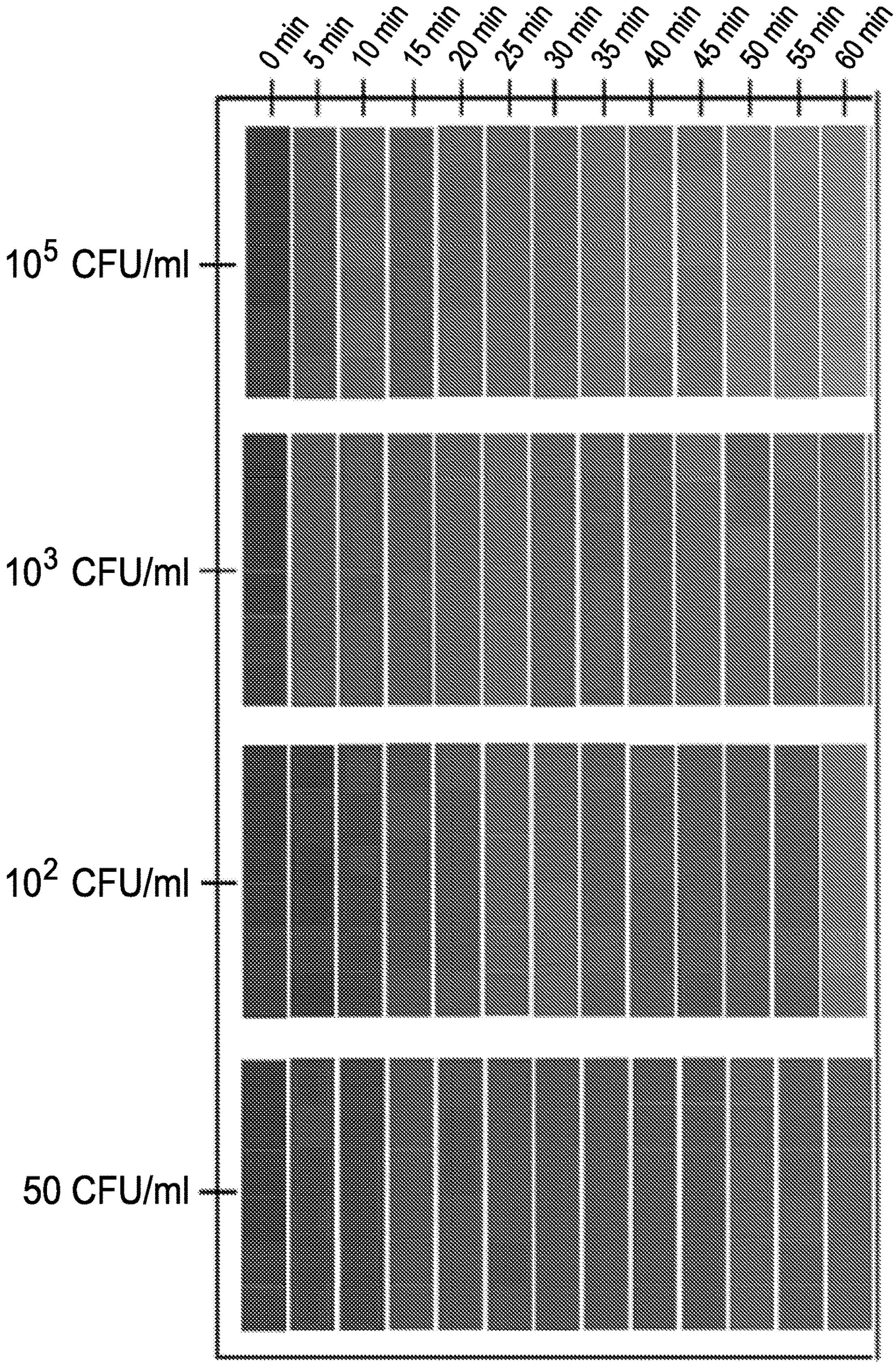
FIG. 8A shows a color response of a 400 nm platform in media of $5\times10^5$ CFU/ml, 103 CFU/ml, $10^2$ CFU/ml, 50 CFU/ml concentrations of Ampicillin-resistant *Escherichia coli* (*E. coli*) mixed with resazurin in presence of 100 μg/mL Ampicillin antibiotic, showing the resistance of bacteria against Ampicillin (color-change from navy blue to green). Each micrograph was collected within 5 minutes of culturing bacteria in corresponding media during one-hour of starting the culture.
Figure 8B:
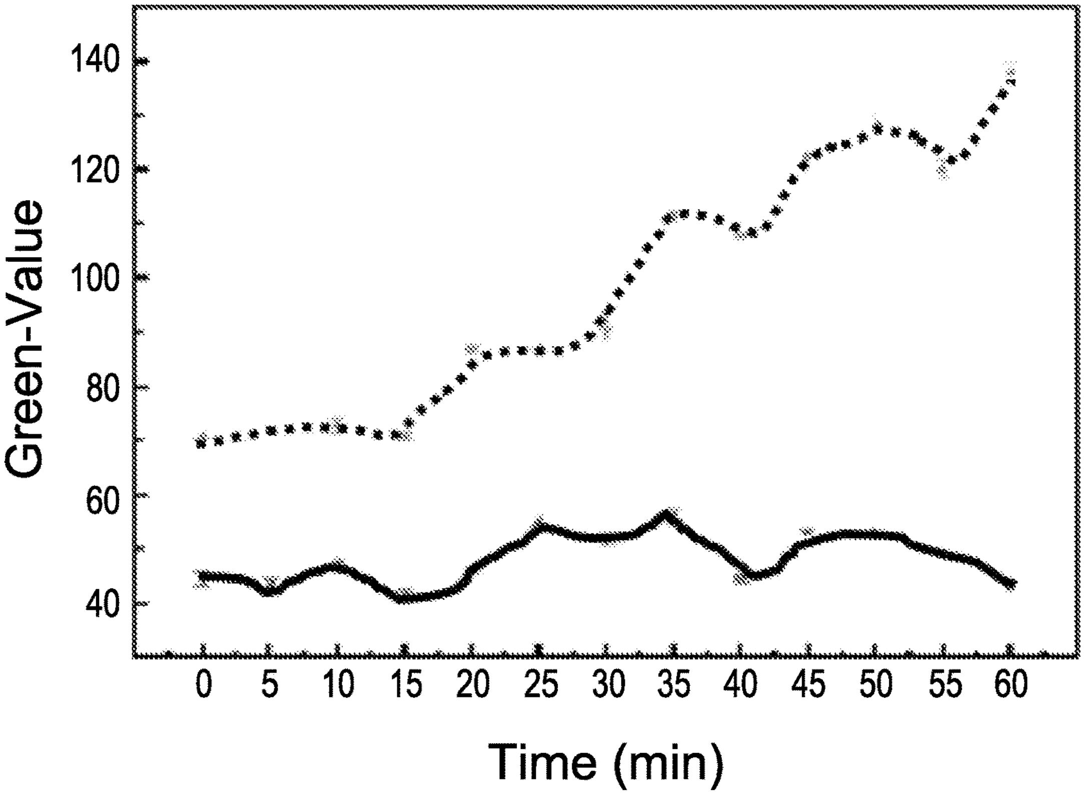
FIG. 8B is a plot of green value for ampicillin (resistant) and kanamycin (susceptible) treated Ampicillin-resistant *E. coli* ($10^5$ CFU/mL). The resistant (dashed line) exhibits an increase in the green value over the 1 hr incubation whereas the susceptible (solid line) exhibits a constant green value and lacks the color change associated with viable bacteria.
Figure 8C:
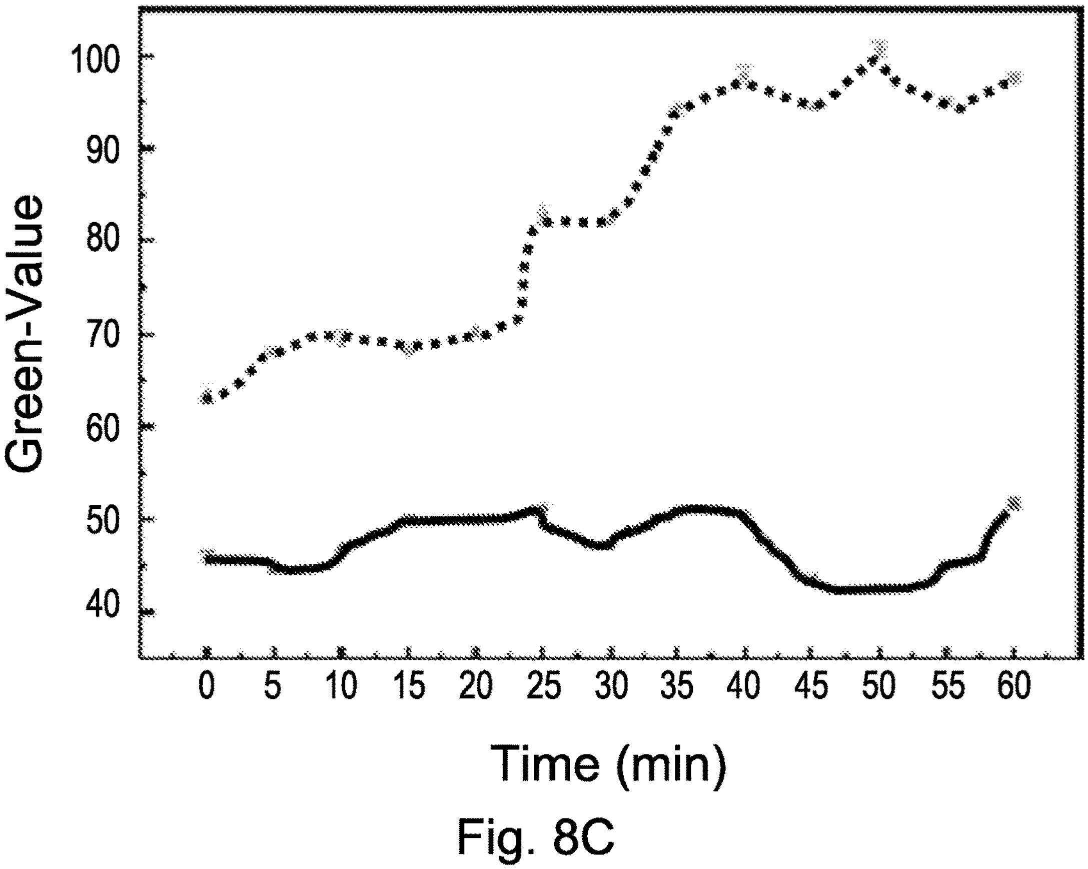
FIG. 8C is a plot of green value for ampicillin (resistant) and kanamycin (susceptible) treated Ampicillin-resistant *E. coli* ($10^3$ CFU/mL). The resistant (dashed line) exhibits an increase in the green value over the 1 hr incubation whereas the susceptible (solid line) exhibits a constant green value and lacks the color change associated with viable bacteria.
Figure 8D:
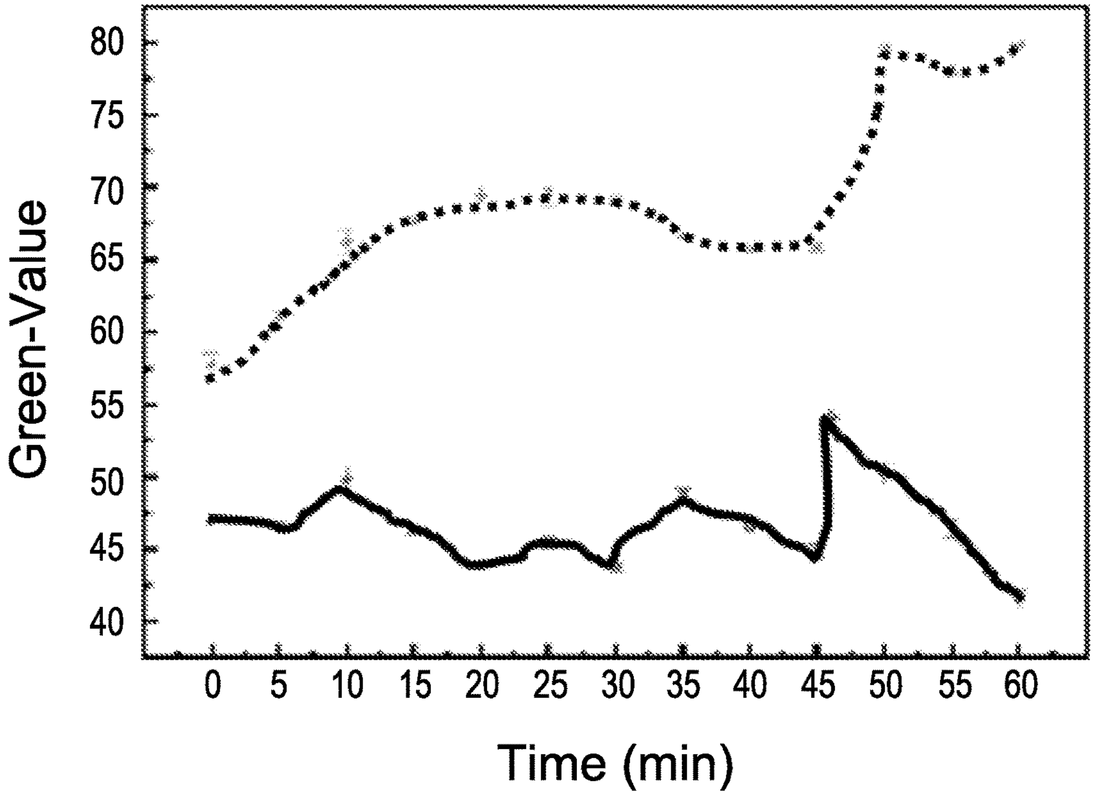
FIG. 8D is a plot of green value for ampicillin (resistant) and kanamycin (susceptible) treated Ampicillin-resistant *E. coli* ($10^2$ CFU/mL). The resistant (dashed line) exhibits an increase in the green value over the 1 hr incubation whereas the susceptible (solid line) exhibits a constant green value and lacks the color change associated with viable bacteria.
Figure 8E:
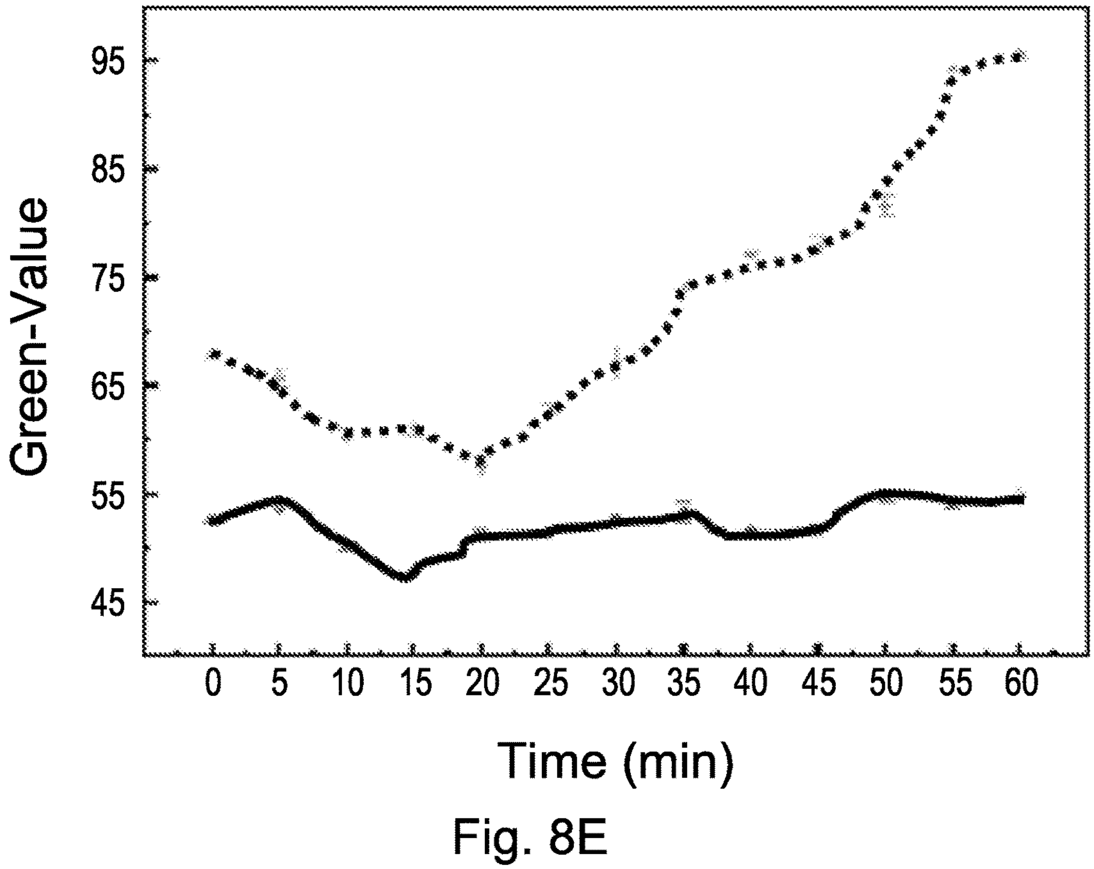
FIG. 8E is a plot of green value for ampicillin (resistant) and kanamycin (susceptible) treated Ampicillin-resistant *E. coli* (50 CFU/mL). The resistant (dashed line) exhibits an increase in the green value over the 1 hr incubation whereas the susceptible (solid line) exhibits a constant green value and lacks the color change associated with viable bacteria.
Figure 8F:
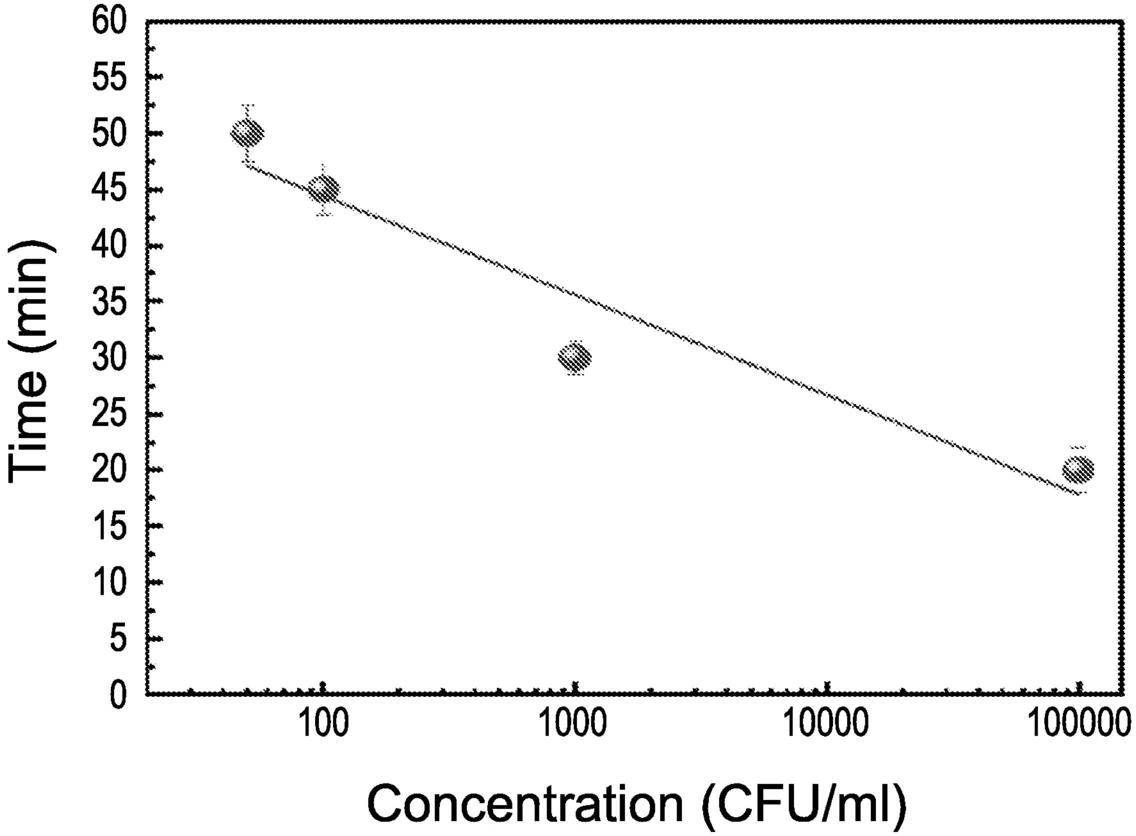
FIG. 8F is a plot of time of color change detection for different concentrations of Ampicillin-resistant *E. coli* mixed with resazurin in presence of 100 μg/mL ampicillin antibiotic. An inverse relation was established between the bacterial concentration and time of detection, where the color change was detected after 20 minutes and 50 minutes for concentrations of $10^5$ CFU/m and 50 CFU/mL respectively.

A study was conducted using the microfluidic chip to evaluate the antibiotic susceptibility profile of ampicillin-resistant *E. coli* for 100 µg/mL ampicillin (resistant) and 50 µg/mL kanamycin (susceptible). Different initial concentrations of ampicillin-resistant *E. coli* ($5\times10^5$ CFU/mL, $10^3$ CFU/mL, $10^2$ CFU/mL, and 50 CFU/mL) were challenged with the antibiotics and incubated for 1 hour at 37° C., the color change was monitored at 5-minute intervals. FIG. 8A shows full gamut change (blue to green) of the resistant aliquots over 1-hour incubation. In comparison, the susceptible aliquots did not exhibit color change due to the inhibition of *E. coli*. The green values for the resistant and susceptible aliquots of the same initial concentration are compared in FIGS. 8B-8E. Resistant aliquots showed 194%, 140%, 142%, and 131% increase in green value of the 1-hour incubated aliquots compared to the zero minute incubation aliquot for 5×$10^5$ CFU/mL, $10^3$ CFU/mL, $10^2$ CFU/mL, and 50 CFU/mL concentrations respectively whereas the susceptible aliquots had constant green values of 49.26±5.32 for 5×$10^5$ CFU/mL, 48.12±3.21 for $10^3$ CFU/mL, 47.28±1.93 for $10^2$ CFU/mL, and 46.15±2.56 50 CFU/mL throughout the 1-hour incubation and thus lacking color change associated with viable cells. The detection rapidity decreased by lowering the initial concentration of bacteria. The plasmonic platform identified the efficacy of antibiotics on the bacterial strain under 60 minutes. As shown in FIG. 8F color change for the $10^5$ CFU/mL resistant aliquots was detected after 20 minutes. Dark cyan color was observed as a result of resazurin reduction to resorufin indicating the resistant profile of the *E. coli* versus ampicillin. This is a significant advancement to the previously reported time in the literature 4 hours for $10^5$ CFU/ml bacteria concentration. For $10^3$ CFU/mL *E. coli* concentration after 30 minutes incubation, dark cyan color was observed signaling their resistant traits. Color change to dark cyan can be observed after 45 and 50-minute incubations for $10^2$ CFU/mL and 50 CFU/mL *E. coli* aliquots respectively.

Figure 8G:
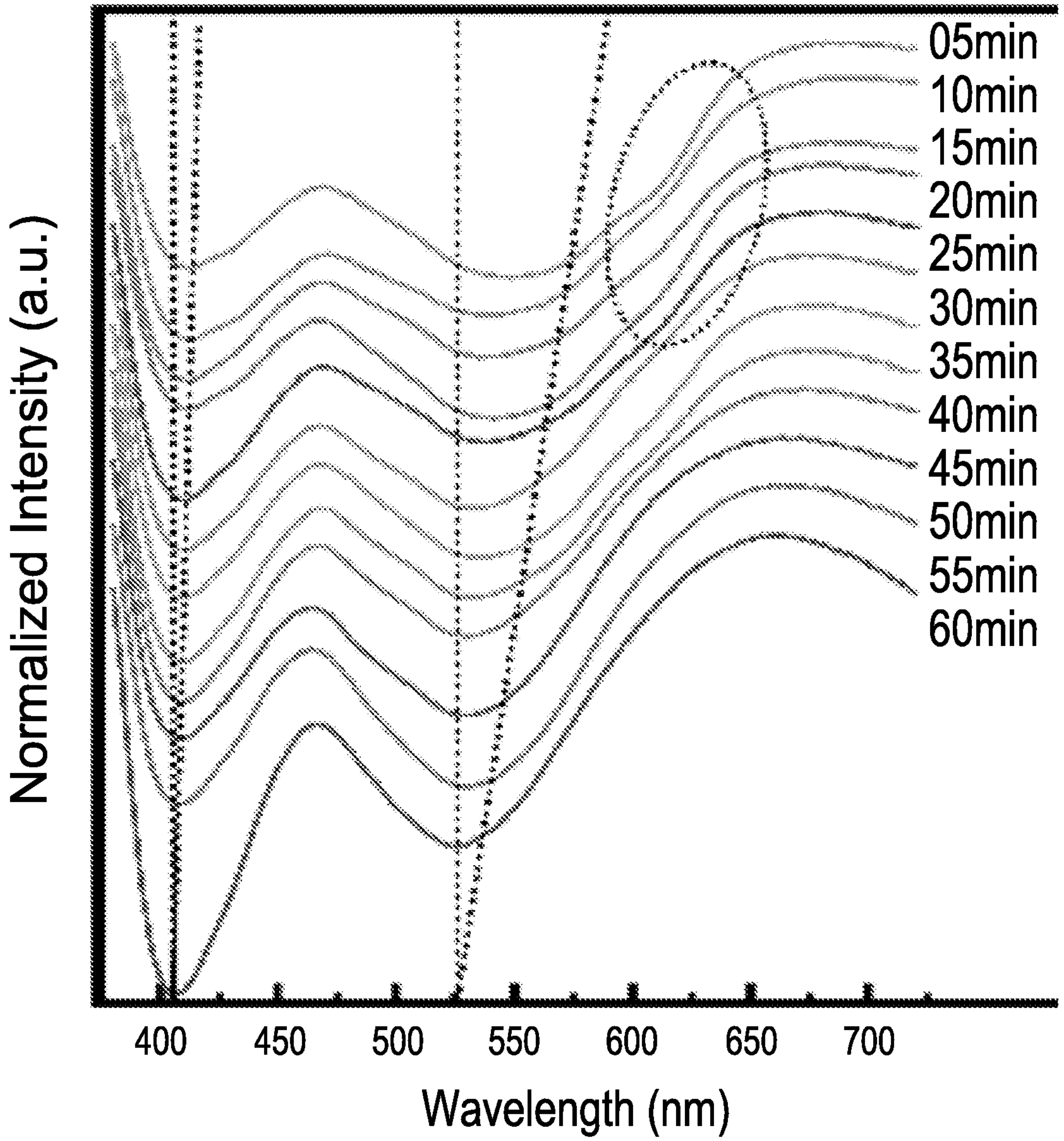
FIG. 8G is a reflectance spectra of 400 nm platform during resazurin reduction to resorufin.
Figure 8H:
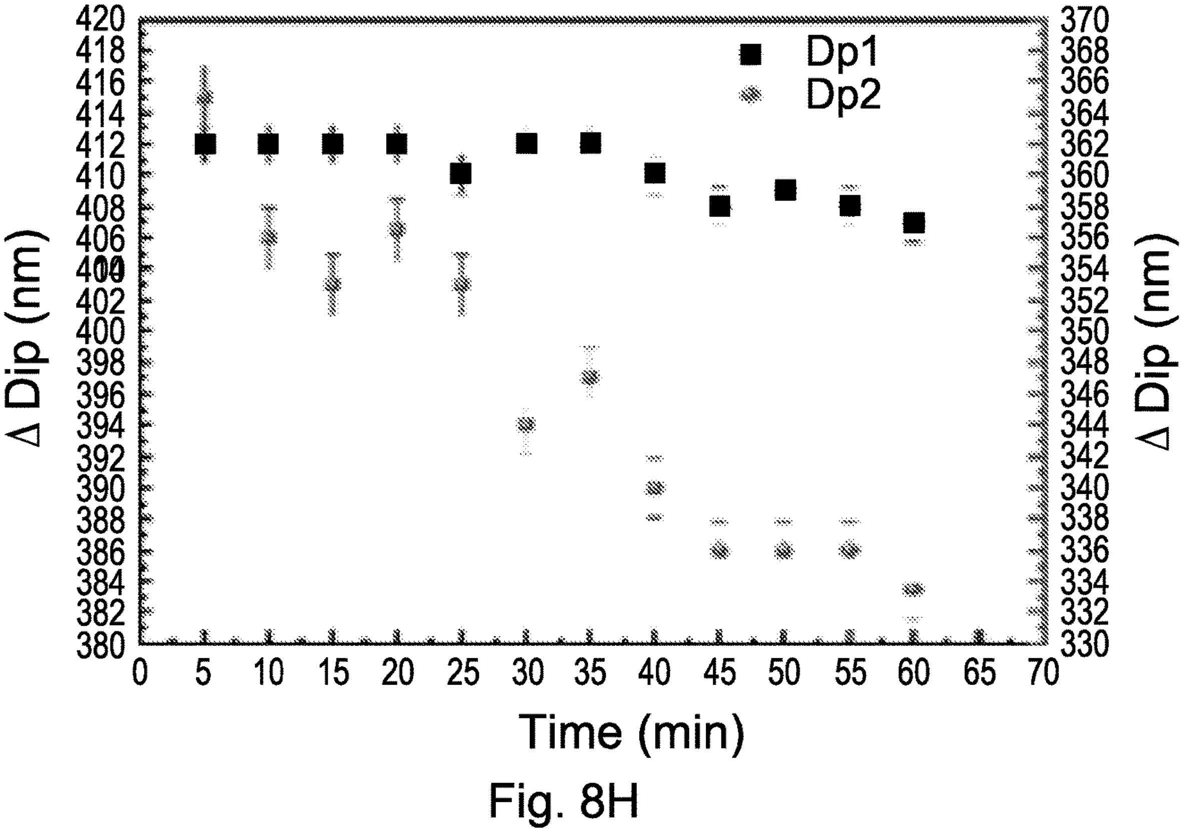
FIG. 8H is a graph showing the dip position for a 400 nm platform during resazurin reduction to resorufin.
Figure 8I:
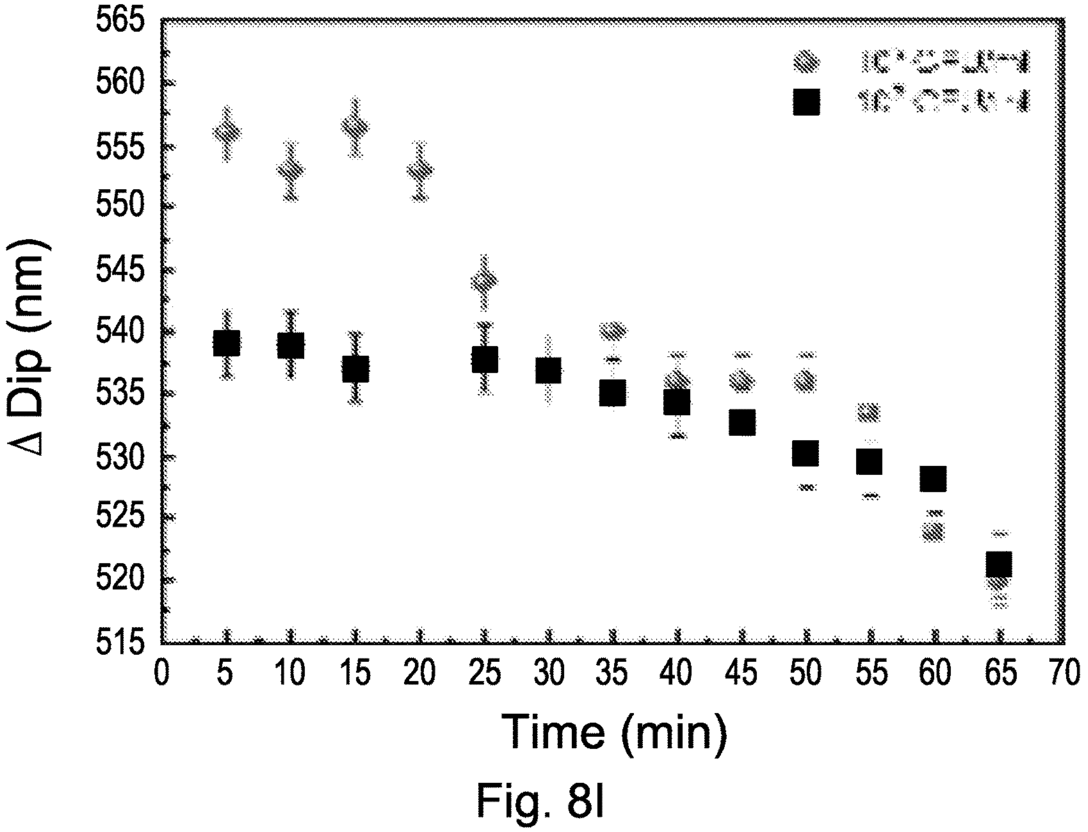
FIG. 8I is a graph showing the dip position during resazurin to resorufin reduction for $10^5$ CFU/mL (red) and $10^3$ CFU/ml (black).

FIG. 8G shows experimental reflectance spectra for the 400 nm plasmonic nanosurface performed in water-based media. The origin of the different resonances can be attributed to the two-fold role of the plasmonic structures. Local resonances are responsible for color shifts. Localized surface plasmon resonance (LSPR) given by dipolar coupling between adjacent structures and surface plasmon resonance (SPR) from the structured array gave rise to hot-spots regions located by the space given by the cavity length and space in between structures, also known as nanocavity. In the present chip, the periodic bumps formed by nanoparticles 605*c*, 605*c*', 605*c*" acted as coupling elements to excite propagating surface plasmons (SPs) on the surface 105*p*. Since the Al layer 605*a*, 605' was ultrathin, these SPs were coupled to the top metallic-liquid interface. The light reradiated from those coupled plasmons interfered with the directly reflected light and generated resonance dips in the reflection spectrum. At shorter wavelengths, a sharp reflectance dip is expected to translate the lattice resonance. Opposite, at longer wavelengths the dips attributed to high-order mode are expected to be broader. The penetrated propagating SP modes were subjected to alteration by changing the refractive index (RI) of the medium. The additional informetric dip correlated to resazurin media was demonstrated by a dotted line. For the color-sensitive sensing application described herein, the second spectral feature (dip) was chosen as it had shown the best sensitivity towards the changes in the refractive index of the liquid media (FIG. 8H). The high order mode dip exhibited a blue shift along with the reduction of resazurin to resorufin. FIG. 8I compares the higher-order mode dip shift overtime for $10^5$ CFU/mL and $10^3$ CFU/mL. The $10^5$ CFU/mL exhibited a larger high-order mode dip shift (ΔDip=36 nm) compared to the $10^3$ CFU/mL (ΔDip=15 nm) indicating a more pronounced color change.

Figure 9A:
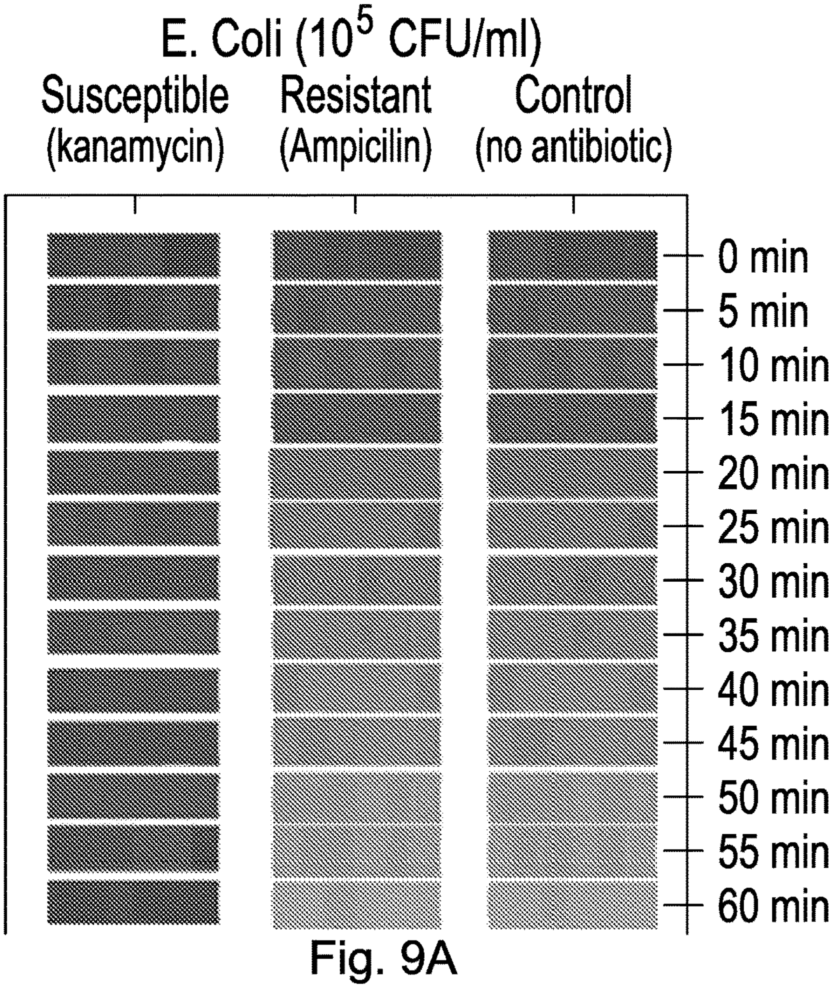
FIG. 9A is a color response of a 400 nm platform in media of $5\times10^5$ CFU/ml concentrations of Ampicillin-resistant *E. coli* mixed with resazurin in presence of Ampicillin, Kanamycin, and no antibiotics (control), showing the resistance of bacteria against Ampicillin (color-change from navy blue to green) and their susceptibility against Kanamycin (no color-change). Each micrograph was collected within 5 minutes of culturing bacteria in corresponding media during one-hour of starting the culture.
Figure 9B:
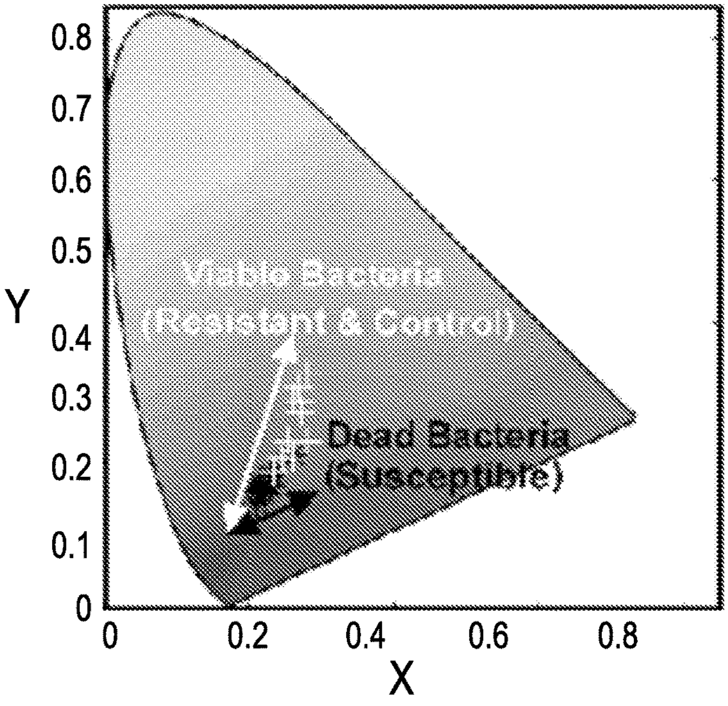
FIG. 9B is a 2D CIE chromaticity diagram showing the rate of change in color for control, resistant, and susceptible cases of FIG. 9A.
Figure 9C:
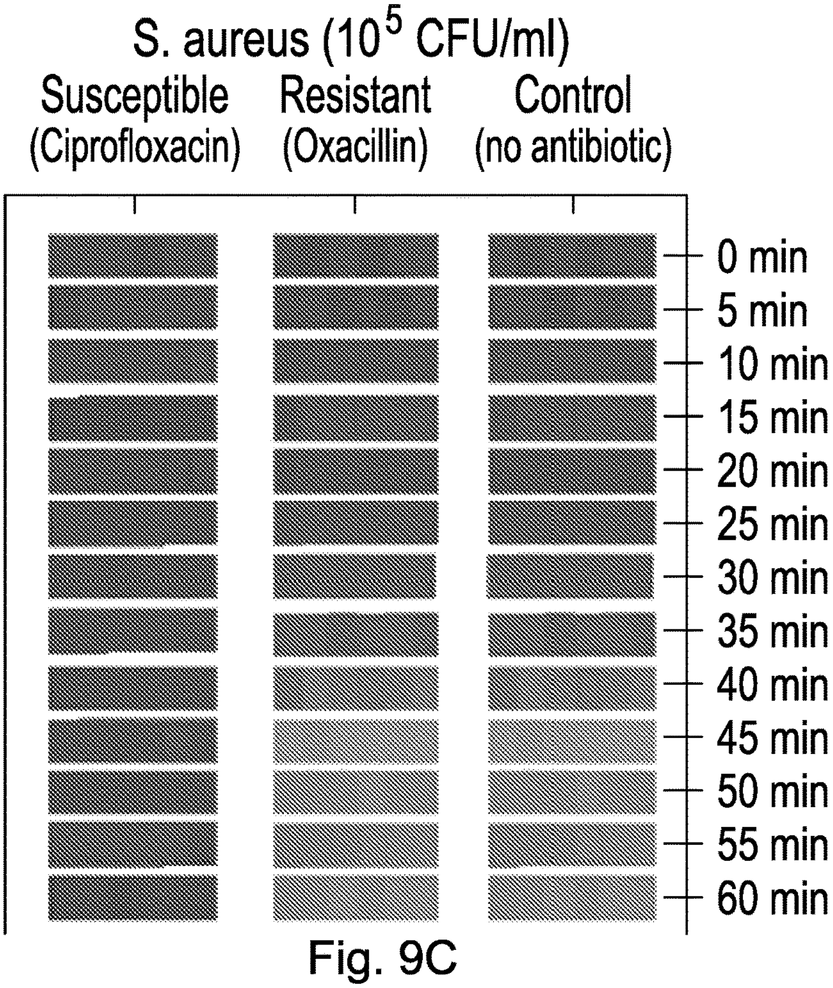
FIG. 9C is a color-response of green expression for $5\times10^5$ CFU/ml of Oxacillin-resistant *Staphylococcus aureus* bacteria in the presence of Oxacillin (resistant), Ciprofloxacin (Cipro) (susceptible) and no antibiotics (control).
Figure 9D:
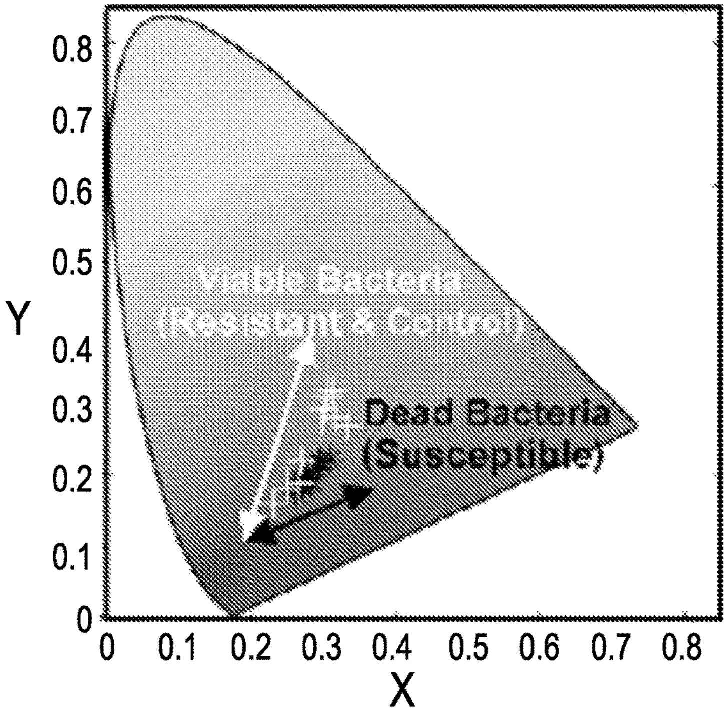
FIG. 9D is a 2D CIE chromaticity diagram profile for the Oxacillin (resistant), Ciprofloxacin (Cipro) (susceptible) and no antibiotics (control) conditions of FIG. 9C.
Figure 9E:
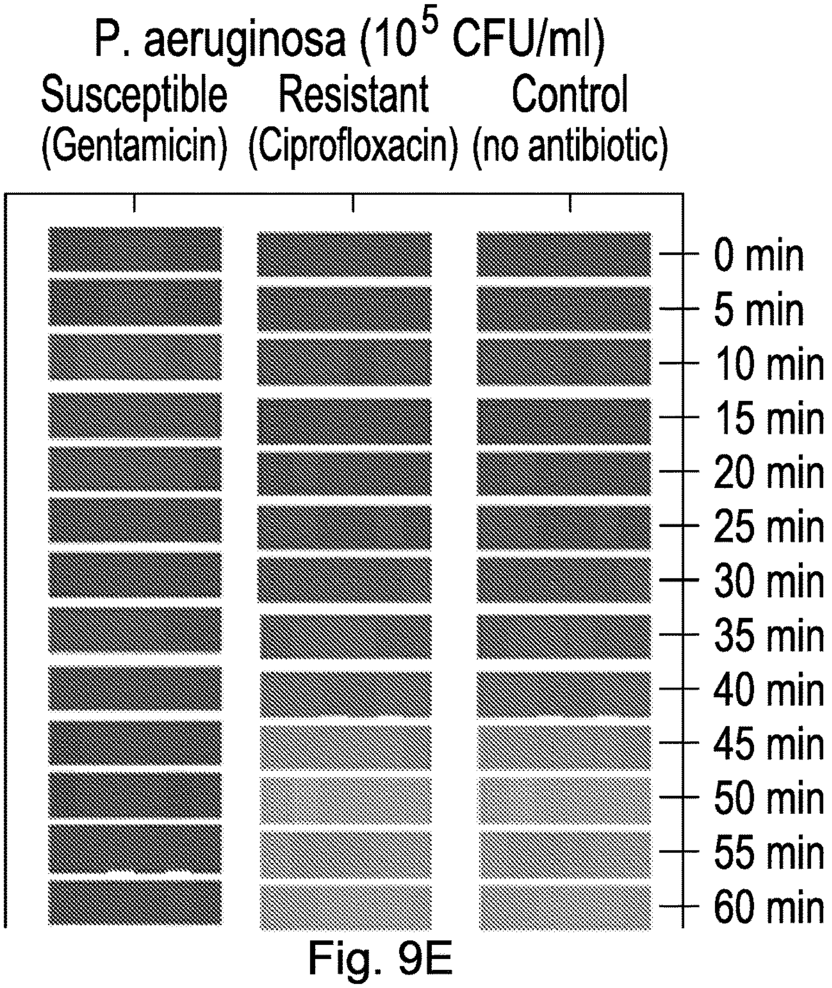
FIG. 9E is a color-response of green expression for $5\times10^5$ CFU/ml of Ciprofloxacin-resistant *Pseudomonas. aeruginosa* (PA) bacteria in presence of Ciprofloxacin (resistant), Gentamicin (susceptible), and no antibiotics (control).
Figure 9F:
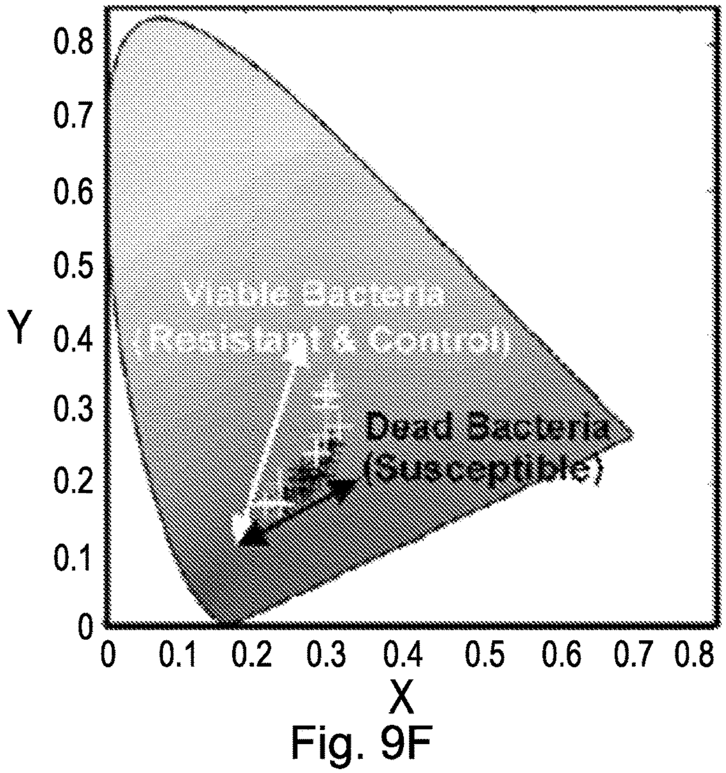
FIG. 9F is a 2D CIE chromaticity diagram profile for the Oxacillin (resistant), Ciprofloxacin (Cipro) (susceptible) and no antibiotics (control) conditions of FIG. 9E.
Figure 9G:
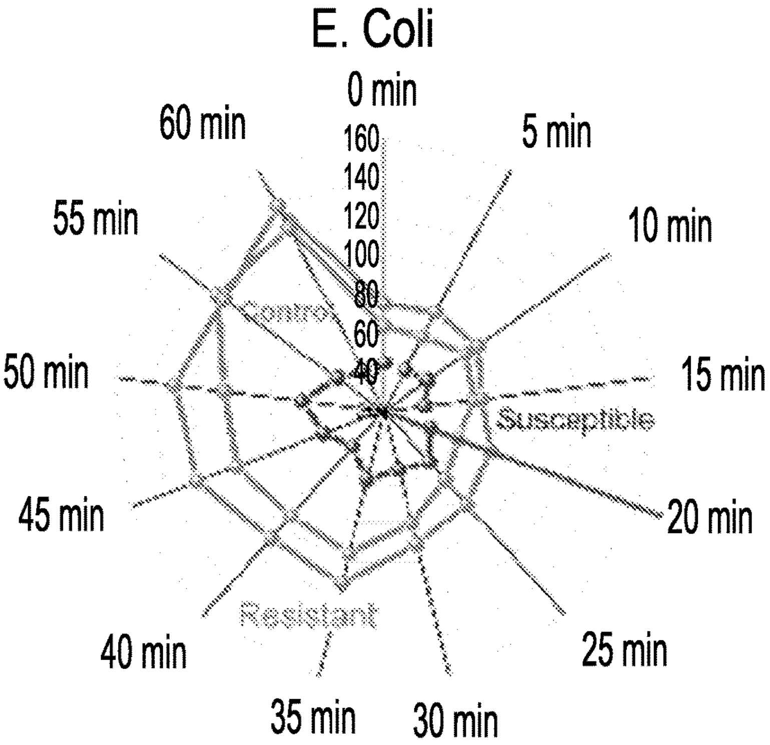
FIG. 9G shows web plots comparing the profile of green expression for control, resistant and susceptible samples of Ampicillin-resistant *E. coli*. The expansion in green expression is correlated to the time that the resistivity of bacteria against antibiotics is conceived. Each point on the web plot is the mean value derived from 30 random points.
Figure 9H:
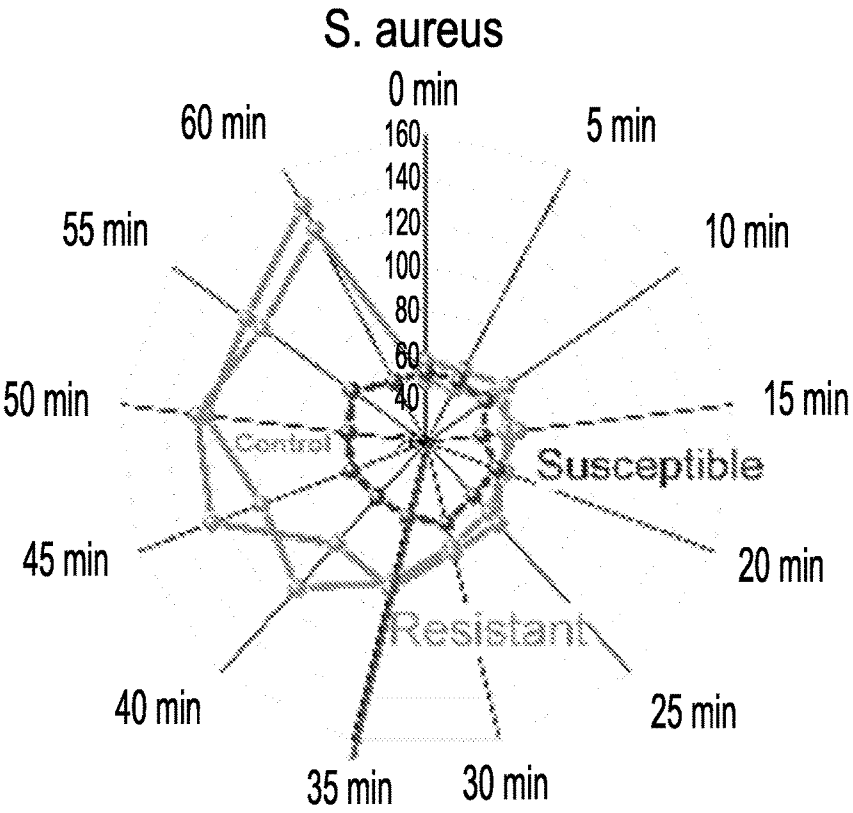
FIG. 9H shows web plots comparing the profile of green expression for control, resistant and susceptible samples of Oxacillin-resistant *S. aureus*. The expansion in green expression is correlated to the time that the resistivity of bacteria against antibiotics is conceived. Each point on the web plot is the mean value derived from 30 random points.
Figure 9I:
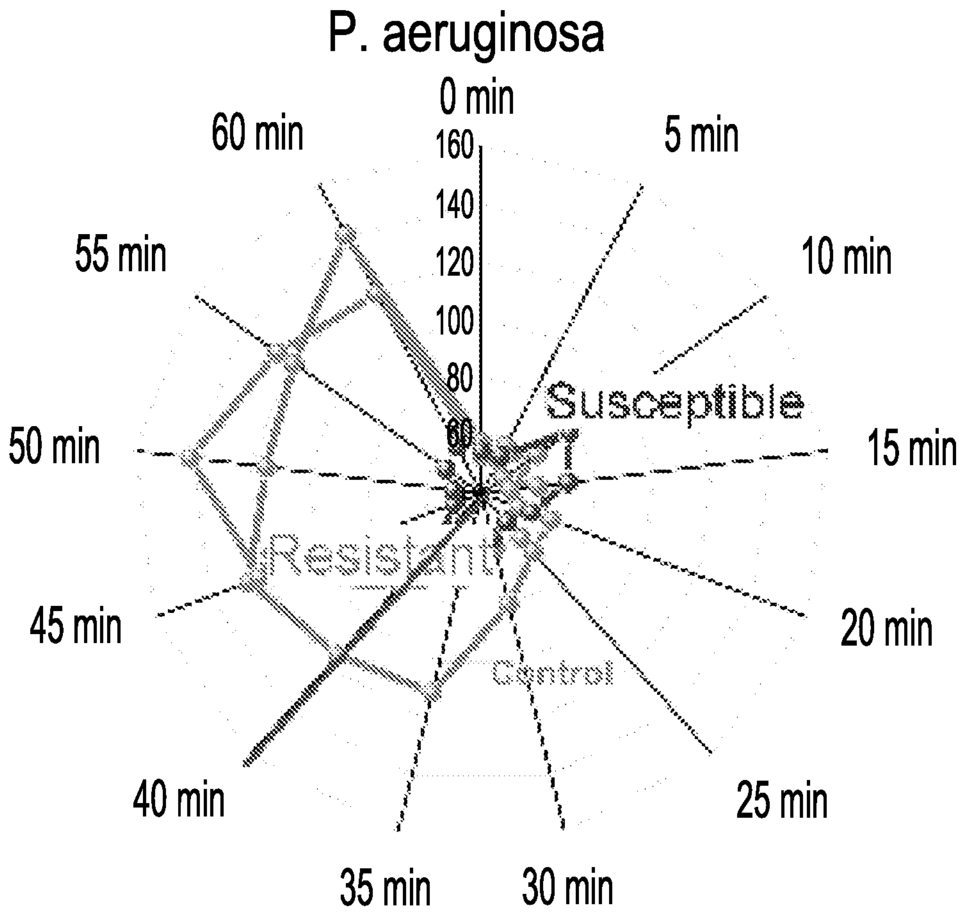
FIG. 9I shows web plots comparing the profile of green expression for control, resistant and susceptible samples of Ciprofloxacin-resistant *P. aeruginosa* bacteria. The expansion in green expression is correlated to the time that the resistivity of bacteria against antibiotics is conceived. Each point on the web plot is the mean value derived from 30 random points.
Figure 9J:
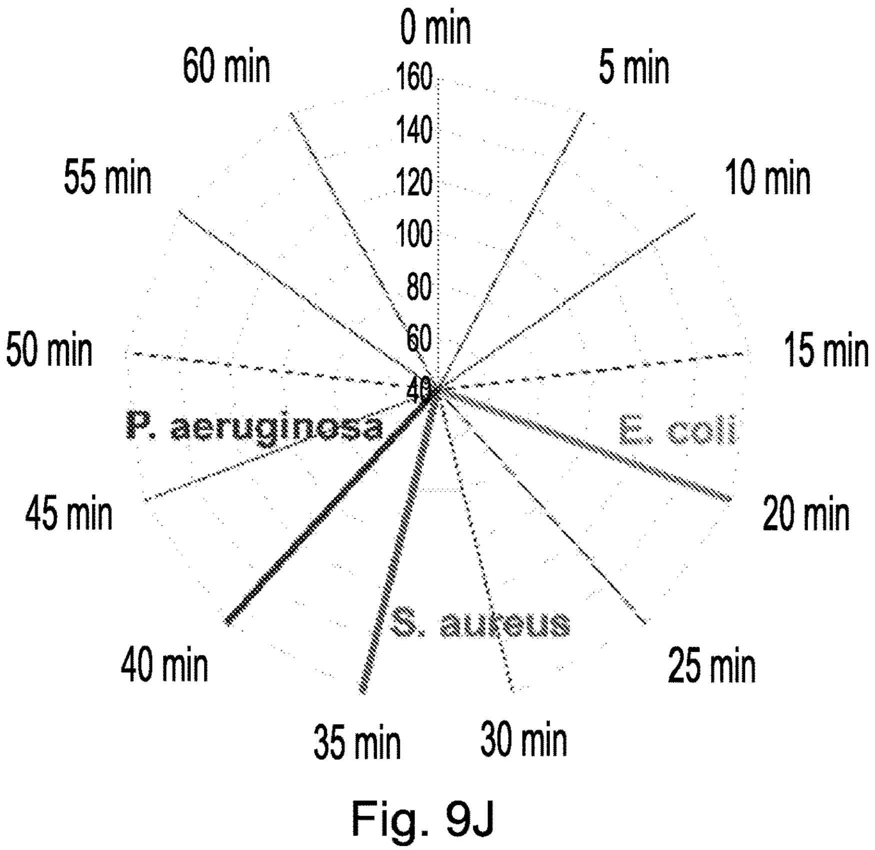
FIG. 9J is a comparison of time of plasmonic-enhanced color change detection for Ampicillin-resistant *E. coli*, Oxacillin-resistant *S. aureus*, and Ciprofloxacin-resistant *P. aeruginosa* bacteria which is 20 minutes, 35 minutes and 40 minutes respectively.
Figure 9K:
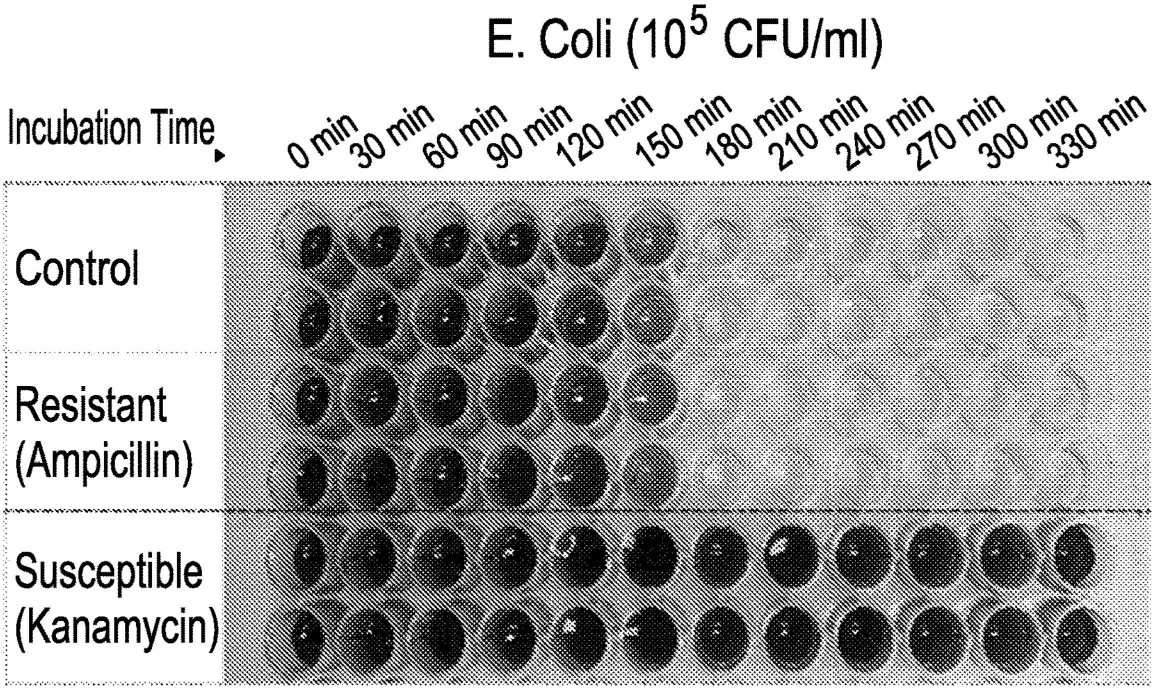
FIG. 9K is a non-plasmonic enhanced color detection of antibiotic susceptibility of 5×105 CFU/ml concentrations of Ampicillin-resistant *E. coli* mixed with resazurin in presence of Ampicillin, Kanamycin, and no antibiotics (control). Color change in control and resistant samples was detected after 180 minutes comparing to 20 minutes for plasmonic enhanced color detection.

An antibiotic susceptibility profiling study for 5×$10^5$ CFU/mL initial concentration aliquots of Amp. Resistant *E. coli*, MRSA, and Cipro. Resistant PA was conducted. Each strain was prepared in 3 aliquot sets, control with no antibiotic, Resistant (100 μg/mL Ampicillin, 4 ug/mL Oxacillin, and 2 ug/mL Ciprofloxacin for Amp. Resistant *E. coli*, MRSA, and Cipro. Resistant PA respectively), and Susceptible (50 μg/mL Kanamycin, 1 ug/mL Ciprofloxacin, and 4 ug/mL Gentamicin for Amp. Resistant *E. coli*, MRSA, and Cipro.Resistant PA respectively). As shown in FIGS. 9A-9C both control and resistant aliquot sets exhibited color change from initial dark blue to green over the course of 1-hour incubation indicative of resazurin reduction and presence of viable bacterial cells. In contrast, the susceptible aliquot sets exhibited a constant dark blue color indicating the effectiveness of kanamycin, ciprofloxacin, and gentamicin in killing their respective bacterial strains. The 2D chromaticity diagrams presented the change to a brighter green color exhibited by control and resistant aliquots (white arrow) as shown by the increase of their y values (0.19 to 0.33 for Amp. Resistant *E. coli,* 0.16 to 0.33 for MRSA, and 0.175 to 0.34 for Cipro.Resistant PA). In comparison, the susceptible aliquot dots remained in the dark blue/purple region as indicated by the black arrows. FIG. 9D compares the green values of the control, resistant, and susceptible aliquot sets of the respective bacteria. A similar increase in green value trend is shown by both the control and resistant sets indicating the ineffectively of ampicillin, oxacillin, and ciprofloxacin against their respective strains. Detection of color change depended on bacterial strain. As shown in FIG. 9E Amp. Resistant *E. coli* exhibited the shortest detection time of 20 minutes followed by MRSA (35 minutes) and Cipro. Resistant PA (40 minutes). The chip 100, 100', 400, 400', 400" thus achieved 9× faster detection (20 minutes versus 180 minutes) of color change compared to the optical detection of resazurin reduction assay (FIG. 9F).

Figure 10A:
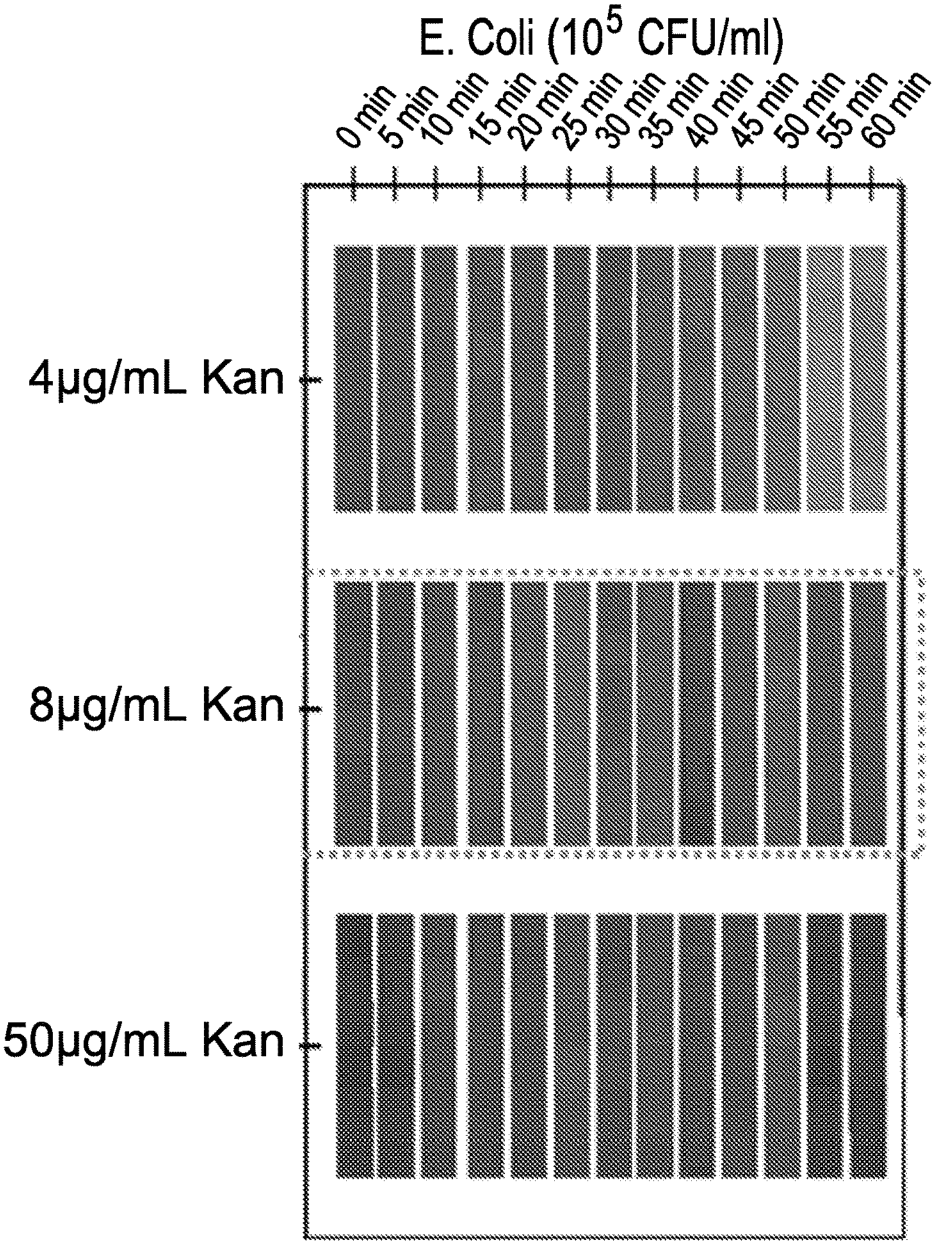
FIG. 10A is a platform color response for aliquots of $5\times10^5$ CFU/mL Amp resistant *E. coli* incubated at 37° C. incubated for different time durations from 0 minutes to 60 minutes with resazurin and different concentrations of Kanamycin (4 μg/mL, 8 μg/mL and 50 μg/mL).
Figure 10B:
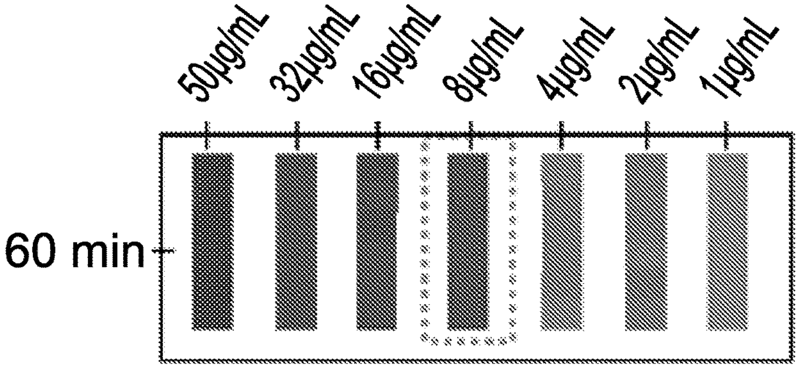
FIG. 10B is a color response of a 400 nm plasmonic platform using aliquots of $5\times10^5$ CFU/mL Amp resistant *E. coli* incubated at 37° C. for 60 minutes with resazurin and different concentrations of kanamycin (1 μg/mL, 2 μg/mL, 4 μg/mL, 8 μg/mL, 16 μg/mL, 32 μg/mL, and 50 μg/mL). The 1 μg/mL, 2 μg/mL, and 4 μg/mL, kanamycin doses were not enough to fully inhibit the *E. coli* metabolism as shown by the color change witnessed from purple to cyan.
Figure 10C:
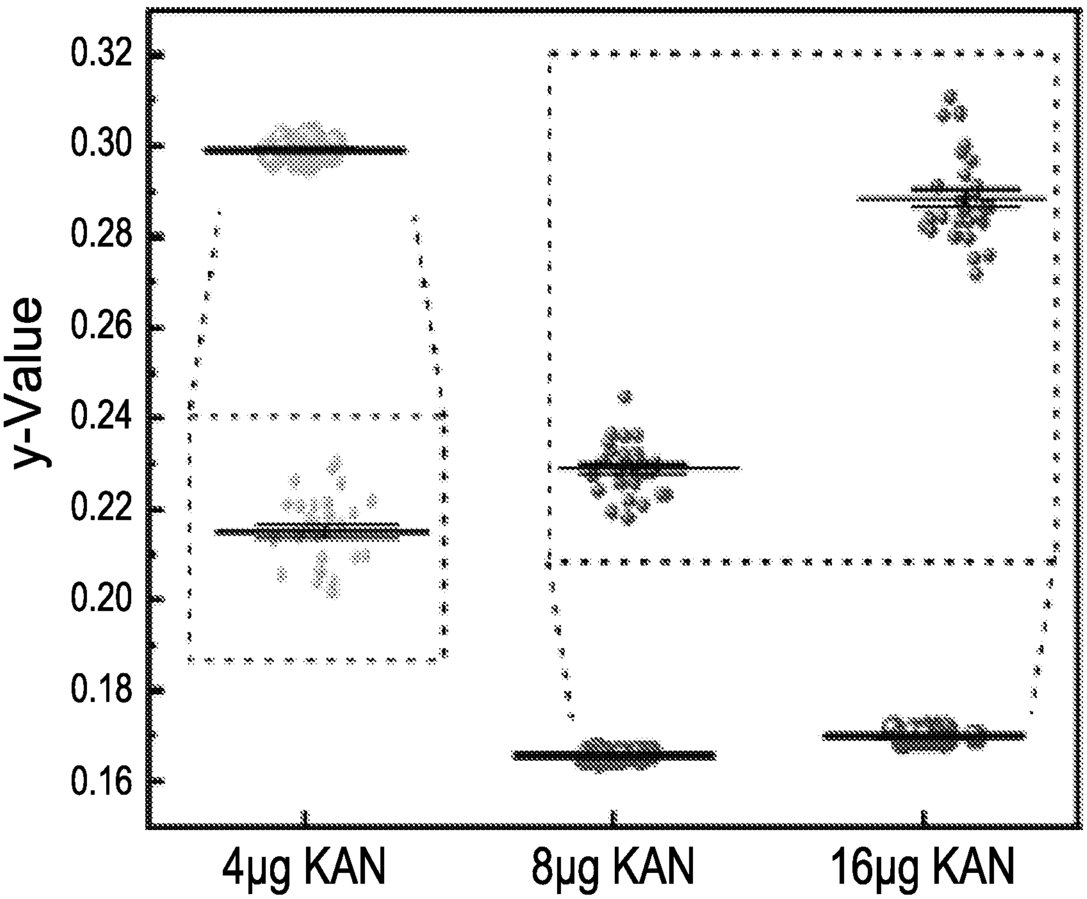
FIG. 10C is a y-value distribution of 60 minutes incubated aliquots of $5\times10^5$ CFU/mL Amp resistant *E. coli* mixed with resazurin and (4 μg/mL, 8 μg/mL, and 16 μg/mL). The 4 μg/mL kanamycin aliquot have a higher y-value (0.3) compared to 8 μg/mL and 16 μg/mL aliquots (0.125 and 0.175 respectively) indicating resistant bacteria. Thus, the MIC for Amp resistant *E. coli* is 8 μg/mL.
Figure 10D:
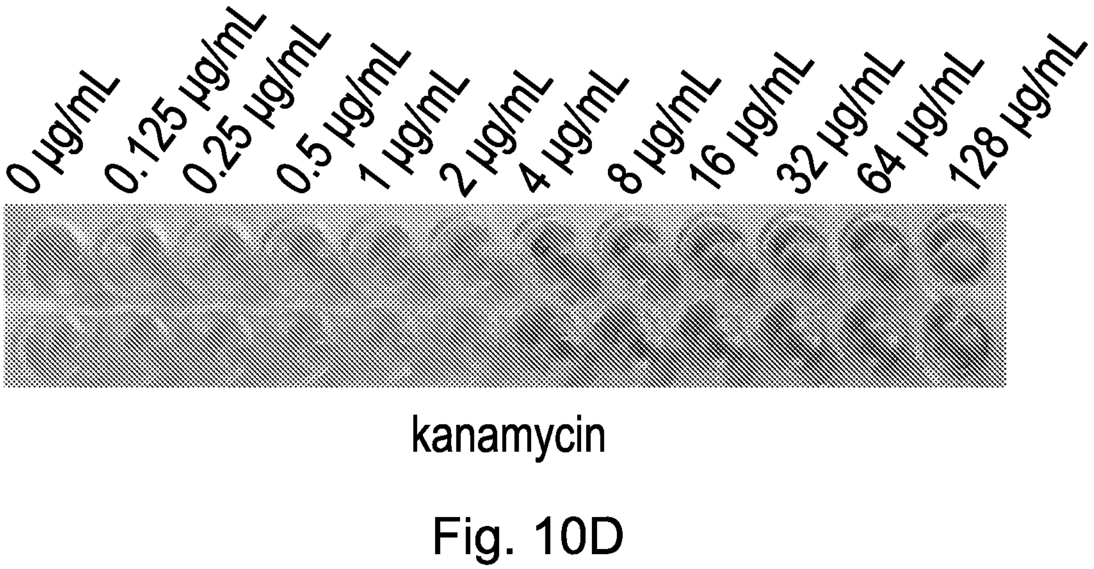
FIG. 10D shows a standard MIC assay using CLSI protocols confirming the obtained MIC in FIG. 10C (within acceptable two-fold variation).
Figure 10E:
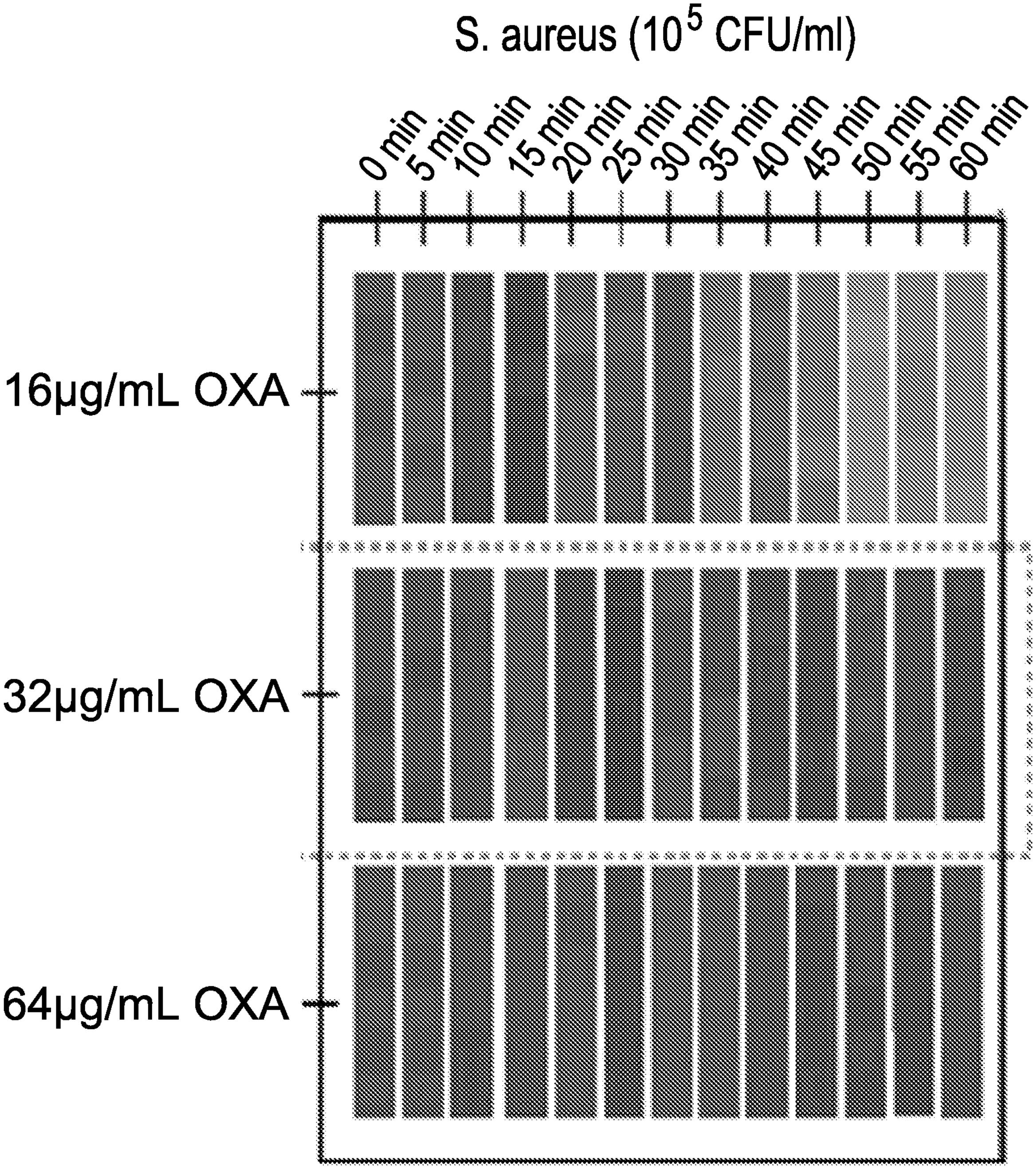
FIG. 10E shows a platform color response for aliquots of $5\times10^5$ CFU/mL methicillin resistant *Staphylococcus aureus* (MRSA) incubated at 37° C. incubated for different time durations from 0 minutes to 60 minutes with resazurin and different concentrations of Oxacillin (16 μg/mL, 32 μg/mL and 64 μg/mL). The 16 μg/mL Oxacillin dose was not enough to fully inhibit the MRSA metabolism as shown by the color change witnessed from purple to cyan.
Figure 10F:
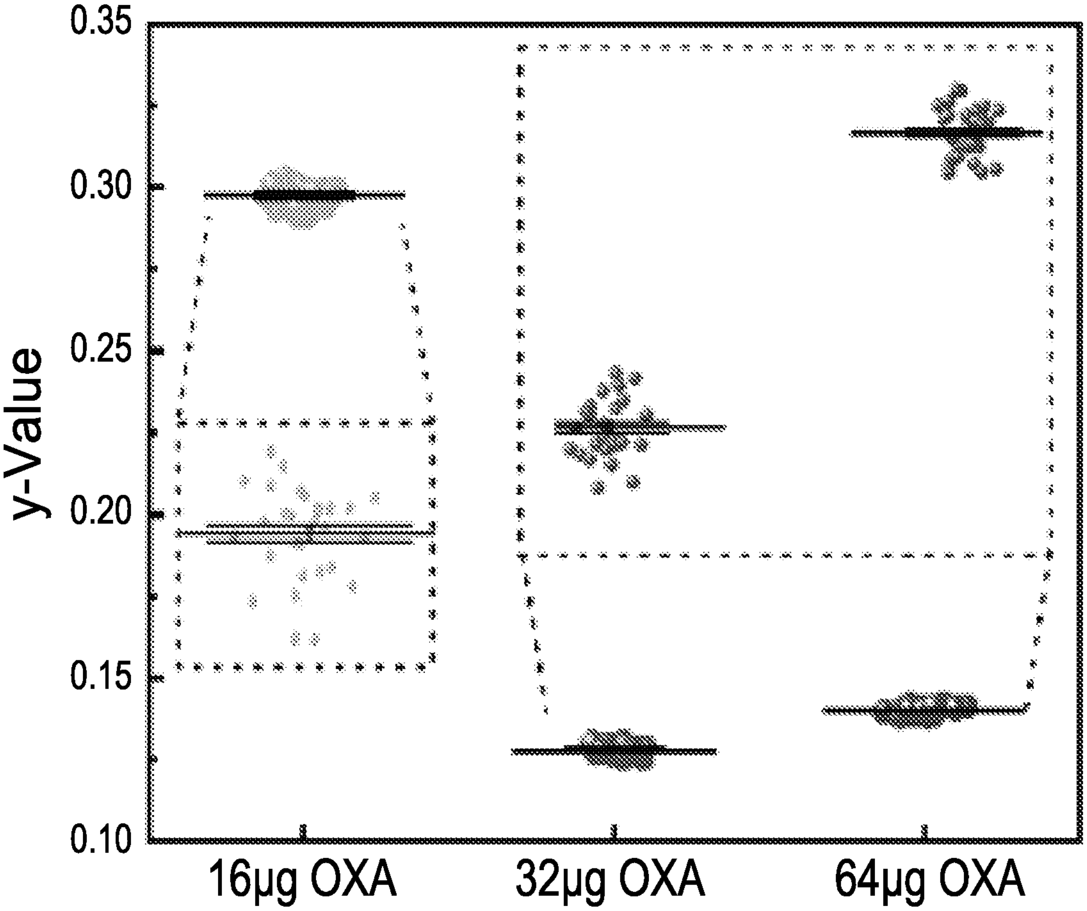
FIG. 10F is a y-value distribution of 60 minutes incubated aliquots of $5\times10^5$ CFU/mL MRSA mixed with resazurin and (16 μg/mL, 32 μg/mL, and 64 μg/mL) Oxacillin. 16 μg/mL Oxacillin aliquot have a higher y-value (0.3) compared to 32 μg/mL and 64 μg/mL aliquots (0.125 and 0.13 respectively) indicating resistant bacteria. Thus, the MIC for MRSA is 32 μg/mL. Standard MIC assay using CLSI protocols confirming the obtained MIC by the chip.
Figure 10G:
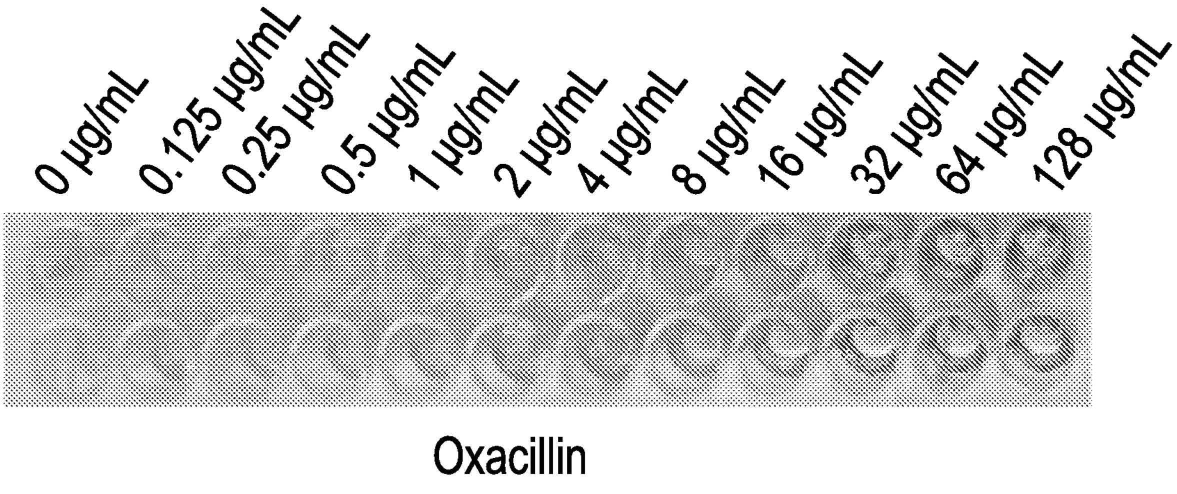
FIG. 10G shows a standard MIC assay using CLSI protocols confirming the obtained MIC in FIG. 10F (within acceptable two-fold variation).
Figure 10H:
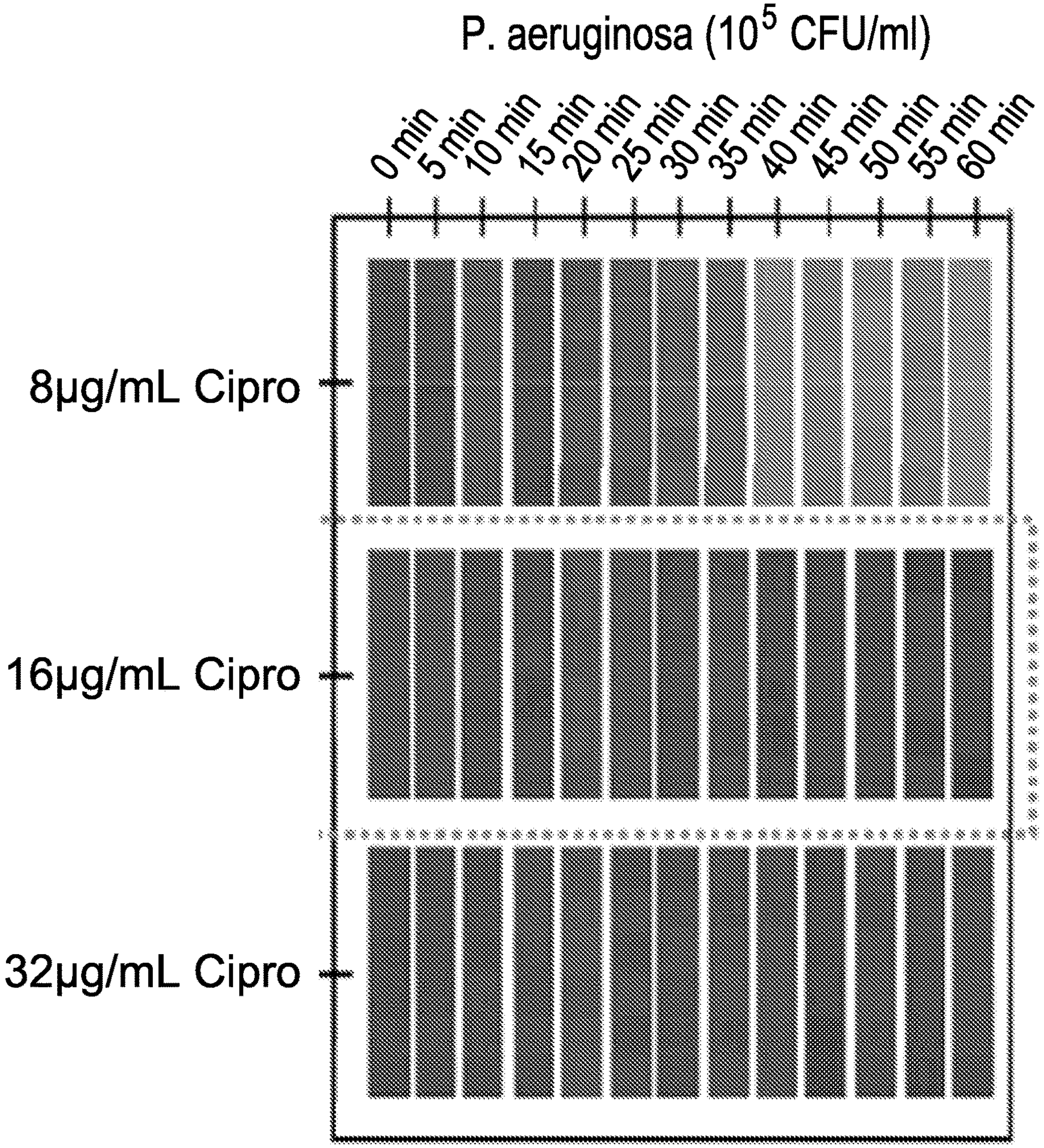
FIG. 10H shows a platform color response for aliquots of $5\times10^5$ CFU/mL Cipro. Resistant PA incubated at 37° C. incubated for different time durations from 0 minutes to 60 minutes with resazurin and different concentrations of Ciprofloxacin (8 μg/mL, 16 μg/mL and 32 μg/mL). The 8 μg/mL Ciprofloxacin dose was not enough to fully inhibit the Cipro. Resistant PA metabolism as shown by the color change witnessed from purple to cyan.
Figure 10I:
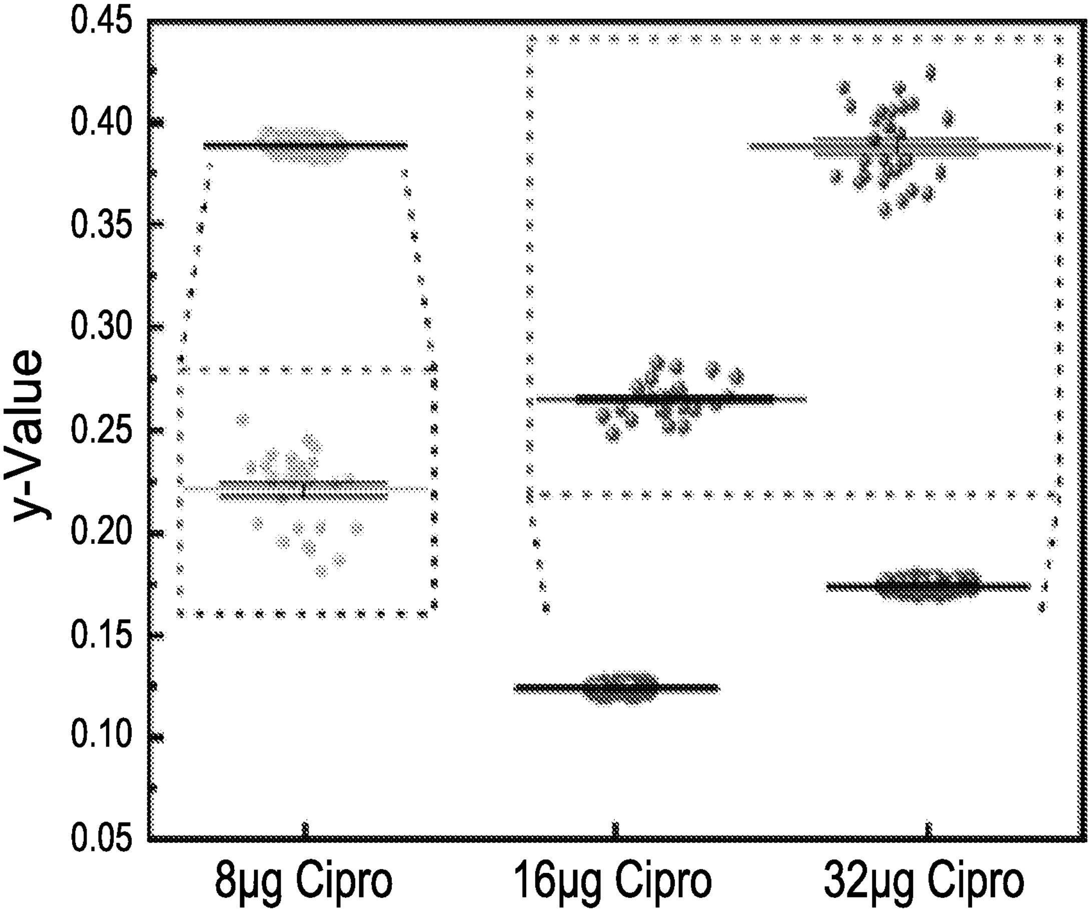
FIG. 10I is a y-value distribution of 60 minutes incubated aliquots of $5\times10^5$ CFU/mL Cipro. Resistant PA mixed with resazurin and (8 μg/mL, 16 μg/mL, and 32 μg/mL) Ciprofloxacin. 8 μg/mL Ciprofloxacin aliquot have a higher y-value (0.38) compared to 16 μg/mL and 32 μg/mL aliquots (0.125 and 0.175 respectively) indicating resistant bacteria. Thus, the MIC for Cipro. Resistant PA is 16 μg/mL. Standard MIC assay using CLSI protocols confirming the obtained MIC by the chip.
Figure 10J:
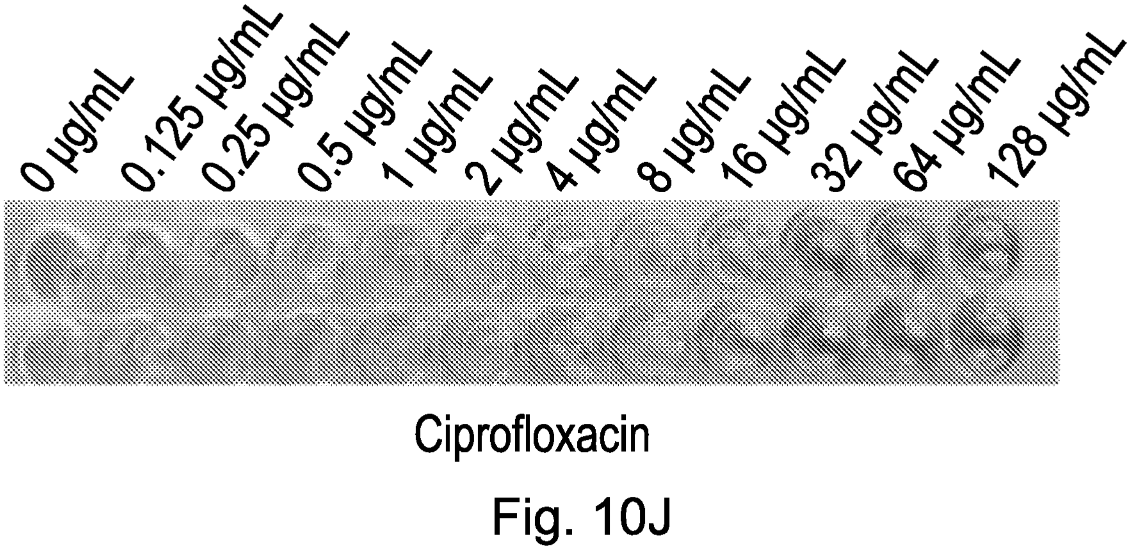
FIG. 10J shows a standard MIC assay using CLSI protocols confirming the obtained MIC in FIG. 10I (within acceptable two-fold variation).

Thirdly, a minimum inhibitory concentration (MIC) study for Amp. Resistant *E. coli*, Cipro. Resistant PA, and MRSA was conducted to determine the minimum antibiotic dose (kanamycin, ciprofloxacin, and oxacillin respectively) that would prevent further bacterial growth and proliferation (FIGS. 10A-10J). The antibiotic MIC showed no color change while lower concentration exhibited a color change trend indicative of resazurin reduction by viable bacteria. 5×$10^5$ CFU/mL bacteria aliquots were challenged with different concentrations of antibiotics. The aliquots were incubated at 37° C. for different time durations ranging from 0 minutes to 60 minutes with 5 minutes time intervals. FIGS. 10A, 10B, 10E, 10H show that the bacteria (Amp. Resistant *E. coli*, MRSA, and Cipro. Resistant PA) upon 60-minutes incubation, displayed color change from navy blue towards cyan depending on the concentration of antibiotics (Kanamycin, Ciprofloxacin, and Oxacillin respectively). This is shown for Amp. Resistant *E. coli* in FIG. 10C where y-value of the 4 μg/mL, 8 μg/mL, and 16 μg/mL were analyzed. 4 μg/mL kanamycin aliquot had a higher y-value (0.3) compared to 8 μg/mL and 16 μg/mL aliquots (0.125 and 0.175 respectively) indicating color change due to resazurin reduction to resorufin via viable bacterial cell towards a bright green color. Thus, it was determined that the minimum inhibitory concentration of kanamycin for the *E. coli* bacteria was 8 μg/mL. Accordingly, it is concluded that the *E. coli* aliquots were susceptible to kanamycin according to the Clinical & Laboratory Standards Institute—CLSI—criteria (Susceptible≤16; Resistant 64 mg/L). (Clinical and Laboratory Standards Institute. Performance standards for antimicrobial susceptibility testing. Nineteenth informational supplement. Approved standard M100-S20. Clinical and Laboratory Standards Institute: Wayne, Pa. (2010)). This is in close agreement (within an acceptable variation of two-fold dilution according to CLSI standards) with the standard CLSI MIC test previously performed (FIG. 10D) in earlier studies. (Mancini, S. et al. Population-based inference of aminoglycoside resistance mechanisms in *Escherichia coli. EBioMedicine* 46, 184-192 (2019)). Similarly, 60 minutes incubated aliquots of 5×$10^5$ CFU/mL MRSA mixed with resazurin and (16 μg/mL, 32 μg/mL, and 64 μg/mL) oxacillin were analyzed as shown in FIG. 10F. It was observed that 16 μg/mL Oxacillin aliquot had a higher y-value (0.3) compared to 32 μg/mL and 64 μg/mL aliquots (0.125 and 0.13 respectively) indicating the presence of viable bacteria. Thus, the MIC for MRSA was 32 μg/mL. Standard MIC assay using CLSI protocols (FIG. 10G) confirmed the obtained MIC by the chip 100, 100', 400, 400', 400". Accordingly, the strain is identified as oxacillin resistant according to the CLSI breakpoints ((Susceptible≤2; Resistant 4 mg/L)). The MIC value of ciprofloxacin against Cipro. Resistant PA was evaluated using both the chip 100, 100', 400, 400', 400" (FIG. 10I) and the standard CLSI protocol (FIG. 10J) and was determined to be 16 μg/mL. Thus, the strain is identified as ciprofloxacin-resistant strain according to the CLSI breakpoints (Susceptible≤0.5; Resistant 2 mg/L).

Figure 11A:
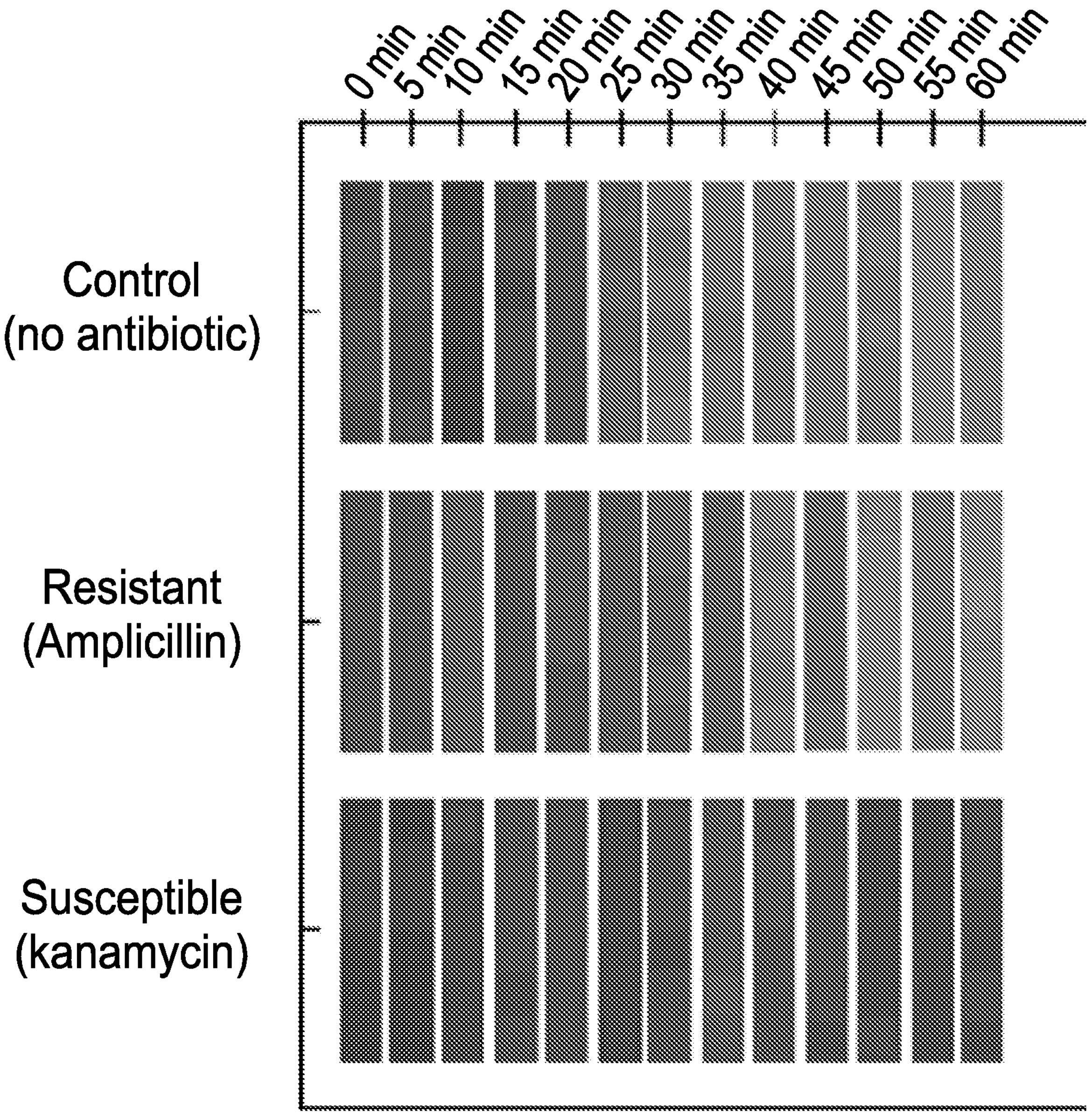
FIG. 11A shows a color response of a 400 nm platform in human urine spiked with $5\times10^5$ CFU/mL concentrations of ampicillin-resistant *E. coli* mixed with resazurin in presence of ampicillin (resistant), kanamycin (susceptible), and no antibiotics (control), showing the resistance of bacteria against Ampicillin (color-change from navy blue to green) and their susceptibility against Kanamycin (no color-change). Each micrograph was collected within 5 minutes of spiking bacteria in human urine during one-hour.
Figure 11B:
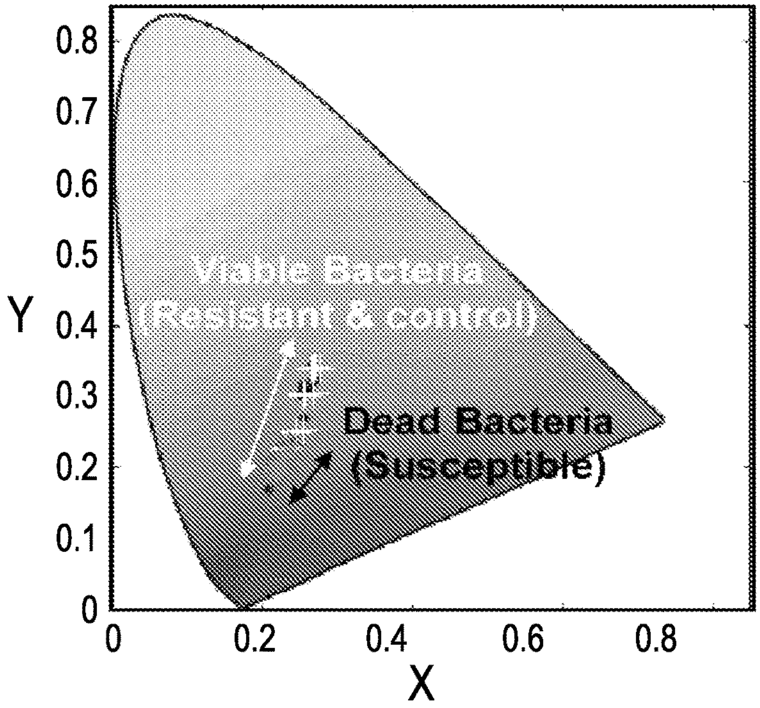
FIG. 11B is a the 2D CIE chromaticity diagram having color spots showing the rate of change in color for control, resistant, and susceptible cases of FIG. 11A.
Figure 11C:
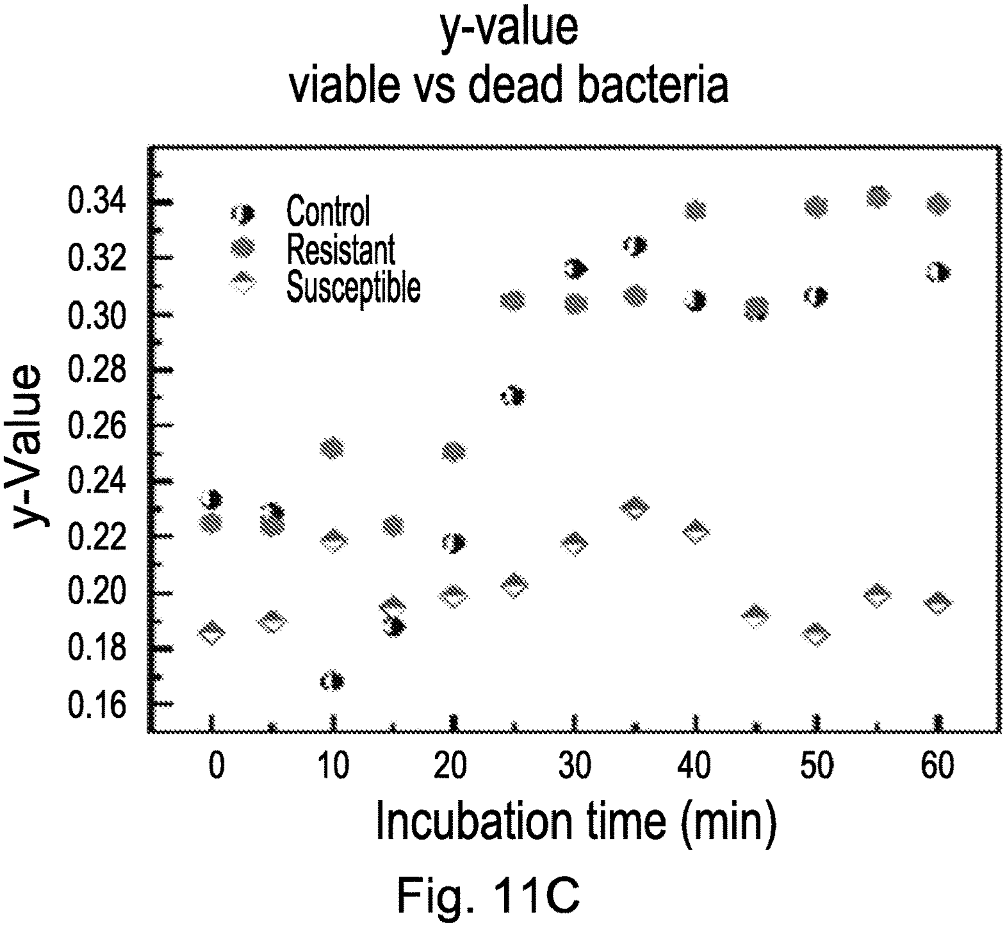
FIG. 11C is a comparison of y-values between control, resistant, and susceptible aliquots. Both control and resistant increase of y-values with time indicating color change towards green. In contrast, the susceptible aliquots exhibited no change in y-values indicating dead bacterial cells.
Figure 11D:
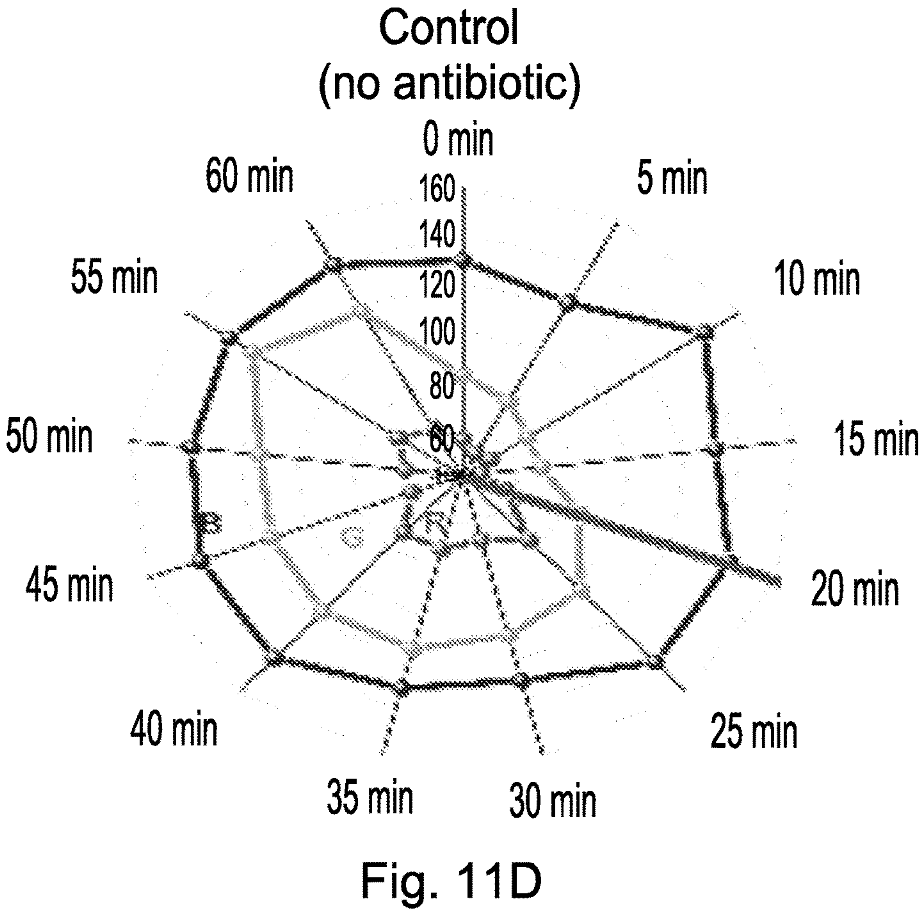
FIG. 11D show a web plot of the red, green, and blue values of the control (no antibiotic). Over the 1 hour incubation, an increase of the green value is witnessed indicating the presence of viable bacterial cells.
Figure 11E:
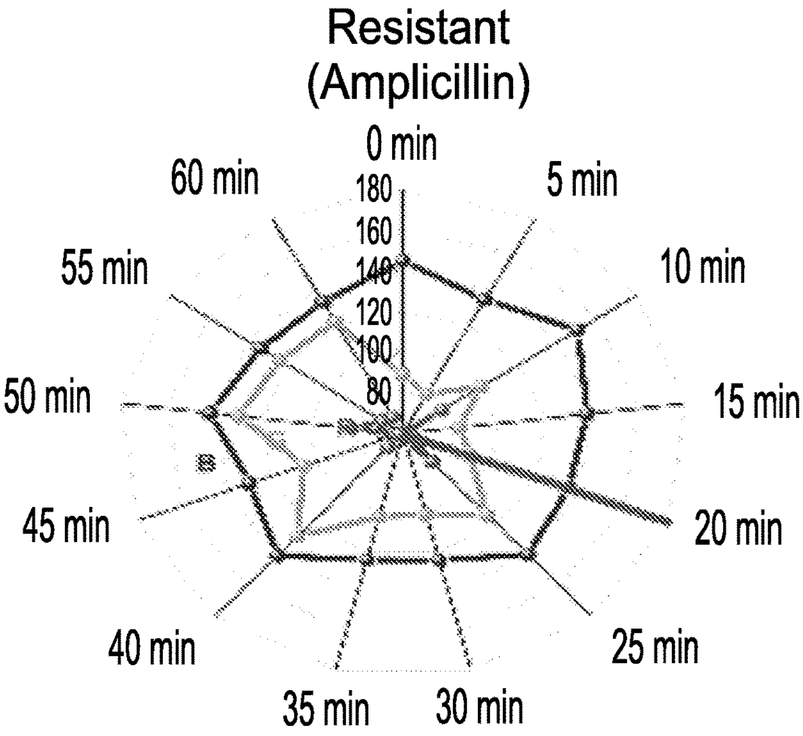
FIG. 11E show a web plot of the red, green, and blue values of the ampicillin resistant bacteria. Over the 1 hour incubation, an increase of the green value is witnessed indicating the presence of viable bacterial cells.
Figure 11F:
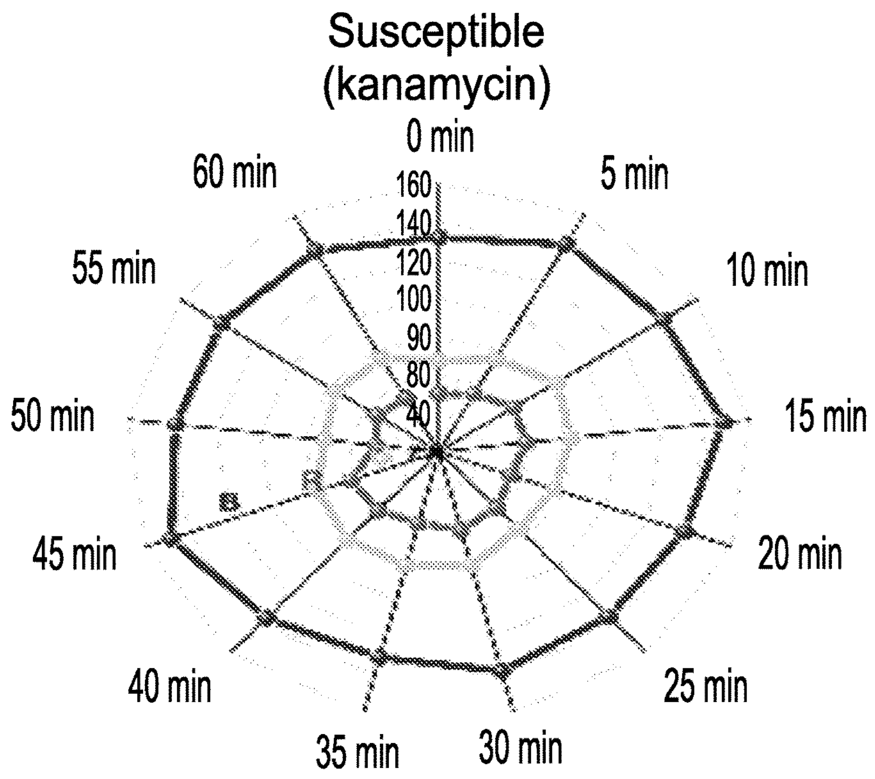
FIG. 11F show a web plot of the red, green, and blue values of the kanamycin susceptible bacteria. Over the 1 hour incubation, an increase of the green value is witnessed indicating the presence of viable bacterial cells.

FIGS. 11A-11F show the results of an antibiotic susceptibility study conducted using human urine spiked with Amp. Resistant *E. coli* to a final concentration of $5\times10^5$ CFU/mL. The study utilized 3 aliquot sets of control (no antibiotic), resistant (100 μg/mL Ampicillin), and susceptible (50 μg/mL Kanamycin). FIGS. 11A-11B show the color response of the different aliquot sets where the control and resistant sets showed a color change trend from dark blue at zero-minute incubation towards cyan by the end of 1-hour incubation. The trend is highlighted with a white arrow on the 2D chromaticity diagram in FIG. 11B. In contrast, the susceptible set exhibited a consistent dark blue color shown by the micrographs and the black line in the chromaticity diagram. This is further demonstrated in FIG. 11C where the y-values of the different sets were compared. Both control and resistant sets showed an increase in the y-value over time (0.23 to 0.31 for control aliquot and 0.22 to 0.34 for resistant aliquots) indicative of a color change to a brighter green color. While the y-value of the susceptible set showed a constant value (0.205±0.025) indicative of no color change towards green color. FIGS. 10D-10F are web plots of the red, green, and blue values analyzed from the bright-field microscopy of the sets. Red and blue values did not change overtime in each set. Green values increased overtime in the control and resistant sets (88 to 122 for resistant and 82 to 117 for control) showing the change towards green color and indicating the reduction of resazurin to resorufin by viable bacterial cells. The susceptible set showed constant red (56.6±4.7), green (76.8±4.5), and blue (138.7±5.3) values throughout the 1-hour incubation indicating the effectiveness of Kanamycin at inhibiting the Amp. Resistant *E. coli.*

Fourthly, a series of MIC tests were performed using a microdilution technique to study three strains of *E. coli*: DN624, DN829, and DN431. MIC tests were performed with three antibiotic drugs: ciprofloxacin, trimethoprim and sulfamethoxazole. in the microfluidic chip 100, 100', 400, 400', 400" was then used to detect the antibiotic resistance in several conditions. *E. coli* DN431 was tested with trimethoprim in concentrations of 0.0625, 0.125, 0.25, 0.5, 1, 2, 4, and 8 ug/mL. Furthermore, *E. coli* DN624 was tested with trimethoprim in concentrations of 2, 4, 8 ug/mL. Lastly, *E. coli* DN431 was also tested with sulfamethoxazole in concentrations of 19, 38, 76, and 154 ug/mL.

Figure 12A:
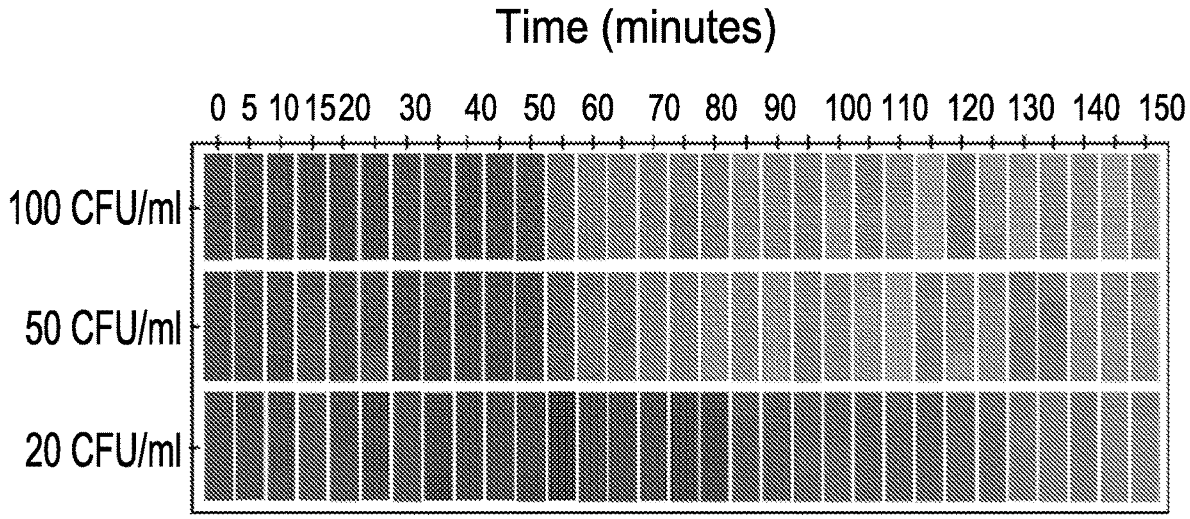
FIG. 12A shows a color response of a 400 nm platform in media of 100 CFU/ml, 50 CFU/ml, and 20 CFU/ml concentrations of Ampicillin-resistant *E. coli* mixed with resazurin in presence of 32 μg/mL Ampicilin antibiotic, showing the trend color-change from navy blue to green. Each micrograph was collected within 5 minutes of culturing bacteria in corresponding media during 150 minutes of starting the culture.
Figure 12B:
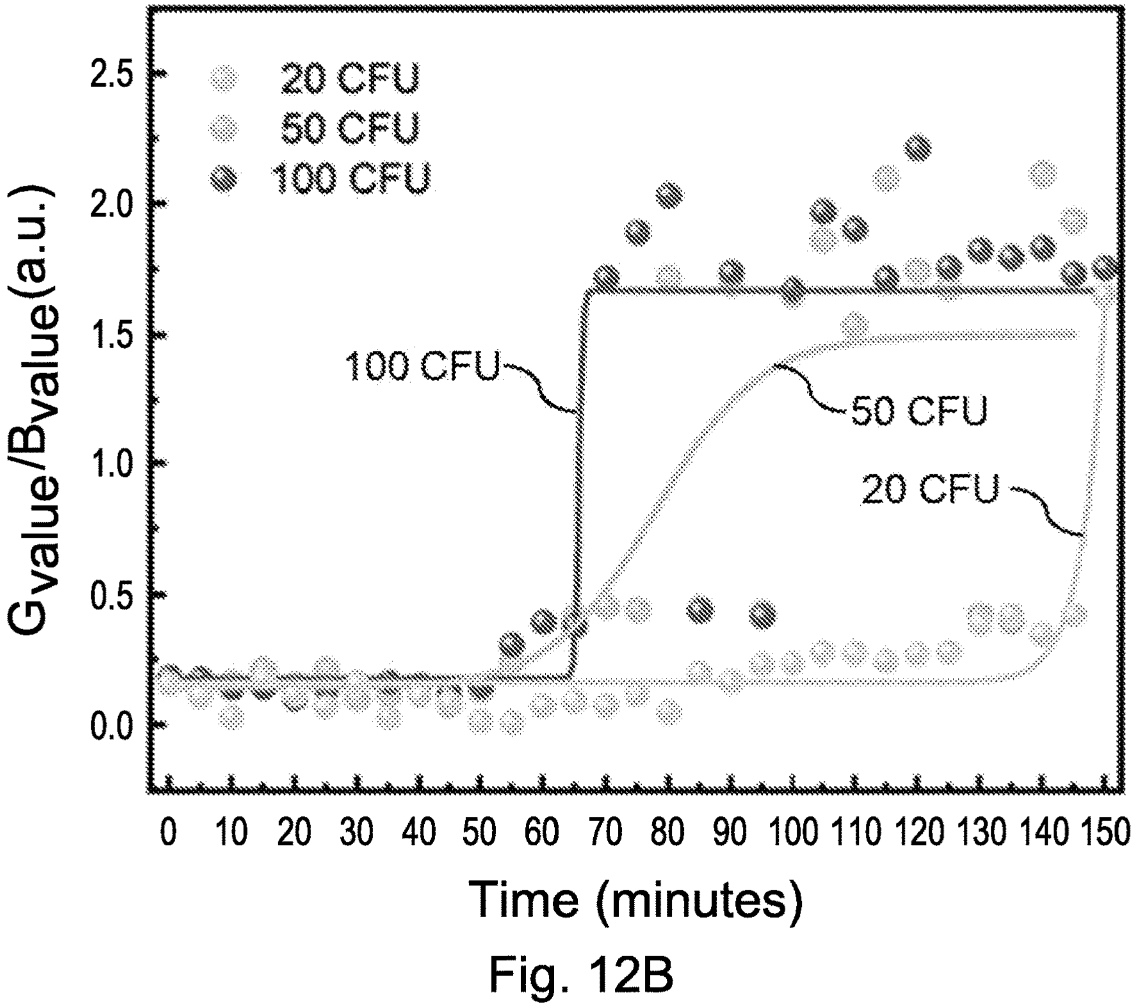
FIG. 12B is a graph of the $G_{value}/B_{value}$ curves of the color response from concentrations in FIG. 12A into a Rose-Dip fit.

FIGS. 12A-12B show the results of an antibiotic susceptibility study conducted using whole blood spiked with Amp. Resistant *E. coli* to a final concentration of 100, 50, 20 CFU/mL in the presence of 32 μg/mL Ampicilin. FIG. 12A shows the color response of the different bacteria concentrations where they all showed a color change trend from dark blue at zero-minute incubation towards cyan at different timepoints. The mean $G_{value}/B_{value}$ (a) can be a credible parameter to follow the sequence in the color change and translate it to a quantifiable data FIG. 12B. The α-value of the mean from five repeats for resistant state for each bacterium concentration shows a rise to high values at some point follow a dose-response fit while the starting time of the rise differed from one bacteria concentration to another. Quantifiably, the time in which the α-value undergoes a step levitation is corresponding to the time the color transition is visible to the naked eye.

To conclude Example I, antibiotic susceptibility profiles of different concentrations of Amp. Resistant *E. coli* were evaluated against Ampicillin and Kanamycin antibiotics. Rapid detection of Ampicillin resistance in 20 minutes was achieved. Consequently, the susceptibility profile of $5\times10^5$ CFU/mL initial concentration of Amp. Resistant *E. coli* against Ampicillin/Kanamycin, Cipro. Resistant PA against Ciprofloxacin/Gentamicin and MRSA against Oxacillin/Ciprofloxacin was evaluated. For each set of an experiment, a control set of aliquots with no antibiotics was evaluated. The minimum inhibitory concentration of Kanamycin, Ciprofloxacin, and Oxacillin was detected for Amp. Resistant *E. coli*, Cipro. Resistant PA, and MRSA strains respectively. The results agreed with standard MIC assays (within acceptable two-fold of variation) following the CLSI guidelines. Last, the antibiotic resistance profile of Amp. Resistant *E. coli* in human urine was evaluated successfully.

Example II

An ultra-rapid colorimetric microfluidic chip 100, 100', 400, 400', 400" integrating a colorimetric LAMP assay, on-chip heating, and plasmonic-enhanced color-sensitive platform was developed for the rapid detection of pathogenic bacterial DNA. The biosensor enables DNA detection within 15 min, offering a significantly faster response time compared to conventional PCR and culturing methods.

Loop-mediated isothermal amplification (LAMP) is a simple nucleic acid detection, which obviates the need for a thermal cycler and complex apparatuses, while maintaining similar sensitivity and specificity to PCR. LAMP involves using a set of 4-6 primers to amplify target DNA sequences in a rapid time frame of 15-60 min at a temperature ranging from 55-65° C. This example employs a (LAMP) assay to detect nucleic acids within 15 minutes. Colorimetric readout techniques can seamlessly be implemented in LAMP by coupling it with color sensors or fluorescent dyes, such as phenol red, calcein, malachite green, and hydroxynaphthol blue, that vary in intensity based on changes in the molecular environment. The present Example II describes a reaction that changes colour in the presence of, color sensor, phenol red due to DNA amplification by the primers. Above a pH of 8.2, phenol red exhibits a fuchsia color and between 8.2 and 6.2, phenol red shows a gradual transition from red to yellow due to the addition of a hydroxyl group enabling the detection of amplicons (chemical structures of Phenol Red Basic going into Phenol Red Acidic are shown below). In the presence of a target DNA, the primers begin to anneal and amplify the DNA at a constant temperature of 60-65° C. As nucleotides are added to the nascent DNA strand by DNA polymerase, $H^+$ ions are released in the medium, which causes a change in the pH. The increased proton concentration subsequently changes the color of phenol red to yellow, in the presence of a positive sample. The optical sensitivity of colorimetric assays can be further augmented through the resolution of the color pigment that is captured by plasmonic excitation.

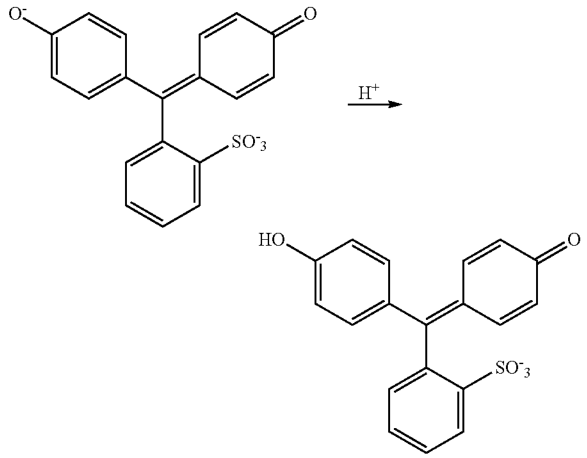

*E. coli* samples were cultured overnight at 37° C. in Luria Broth (LB) media. Next, the bacteria concentration was determined using a Spectronic 21D spectrophotometer. Aliquots of different concentrations of 107 CFU/mL, 105 CFU/mL, 104 CFU/mL, 103 CFU/mL, 102 CFU/mL, and 10 CFU/mL were prepared to match physiological concentrations by suspending the *E. coli* cultures in LB media. *E. coli* DNA was extracted using the boiling method at 95° C. for 10 min Methicillin-resistant *S. aureus* and *P. aeruginosa* DNA was obtained from the McGill University Health Centre using the chemical lysis method to extract DNA. Samples were suspended in buffer to match concentrations in the physiological range. All DNA sample concentrations were measured using a Nanodrop™ 2000 Spectrophotometer and suspended in Universal Buffer (Bio Basic Inc., ON, CA) to achieve desired concentrations. Spiked urine experiments were carried out using pooled human urine (Innovative Research, MI, USA).

Three different sets of LAMP primers were used in this study for the corresponding pathogenic DNA samples as shown in Table 1. All three primer sets were purchased from Sigma-Aldrich.

TABLE 1

Primer sets and initial concentration of each primer for *E. Coli*, Methicillin-resistant *S. Aureus*, and *P. Aeruginosa*.

| Primer | SEQ ID | 5′ to 3′ Sequence | Initial Concentration |
|---|---|---|---|
| *E. Coli* LAMP Primer Set Targeting malB Gene | | | |
| F3 | SEQ ID NO: 1 | gccatctcct gatgacgc | 0.2 µM |
| B3 | SEQ ID NO: 2 | atttaccgca gccagacg | 0.2 µM |
| FIP | SEQ ID NO: 3 | cattttgcag ctgtacgctc gcagcccatc atgaatgttg ct | 1.6 µM |
| BIP | SEQ ID NO: 4 | ctggggcgag gtcgtggtat tccgacaaac accacgaatt | 1.6 µM |
| LF | SEQ ID NO: 5 | ctttgtaaca acctgtcatc gaca | 0.8 µM |
| LB | SEQ ID NO: 6 | atcaatctcg atatccatga aggtg | 0.8 µM |
| Methicillin-resistant *S. Aureus* LAMP Primer Set Targeting mecA Gene | | | |
| F3 | SEQ ID NO: 7 | ggctcaggta ctgctatc | 0.4 µM |
| B3 | SEQ ID NO: 8 | ttgttattta acccaatcat tgc | 0.4 µM |
| FIP | SEQ ID NO: 9 | atgccataca taaatggata gacgtcaaac aggtgaatta ttagcactt | 1.6 µM |
| BIP | SEQ ID NO: 10 | ccgaagataa aaaagaacct ctgctttttt gagttgaacc tggtg | 1.6 µM |
| LF | SEQ ID NO: 11 | catatgaagg tgtgcttac | 0.8 µM |
| LB | SEQ ID NO: 12 | caagttccag attacaactt | 0.8 µM |
| *P. Aeruginosa* LAMP Primer Set Targeting oprL Gene | | | |
| F3 | SEQ ID NO: 13 | gcgttgccgc caacaatg | 0.2 µM |
| B3 | SEQ ID NO: 14 | catgcgggca acctctc | 0.2 µM |
| FIP | SEQ ID NO: 15 | gttgtcaccc cacctccggg cggcaacgtt cctcc | 1.6 µM |
| BIP | SEQ ID NO: 16 | ctccgtgcag ggcgaactgc aggcgagcca actc | 1.6 µM |

TABLE 1-continued

| Primer sets and initial concentration of each primer for *E. Coli*, Methicillin-resistant *S. Aureus*, and *P. Aeruginosa*. | | | |
|---|---|---|---|
| LF | SEQ ID NO: 17 | acctgccgtg ccatacc | 0.8 μM |
| LB | SEQ ID NO: 18 | gttcatgcag ctccagcag | 0.8 μM |

The LAMP reaction consisted of four components: the DNA sample, 10× primer mix for each individual DNA sample, WarmStart™ Colorimetric LAMP 2× Master Mix (NewEngland Biolabs, MA, USA), and DNAse-free H2O (Thermo Fischer Scientific, MA, USA). The standard reaction volume of 25 μl consisted of 2.5 μl 10× primer mix, 12.5 μl WarmStart™ Colorimetric LAMP 2× Master Mix, 9 μl DNase-free H2O, and 1 μl DNA sample. The LAMP reaction was incubated at a temperature ranging from 60-65° C. and monitored for color changes at different intervals up to 60 min.

For bacterial DNA in buffer, the LAMP mixture was loaded through the inlet 101, 101', as all reagents were mixed off-chip prior to injecting in the microfluidic chip 100, 100', 400, 400', 400". For *E. coli* in urine, the DNA sample was loaded through the sample inlet 101, 101', while the remaining LAMP cocktail was loaded in the second inlet 106. All ports were covered with a thin film of tape to prevent leakage and evaporation prior to heating the microfluidic chip. Next, a direct current (DC) power supply was connected to the microfluidic chip and fine-tuned for a temperature reading of 60-65° C. A FLIR One Pro Infrared camera was connected to a smartphone to monitor the temperature throughout the experiment. Finally, the colorimetric readout was monitored from the plasmonic color-sensitive window for approximate 60 min using a brightfield microscope with a color camera. (Nikon Ti Eclipse microscope).

Platform RGB images were acquired at regular intervals from 0-60 min. A deep learning algorithm was used to pre-process the images. The outer 20% of the images were cropped out to remove the coffee ring effect. Next, hue values ranging from 85 to 140, falling within the blue range, were removed and replaced by the mean of the rest of the image. The bottom 25% of the parts with lowest saturation were removed and replaced with the mean value of the rest of the image. In the final step, the image was broken down into 20 mini-images and several features were extracted including mean color values in each color channel R, G, and B.

Figure 13A:
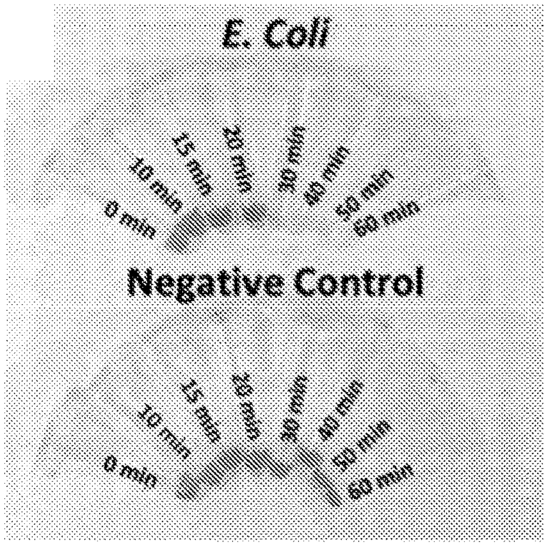
FIG. 13A is a photograph of specificity results of LAMP primers for *E. coli*, Methicillin-resistant *S. aureus*, and *P. aeruginosa*, off-chip results of LAMP assay in water bath for each sample up to 60 min.
Figure 13B:
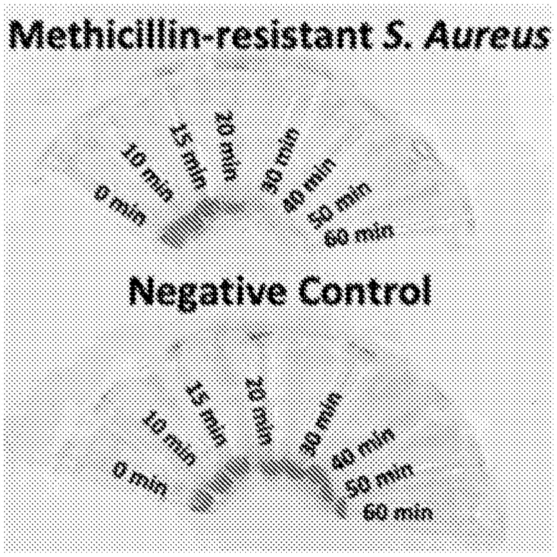
FIG. 13B is a photograph of specificity results of LAMP primers for Methicillin-resistant *S. aureus*, off-chip results of LAMP assay in water bath for each sample up to 60 min.
Figure 13C:
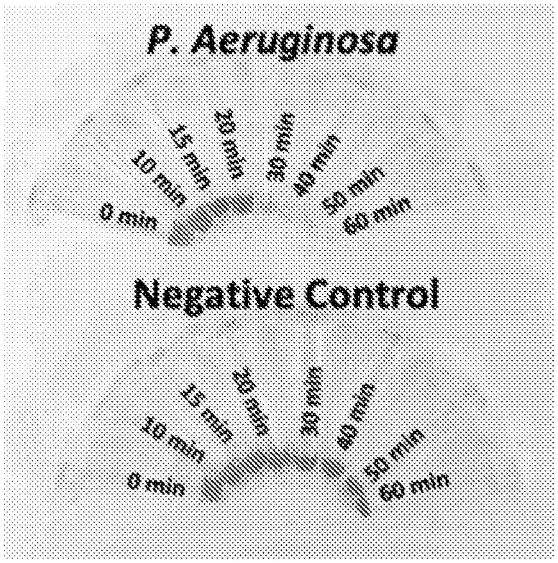
FIG. 13C is a photograph of specificity results of LAMP primers for *P. aeruginosa*, off-chip results of LAMP assay in water bath for each sample up to 60 min.

The LAMP assay effectiveness was assessed through off-chip experiments where the set of primers selected were validated. In brief, the LAMP cocktail was prepared in an Eppendorf tube and heated at a steady temperature of 60-65° C. in a water bath for different time intervals up to 60 min. We tested each pathogenic bacteria sample at a DNA concentration of 50 ng/μL. Negative controls samples were prepared without DNA, but with the remaining components of the LAMP cocktail. The off-chip response of DNA amplification was assessed by monitoring the color change of each reaction in the presence of phenol red. FIGS. 13A-13C show the off-chip response of the LAMP cocktail from 0-60 min for each pathogen compared to negative control samples. Off-chip color change from fuchsia to yellow was noticeable for each sample at 30 min.

Figure 13D:
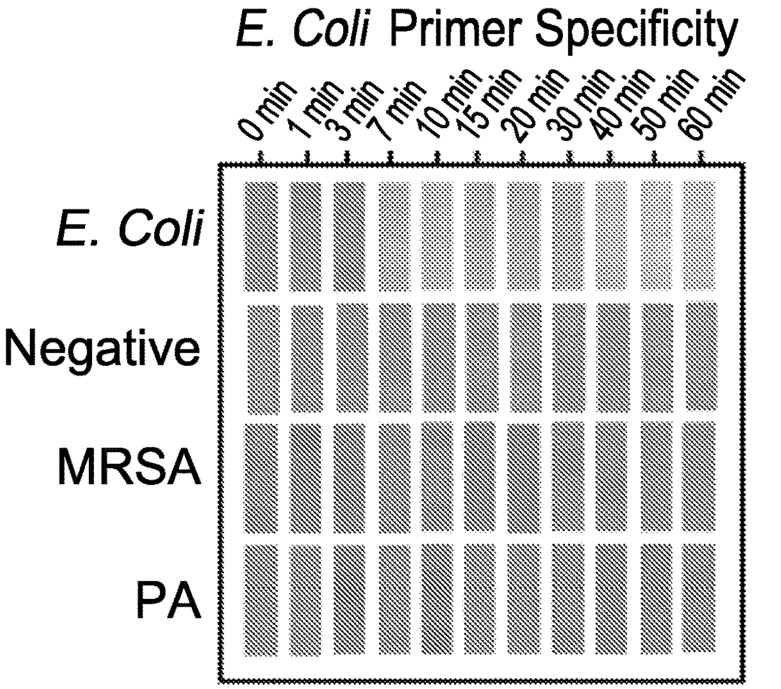
FIG. 13D shows a color matrix of an on-chip cross reactivity test for an *E. coli* bacterial primer set up to 60 min.
Figure 13E:
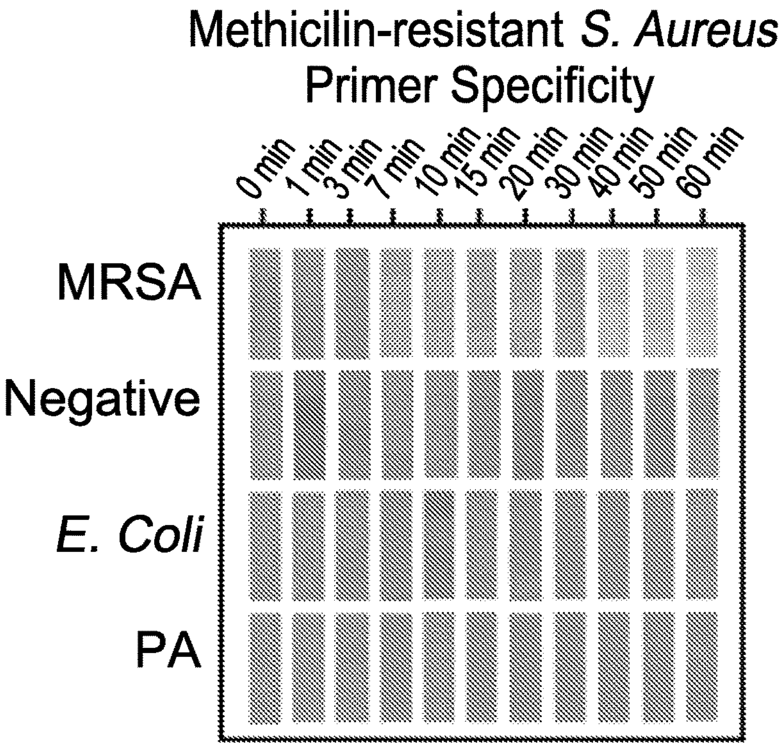
FIG. 13E shows a color matrix of an on-chip cross reactivity test for a Methicillin-resistant *S. aureus* bacterial primer set up to 60 min.
Figure 13F:
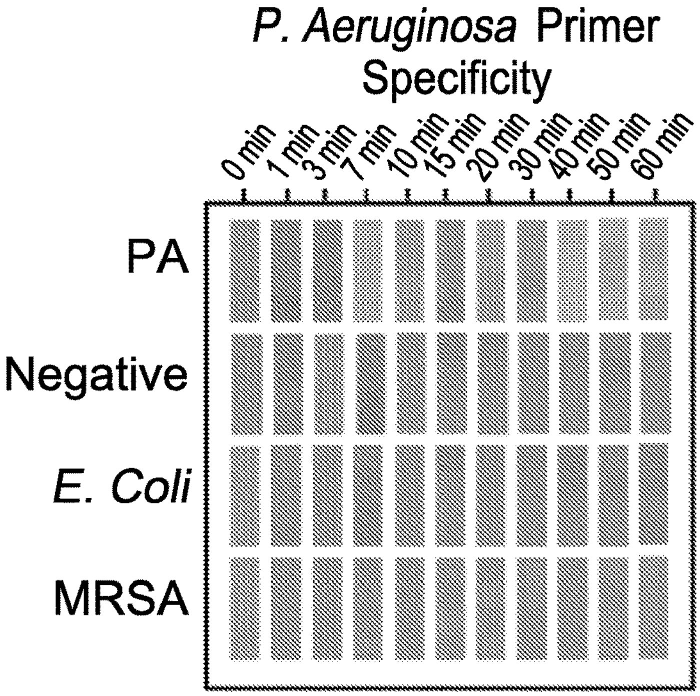
FIG. 13F shows a color matrix of an on-chip cross reactivity test for *P. aeruginosa* bacterial primer set up to 60 min.

Next, the specificity of each primer set was investigated in the colorimetric microfluidic chip 100, 100', 400, 400', 400" through a cross reactivity on-chip test with the target DNA sample, the two non-target DNA samples, and a negative control sample without DNA. The DNA concentrations for individual bacteria samples were 50 ng/μL. For this experiment all primer sets for each pathogen (*E. coli*, Methicillin-resistant *S. aureus*, and *P. aeruginosa*), specifically reacted with target DNA, exhibiting no cross-reactions with non-target DNA or negative control samples. FIGS. 13D-13F illustrate a matrix of sampled colors from the raw bright-field microscopy images at each time interval up to 60 min. Between 3-5 images were captured at each time interval, rendering a wide color gamut from fuchsia to orange in the presence of target DNA only. Visibly, target-specific primers led to a rapid color change within 7 min, as identified by a gradual color change from fuchsia to light pink (FIGS. 13D-13F). In contrast, non-target DNA samples and negative controls remained fuchsia.

Figure 13G:
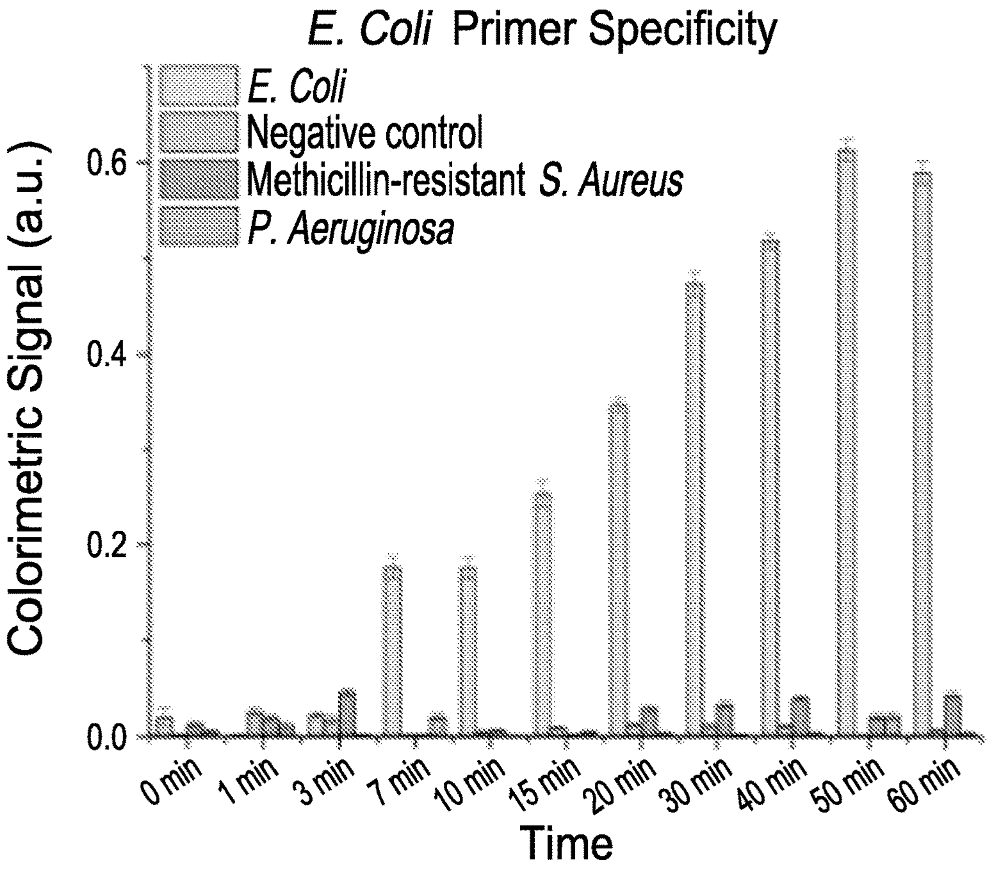
FIG. 13G is a bar graph showing the quantitative change in the colorimetric signal for cross reactivity test for the *E. coli* primer set, showing all target-specific primers led to increase in colorimetric signal past threshold of 0.1 a.u.
Figure 13H:
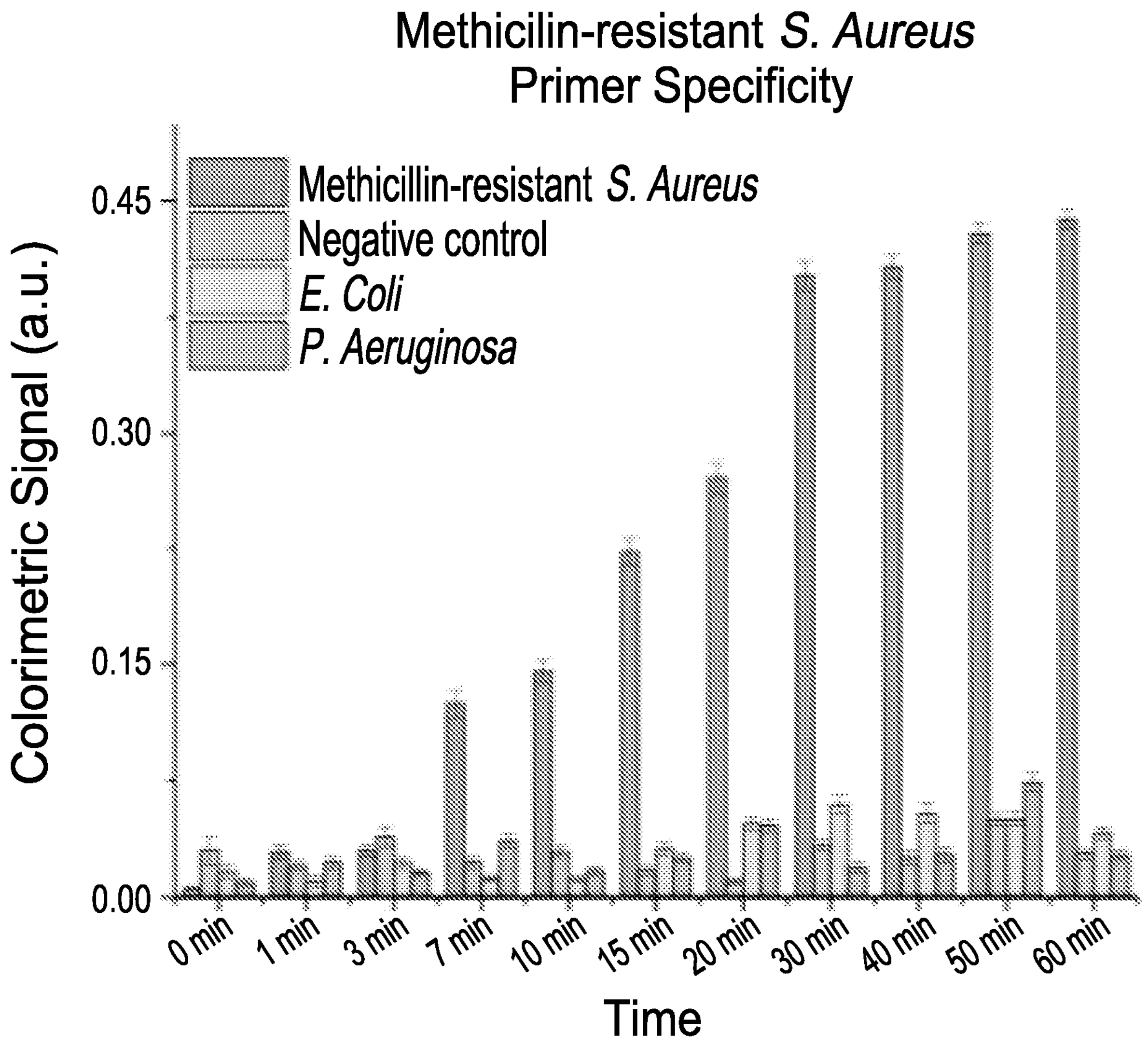
FIG. 13H is a bar graph showing the quantitative change in the colorimetric signal for cross reactivity test for the Methicillin-resistant *S. aureus* primer set, showing all target-specific primers led to increase in colorimetric signal past threshold of 0.1 a.u.
Figure 13I:
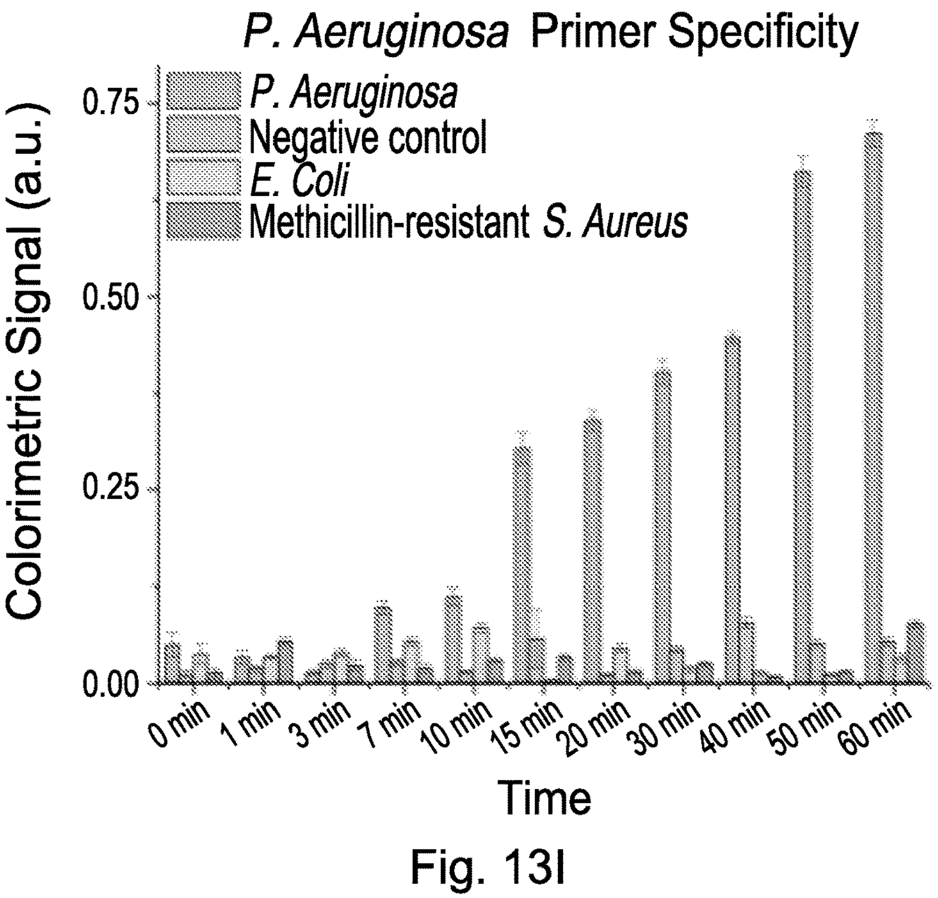
FIG. 13I is a bar graph showing the quantitative change in the colorimetric signal for cross reactivity test for the *P. aeruginosa* primer set, showing all target-specific primers led to increase in colorimetric signal past threshold of 0.1 a.u.

The images were pre-processed using a deep learning algorithm and mean values in each color channel (R, G, and B) values were extracted from the raw images, in order to quantify the colorimetric signal. The colorimetric signal (a.u.) was defined as $G^2/RB$, using the normalized mean values. This was defined based on increasing mean G values and decreasing mean R and B values for positive tests. FIGS. 13G-131 depict the colorimetric signal for the specificity cross reaction for each pathogen. Evidently, the target DNA for each primer set showed an increased colorimetric signal within 60 min. It was possible to identify a spike in the colorimetric signal as early as 7 min for concentrations of 50 ng/μL. At 7 min, the response surpassed a colorimetric signal of 0.1 a.u., helping to identify this as a signal threshold for positive samples. Non-target DNA and negative controls remained below the 0.1 a.u. signal threshold throughout the 60 min test. These quantitative results validated the qualitative responses seen in microscopy images.

Figure 13J:
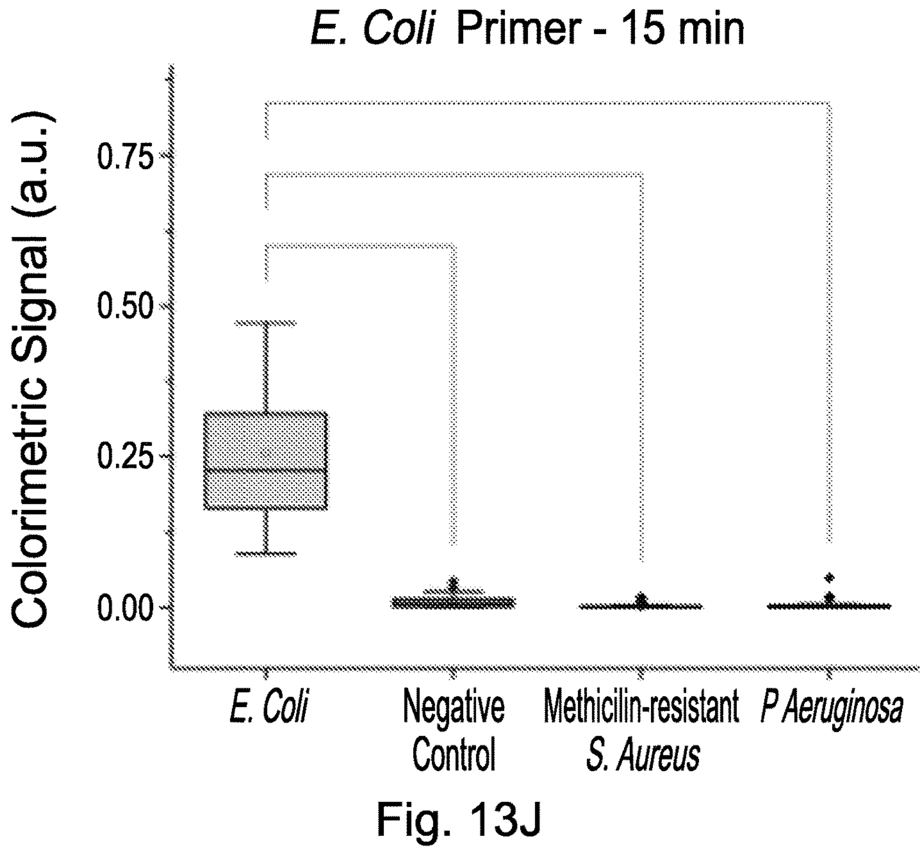
FIG. 13J is a box plot comparison of colorimetric signal at 15 min for the cross reactivity test for the *E. coli* primer set. All target-specific primers showed significant differences with non-target DNA samples and negative controls ($p<0.001$).
Figure 13K:
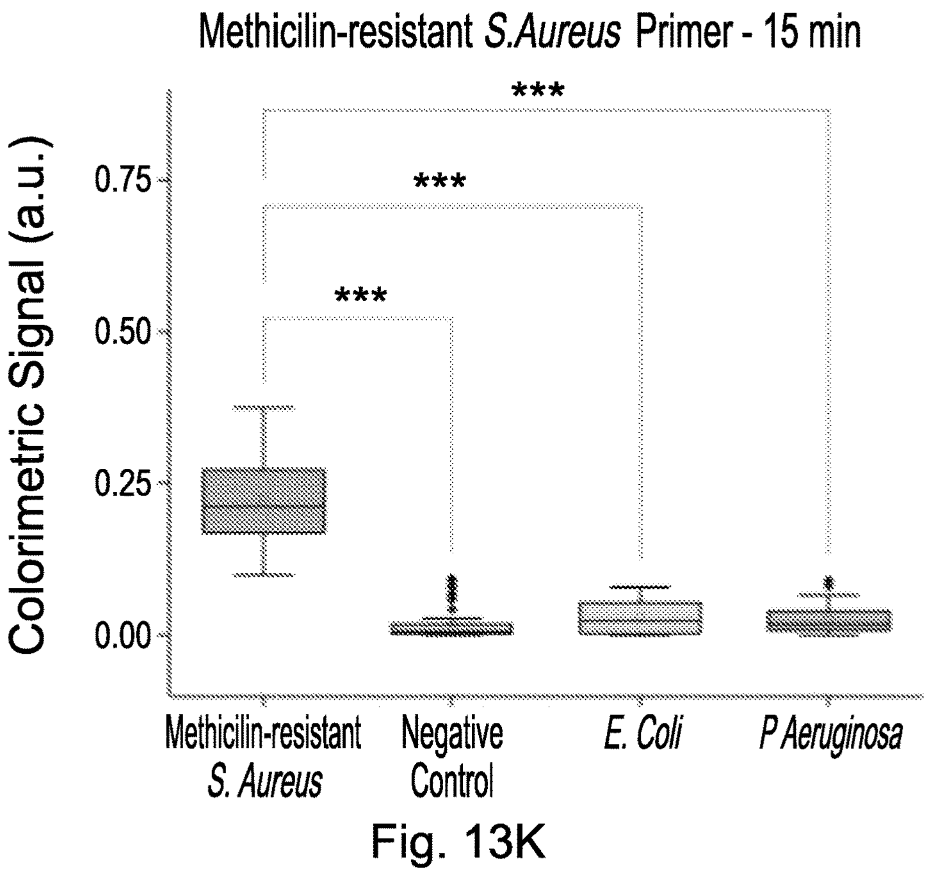
FIG. 13K is a box plot comparison of colorimetric signal at 15 min for the cross reactivity test for the Methicillin-resistant *S. aureus* primer set. All target-specific primers showed significant differences with non-target DNA samples and negative controls ($p<0.001$).
Figure 13L:
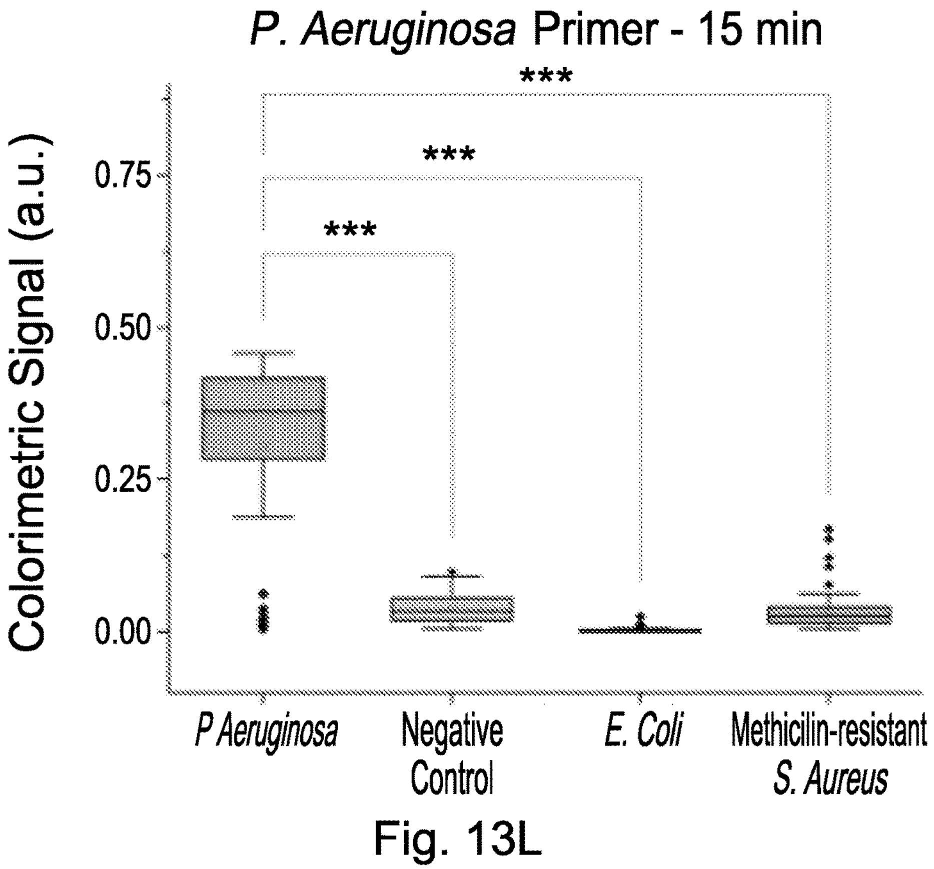
FIG. 13L is a box plot comparison of colorimetric signal at 15 min for the cross reactivity test for the *P. aeruginosa* primer set. All target-specific primers showed significant differences with non-target DNA samples and negative controls ($p<0.001$).

A comparison of the colorimetric signal was evaluated specifically at 15 min, corresponding to the detection time for low concentrations, using a one-way analysis of variance (ANOVA) with a post-hoc Tukey's test. Significant differences were observed for the colorimetric signal for the target DNA compared to the non-target DNA and negative control for *E. coli*, Methicillin-resistant *S. aureus*, and *P. aeruginosa*, ($p<0.001$) (FIGS. 13J-13L).

The primer sets for each DNA sample, exhibited 100% specificity for target DNA samples, showing no cross reactions with non-targets or negative control samples.

The sensitivity of the microfluidic chip 100, 100', 400, 400', 400" was evaluated for the detection of the physiological range of bacteria in samples. *E. coli* in urine generally presents itself in the range of 102-105 CFU/mL, in urinary tract infections. In the present experiments, the extracted DNA concentrations were 70 ng/μL, 50 ng/μL, 20 ng/μL, 10 ng/μL, 3 ng/μL, and 0.2 ng/μL, corresponding to 107 CFU/mL, 105 CFU/mL, 104 CFU/mL, 103 CFU/mL, 102 CFU/mL, and 10 CFU/mL, respectively. This allowed the preparation and testing of *E. coli* DNA samples in the range of 0.2 ng/μL-70 ng/μL.

For Methicillin-resistant *S. aureus*, the physiological DNA concentration averages between 40-50 ng/μL in nasopharyngeal samples of infection, while *P. aeruginosa* presents itself in the range between 10-100 ng/μL in patient sputum samples. To test these samples, DNA samples were prepared in the range of 0.2 ng/μL-50 ng/μL.

Figure 14A:
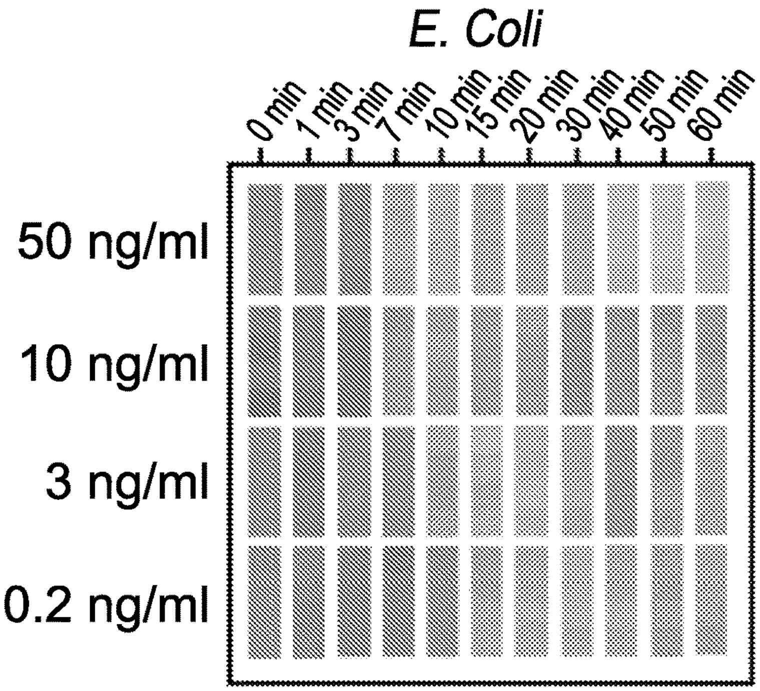
FIG. 14A shows sensitivity results for *E. coli* illustrated by color matrices of on-chip sensitivity test for each bacterial DNA for 0.2 ng/μL, 3 ng/μL, 10 ng/μL, and 50 ng/μL.
Figure 14B:
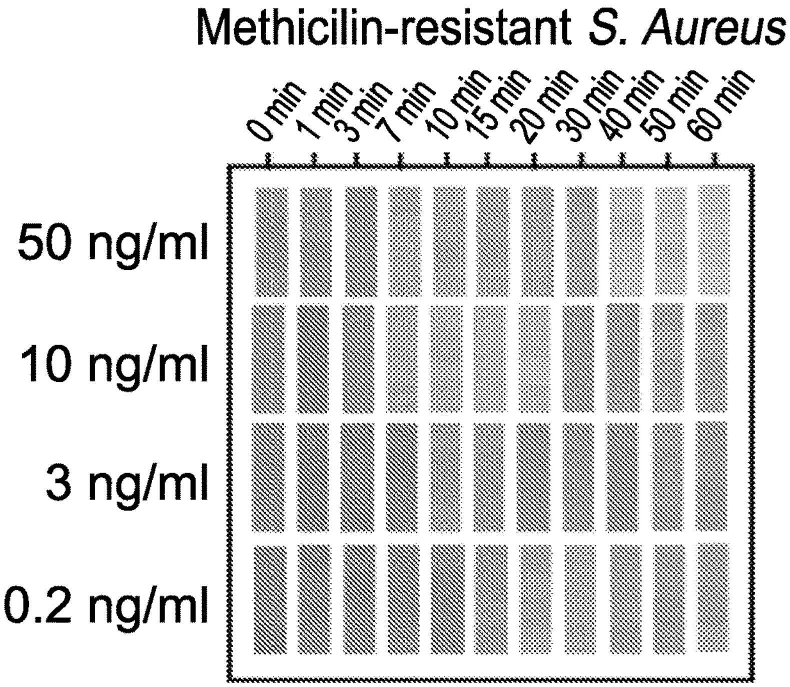
FIG. 14B shows sensitivity results for Methicillin-resistant *S. aureus* illustrated by color matrices of on-chip sensitivity test for each bacterial DNA for 0.2 ng/μL, 3 ng/μL, 10 ng/μL, and 50 ng/μL.
Figure 14C:
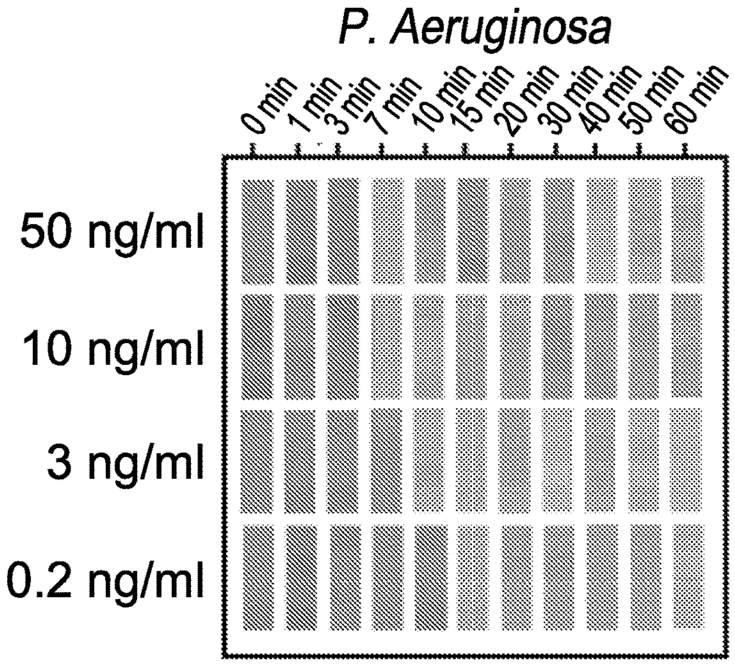
FIG. 14C shows sensitivity results for *P. aeruginosa* illustrated by color matrices of on-chip sensitivity test for each bacterial DNA for 0.2 ng/μL, 3 ng/μL, 10 ng/μL, and 50 ng/μL.
Figure 14D:
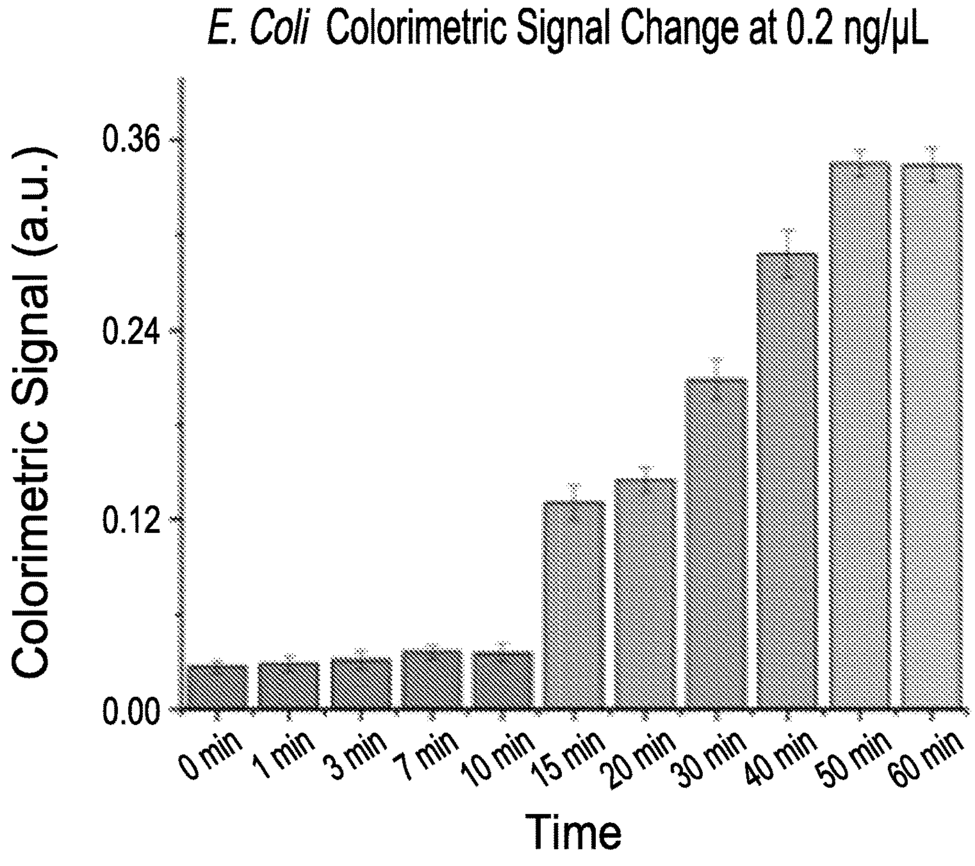
FIG. 14D is a bar graph of the quantitative colorimetric signal change for 50 ng/μL of FIG. 14A.
Figure 14E:
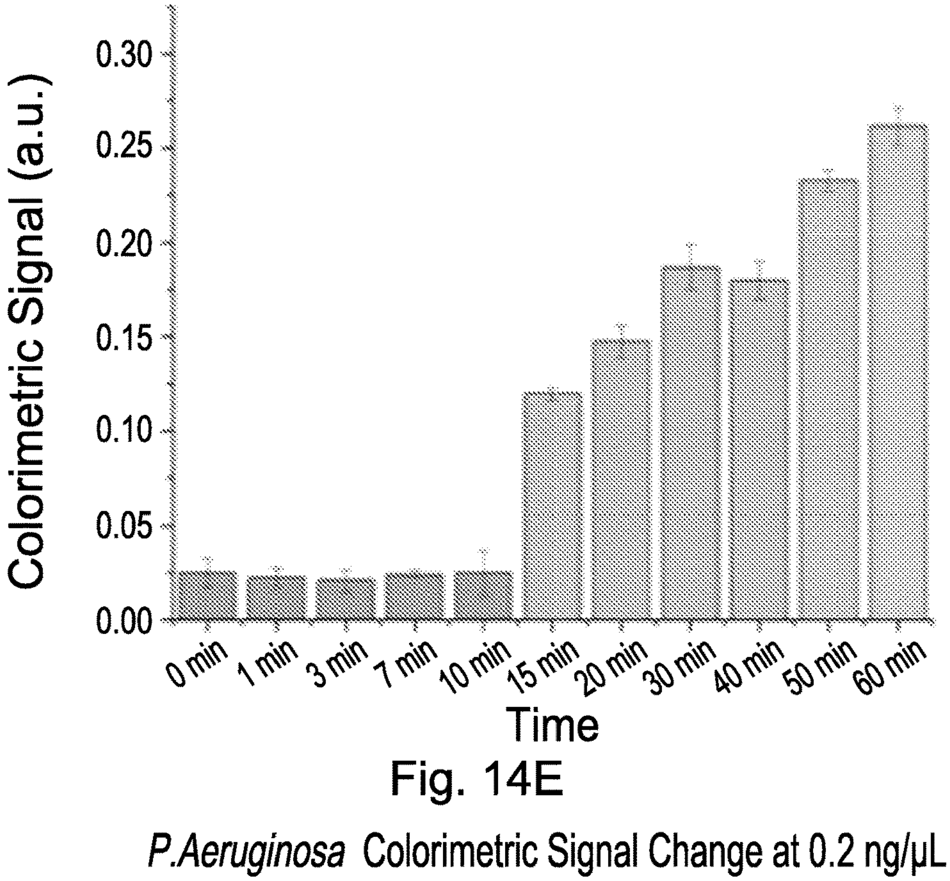
FIG. 14E is a bar graph of the quantitative colorimetric signal change for 50 ng/μL of FIG. 14B.
Figure 14F:
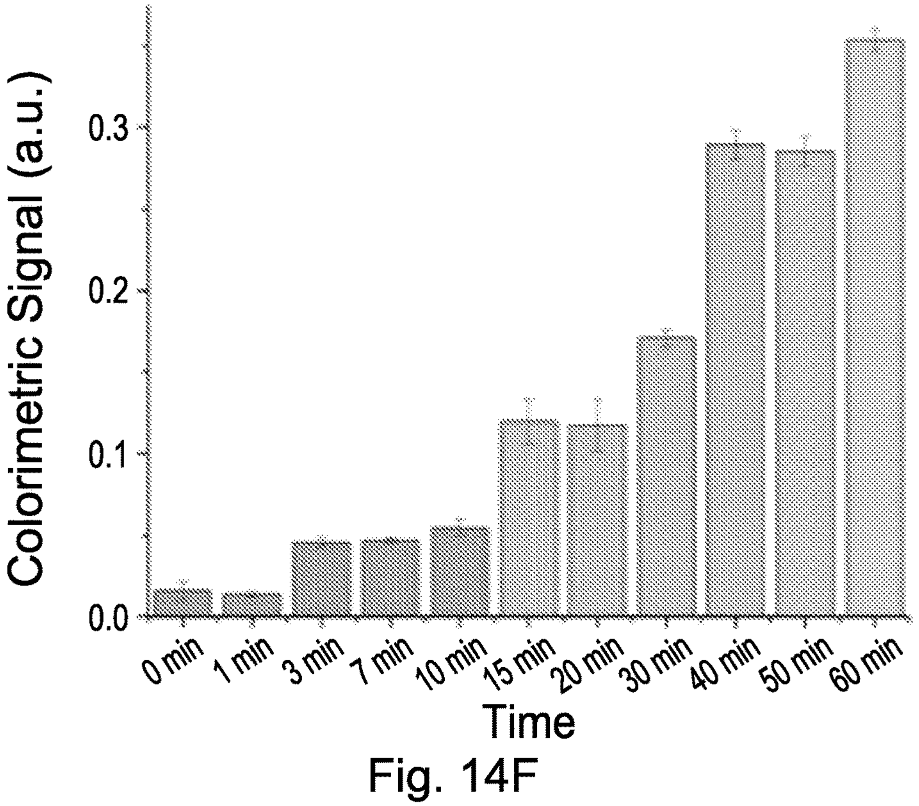
FIG. 14F is a bar graph of the quantitative colorimetric signal change for 50 ng/μL of FIG. 14C.

FIGS. 14A-14C each illustrate a color matrix of sampled colors from the raw microscopy images of on-chip LAMP sensitivity experiments. The lowest DNA concentration of 0.2 ng/μL showed a color change as early as 15 min, as evidenced from a visible transition in colour from fuchsia to light pink. In contrast, DNA concentrations of 50 ng/μL portrayed a color change at 7 min. This pattern was observed for all three bacteria. The colorimetric signal change at 50 ng/μL was plotted for all three bacteria, confirming that a spike in the colorimetric signal change occurred at 7 min as the signal passed 0.1 a.u., validating the observed qualitative responses (FIGS. 14D-14F).

Figure 14G:
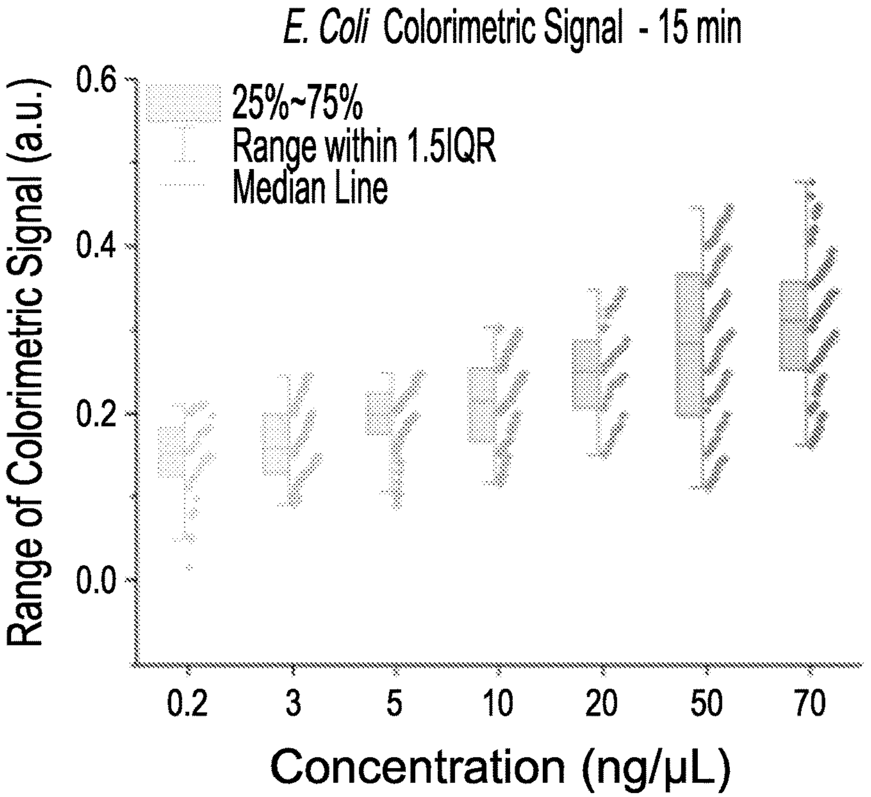
FIG. 14G is a box plot depicting the range of data points for the mean colorimetric signals in function of the concentration of *E. coli*.
Figure 14H:
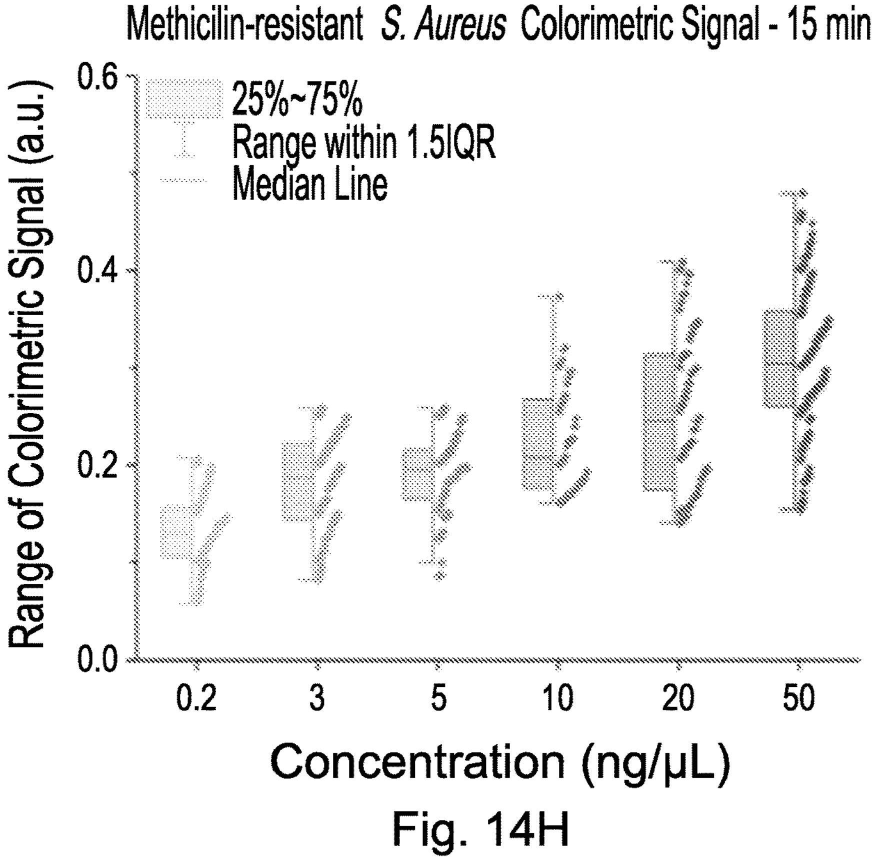
FIG. 14H is a box plot depicting the range of data points for the mean colorimetric signals in function of the concentration of Methicillin-resistant *S. aureus*.
Figure 14I:
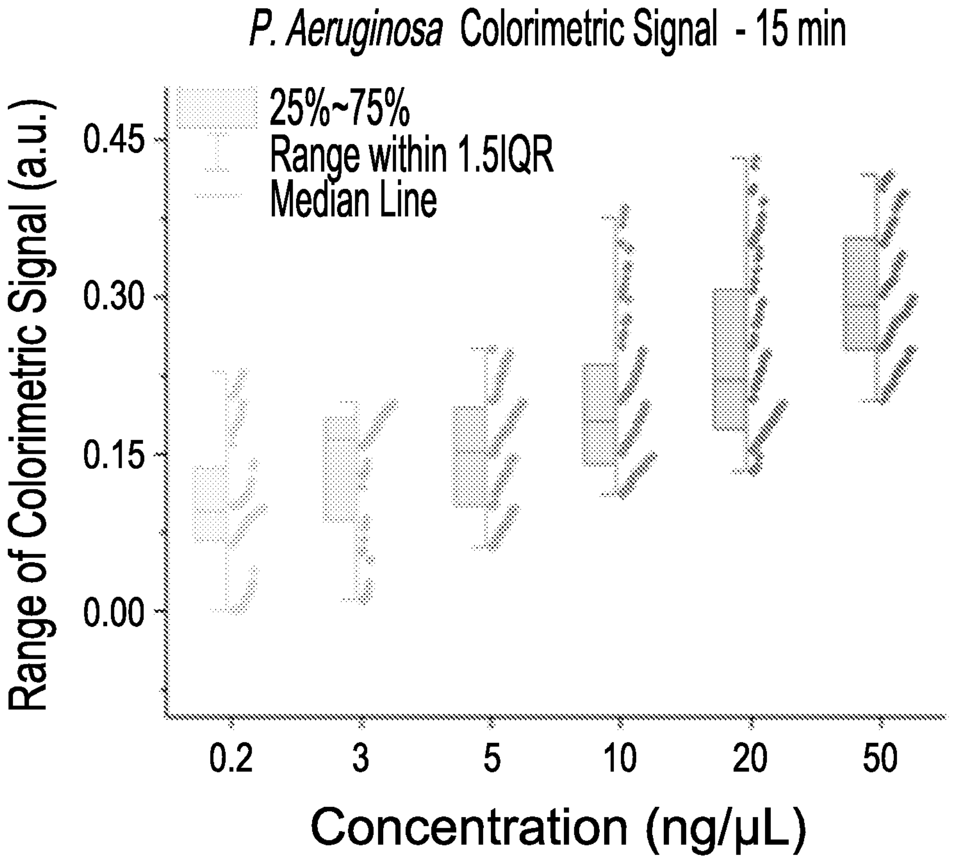
FIG. 14I is a box plot depicting the range of data points for the mean colorimetric signals in function of the concentration of *P. aeruginosa*.
Figure 14J:
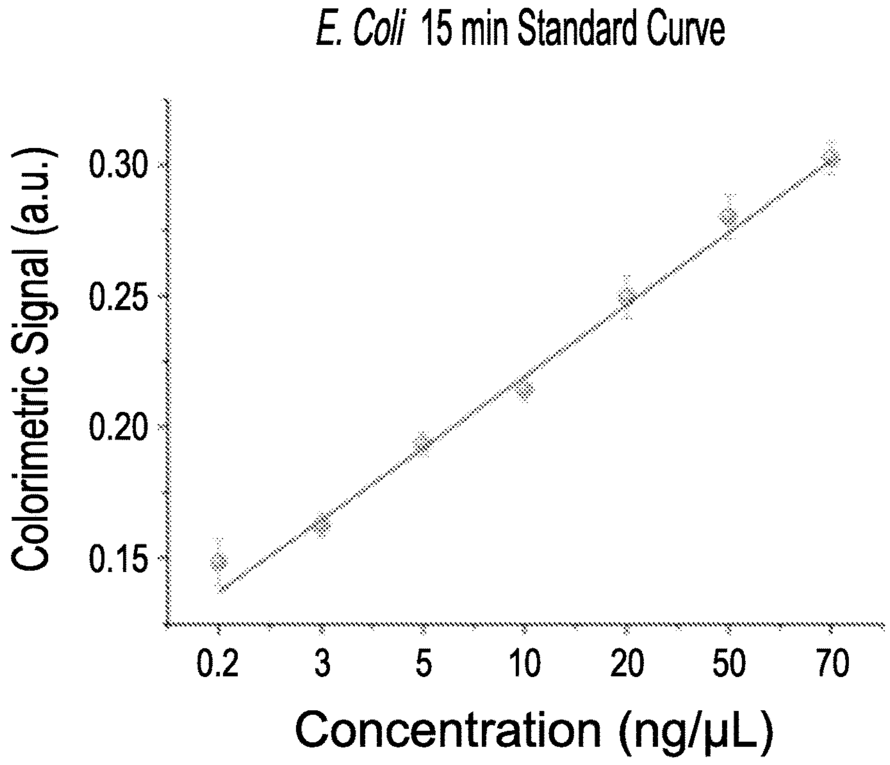
FIG. 14J is a standard curve based on FIG. 14G, the mean data points per concentration were averaged and plotted.
Figure 14K:
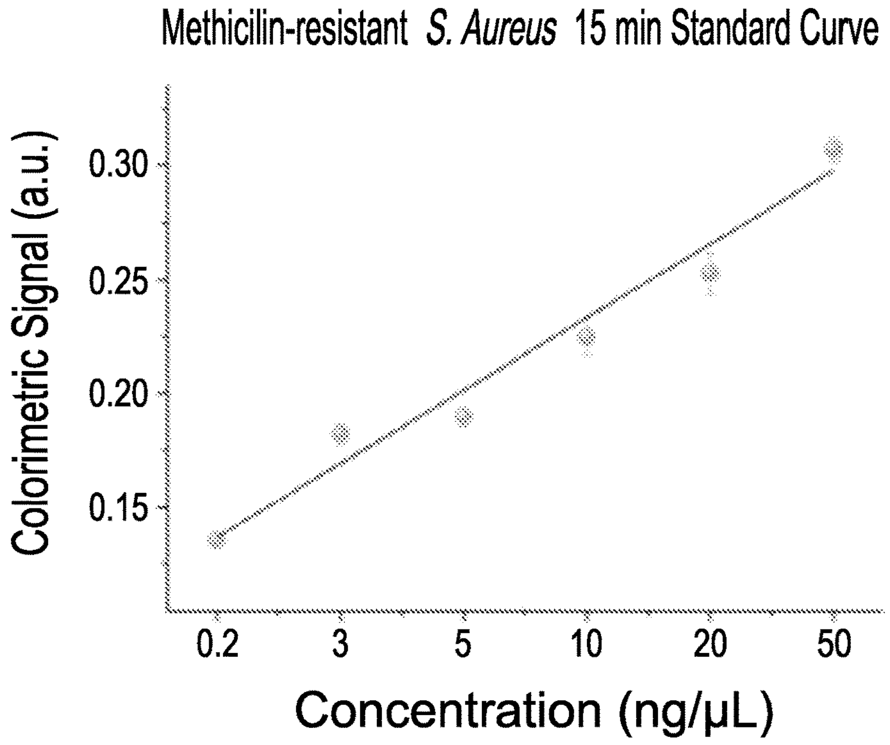
FIG. 14K is a standard curve based on FIG. 14H, the mean data points per concentration were averaged and plotted.
Figure 14L:
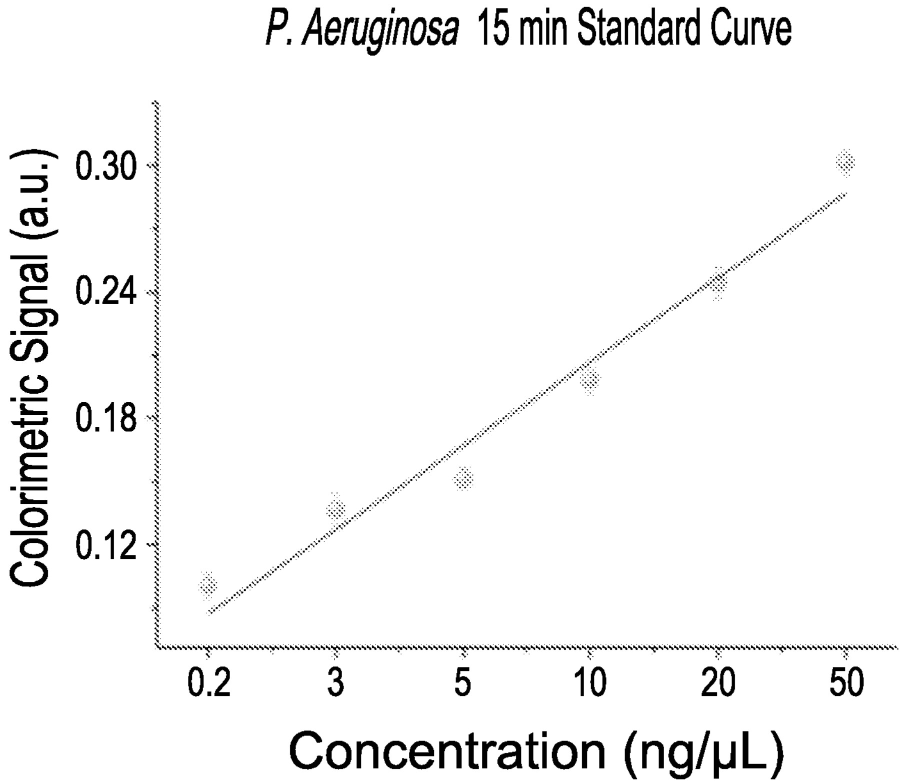
FIG. 14L is a standard curve based on FIG. 14I, the mean data points per concentration were averaged and plotted.

To determine the limit of detection (LOD), the means of the colorimetric signal at 15 min for each tested concentration were compared. FIGS. 14G-141 depict the range of data points for the mean colorimetric signals, indicating a gradual increase in signal for increasing concentrations. The mean data points per concentration was averaged, for each bacterium and plotted a standard curve (FIGS. 14J-14L). The adjusted $R^2$ values were 0.99075, 0.96331, and 0.95655, for *E. coli*, Methicillin-resistant *S. aureus*, and *P. aeruginosa*, respectively. The LOD was calculated using values obtained from the standard curve and was determined to be 1.4 ng/μL for *E. coli*, 2.2 ng/μL for Methicillin-resistant *S. aureus*, and 2.94 ng/μL for *P. aeruginosa*.

Figure 15A:
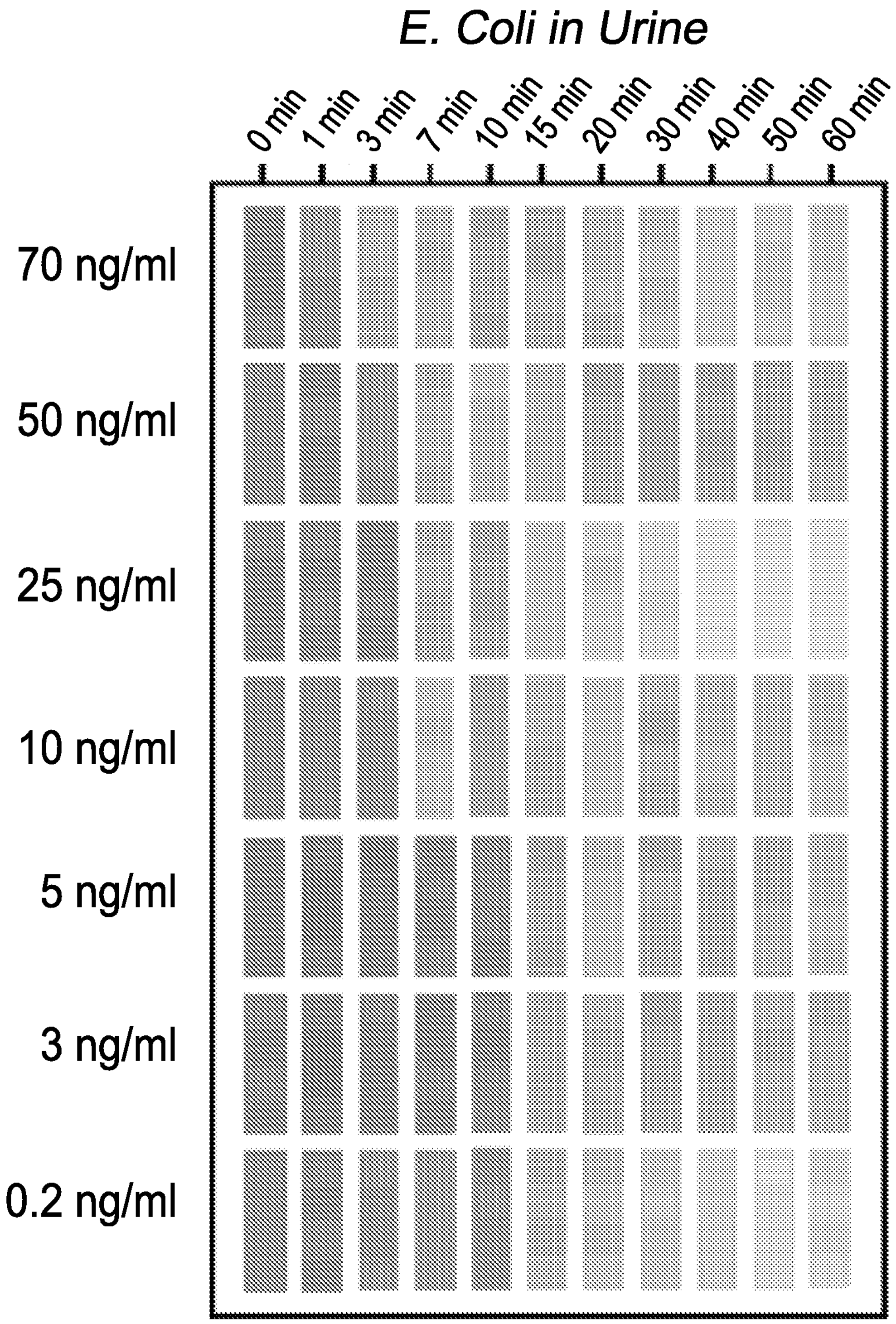
FIG. 15A shows *E. coli* sensitivity results in urine illustrated by a color matrix of on-chip sensitivity test for *E. coli* in urine for 0.2 ng/μL-70 ng/μL.
Figure 15B:
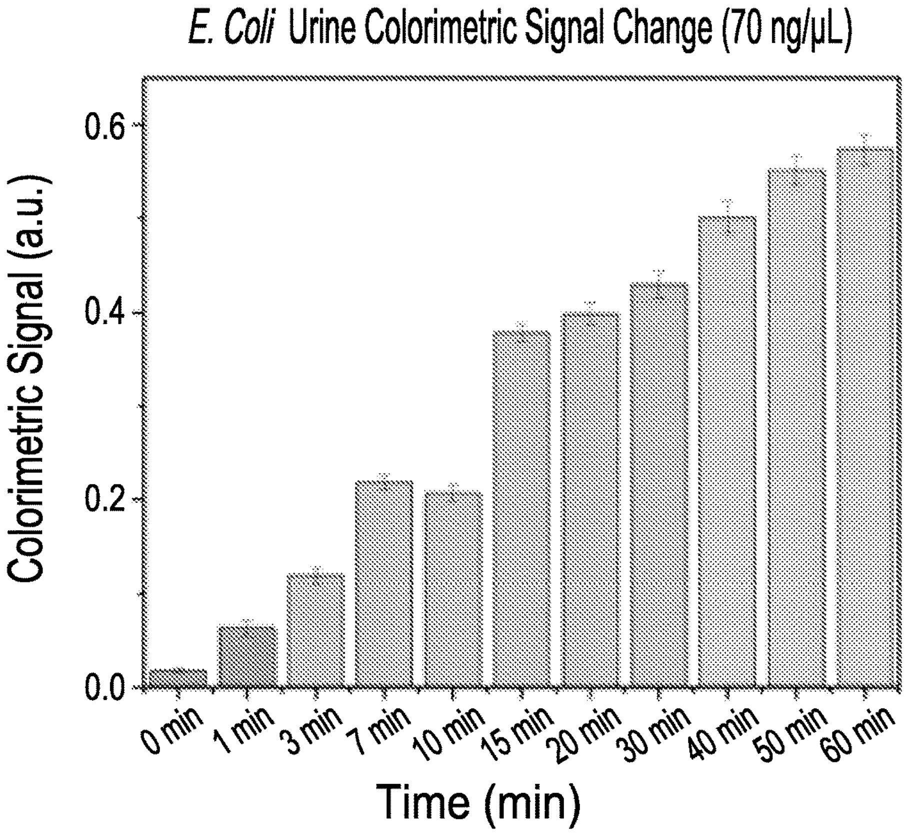
FIG. 15B is a bar graph showing the quantitative colorimetric signal change for 70 ng/μL *E. coli* up to 60 min. Colorimetric signal changed at 3 min, passing 0.1 a.u. signal threshold.
Figure 15C:
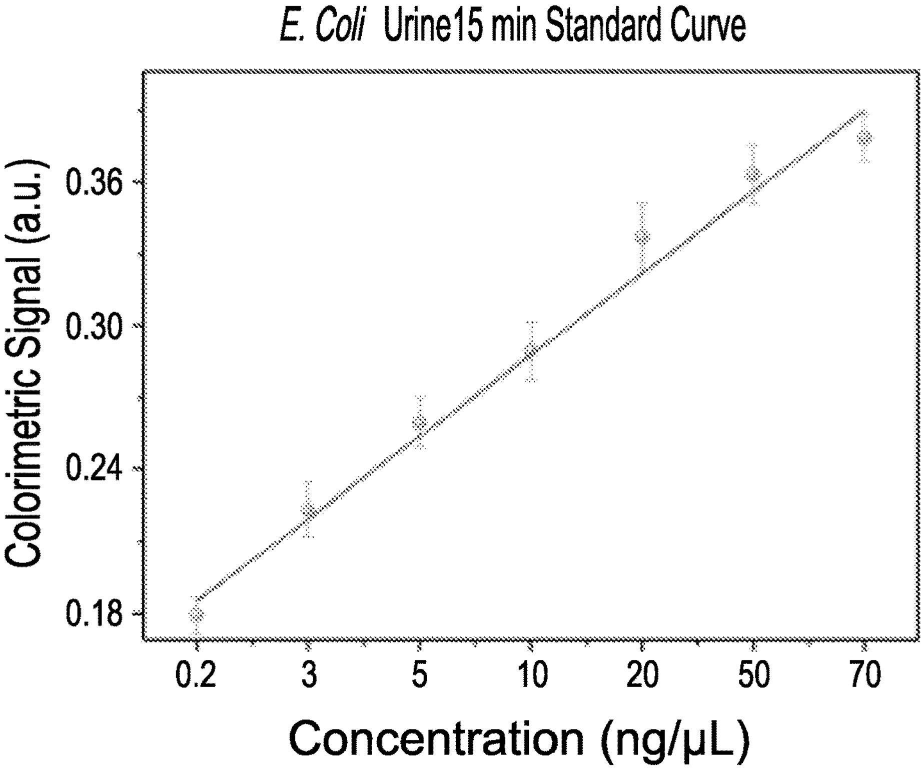
FIG. 15C is the standard curve for colorimetric signal across linear range of 0.2-70 ng/μL *E. coli*, with an adjusted $R^2=0.9868$.

*E. coli* typically presents in urine in the range of 3-50 ng/μL for urinary tract infections (UTI). To simulate real clinical samples of UTI, *E. coli* DNA was spiked in 1 μL of pooled urine. *E. coli* DNA samples were tested in urine across the physiological range with the microfluidic chip 100, 100', 400, 400', 400", with noticeable color changes as early as 3 min for 70 ng/μL (FIG. 15A). The colorimetric signal for 70 ng/μL was plotted, which confirmed the qualitative response from the on-chip microscopy images (FIG. 15B). The standard curve for *E. coli* in urine was plotted as shown in FIG. 15C, with an adjusted $R^2$ value of 0.9868. The standard curve was used to calculate the LOD which worked out to be 1.73 ng/μL, closely matching *E. coli* in buffer results.

Figure 16A:
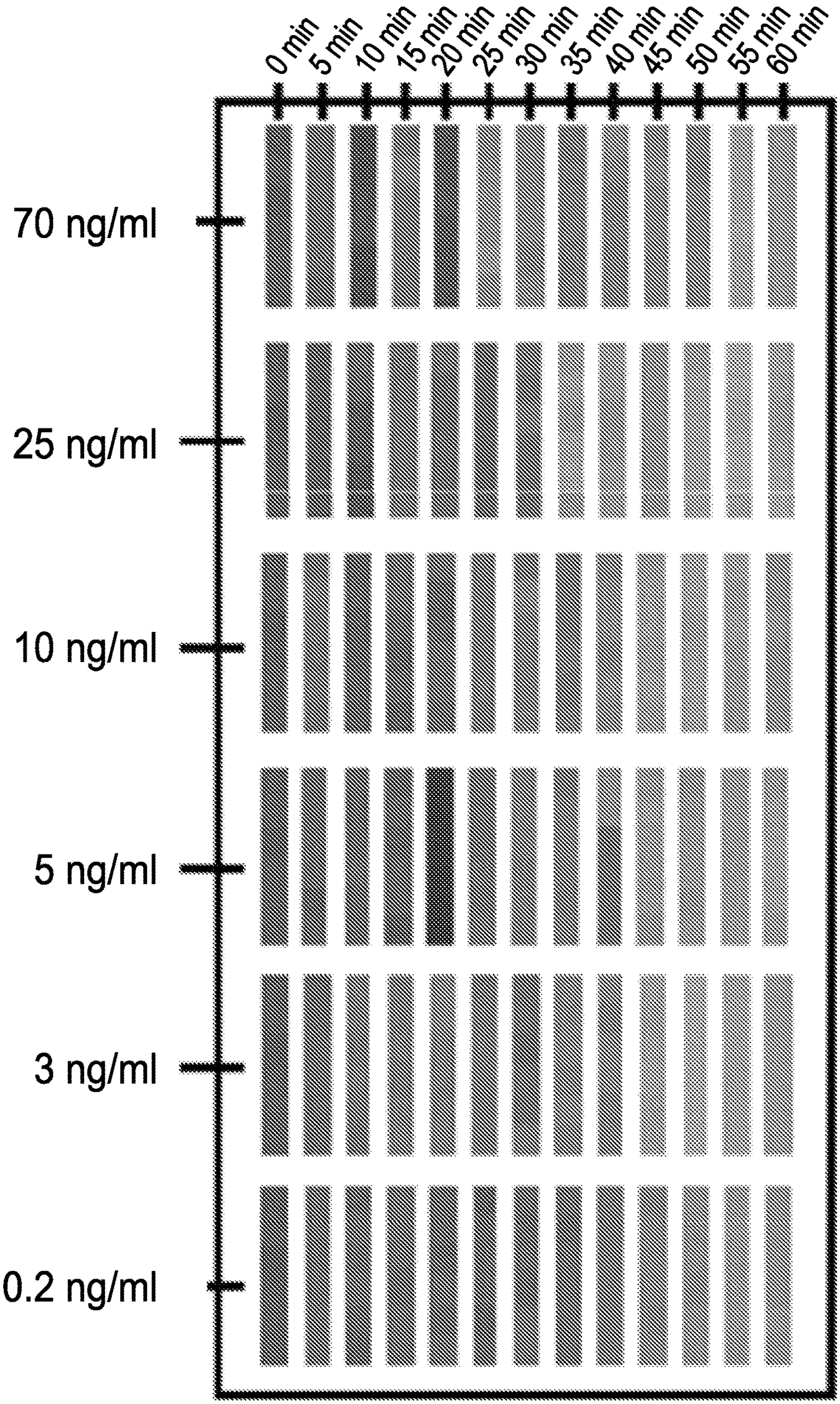
FIG. 16A shows a resazurin diagnosis experiments with different concentrations of *E. coli* DNA illustrated by a color matrix.
Figure 16B:
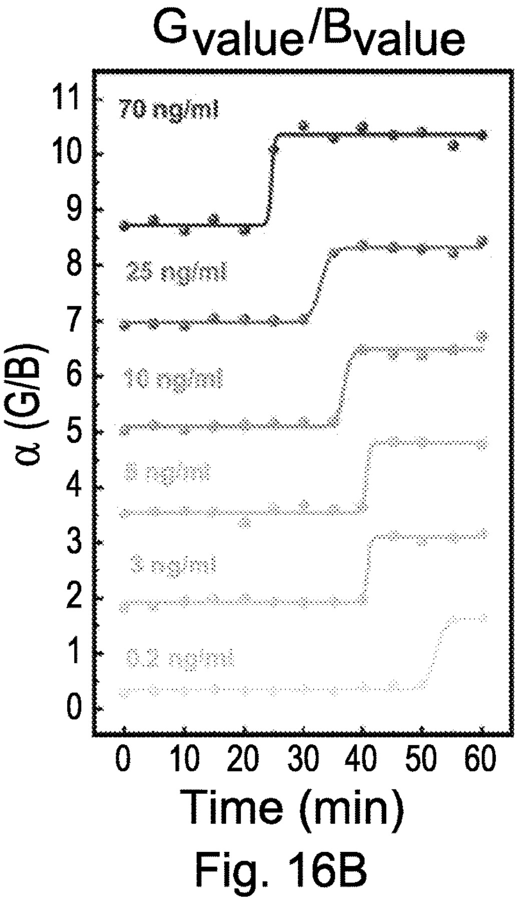
FIG. 16B is a $G_{value}/B_{value}$ curves of the color response from diagnosis experiments on *E. coli* in a Rose-Dip fit.

To test the efficacy of the microfluidic chip 100, 100', 400, 400', 400" in diagnosing bacterial DNA, resazurin was used as a pH indicator in a colorimetric LAMP reaction. Resazurin, as mentioned in Example I changes color from blue to purple at a pH of 6.5, allowing to identify the amplification of DNA which drives the release of $H^+$ ions in the solution. The LAMP reaction consisted of five components: the *E. coli* DNA sample, 10× primer mix, WarmStart™ LAMP 2× Master Mix (NewEngland Biolabs, MA, USA), resazurin, and DNAse-free $H_2O$ (Thermo Fischer Scientific, MA, USA). The standard reaction volume of 25 μl consisted of 2.5 μl 10× primer mix, 12.5 μl WarmStart® LAMP 2× Master Mix, 8 μl DNase-free $H_2O$, 1 μl of resazurin, and 1 μl DNA sample. The LAMP reaction was incubated at a temperature ranging from 60-65° C. and monitored for color changes at different intervals up to 60 min. During the incubation period, we noticed that the color change initiated in 40 min. Following this, we placed 1 μl of the LAMP mixture on the platform for each interval and imaged using a bright-field microscope (FIGS. 16A and 16B). Evidently, the highest DNA concentration tested (70 ng/μl) showed a color change within 25 min, while the lowest concentration (0.2 ng/μl) showed color change at 55 min. This confirmed the effective amplification of the DNA sample, and the ability of the microfluidic chip to enhance sensitivity.

To conclude, the present Example II showed the application of the plasmonic-enhanced microfluidic chip integrating colorimetric LAMP for the ultra-rapid detection of bacterial DNA for visible colour change in 15 min. *E. coli*, Methicillin-resistant *S. aureus*, and *P. aeruginosa* were all detected in the physiological range. Consequently, the specificity of each primer set for the target DNA in cross reactivity was determined in a test against non-target DNA and negative control samples. All primer sets showed 100% specificity for target DNA samples, enabling the differentiation of *E. coli*, Methicillin-resistant *S. aureus*, and *P. aeruginosa*. Sensitivity was measured matching physiological concentrations. Last, the colorimetric response of *E. coli* in urine was evaluated successfully.

Example III

Another exemplary use of the microfluidic chip 100, 100', 400, 400', 400" is using the amplex red color sensor for detection of hydrogen peroxide ($H_2O_2$). $H_2O_2$ is a biomarker employed by liquid biopsies to offer a non-invasive alternative for cancer diagnosis. Liquid biopsies identify the presence and concentrations of specific biomarkers. $H_2O_2$ has been appointed as a cancer biomarker due to its increased release from cancer cells compared to normal cells. Still, a sensitive measurement is needed to allow for the detection of the low concentrations of $H_2O_2$ released from cancer cells. In this example, Amplex Red assay is used as color sensor as it reduces into resorufin in the presence of $H_2O_2$.

For the optimization studies, $H_2O_2$ at 30%, 7.4 pH and sterile Phosphate Buffered Saline (PBS) (0.067 M, 10×) were used. The solutions for different concentrations of $H_2O_2$ were freshly prepared using PBS diluted to 1×. The concentrations ranged from micromolar to picomolar (10 uM, 1 uM, 500 nM, 100 nM, 1 nM, 500 μM, 100 μM and 1 μM).

For the cellular sample experiments, breast cancer cells (MCF-7) and fibroblast (hVFF) were cultured in Dulbecco's Modified Eagle's Medium, supplemented with 10% (v/v) fetal bovine serum (FBS), 100 U $mL^{-1}$ penicillin, and 100 mg $mL^{-1}$ streptomycin. Cystic fibrosis bronchial epithelial cells (CFBE) were cultured in Eagle's Minimum Essential Medium, supplemented with 10% (v/v) fetal bovine serum (FBS) and 1% (v/v) L-Glutamine. Prostate cancer cells (PC3) were culture in Ham's F-12K medium with 10% (v/v) fetal bovine serum (FBS). Once the cells reached ~90% confluence, the cells were collected via trypsin removal followed by centrifugation. Cell numbers were estimated by a hemocytometer and resuspended in 1×PBS (pH 7.4), for measurements $2.5\times10^5$ cells were added into 3 mL of 1:100 human plasma diluted in 1×PBS (pH 7.4). Prior to the measurement, 1000 ng/ml[46] of Phorbol-12-myristate-13-acetate (PMA) was injected to induce the release of $H_2O_2$ into the media, after one minute the media was collected and mixed with amplex red working solution for colorimetric detection.

The colour change was characterized via colour analysis of the bright field microscope images through a 100×, 0.9 NA air objective. Images, in RGB colour space, were captured with a Nikon digital sight ds-fi1 CCD camera with a white reference of R:2.54 G:1.0 B:2.11 and a hue and saturation of +0.5. All RGB images were processed in MATLAB and were cropped to avoid the "coffee-ring effect". Afterwards, the code takes five random samples within the designated area and averages the RGB value of them. Subsequently, a transformation of the original RGB values into X, Y, and Z values of the CIE 1931 color space was performed. Herein a color stimulus is transformed into the XYZ tristimulus to describe it in terms of a visual system while taking into consideration the illumination source. At last, the XYZ were converted to x,y values (as described in Example 1), coordinates of the chromaticity plot.

Briefly, the sample containing $H_2O_2$ was mixed with the amplex red working solution and visualized on top of the enhancer plasmonic platform through a bright-field microscope equipped with a colour camera. The images captured provide a colorimetric readout which was processed and analyzed in two colour spaces (RGB and CIE 1931) to confirm the presence of $H_2O_2$.

Figure 17A:
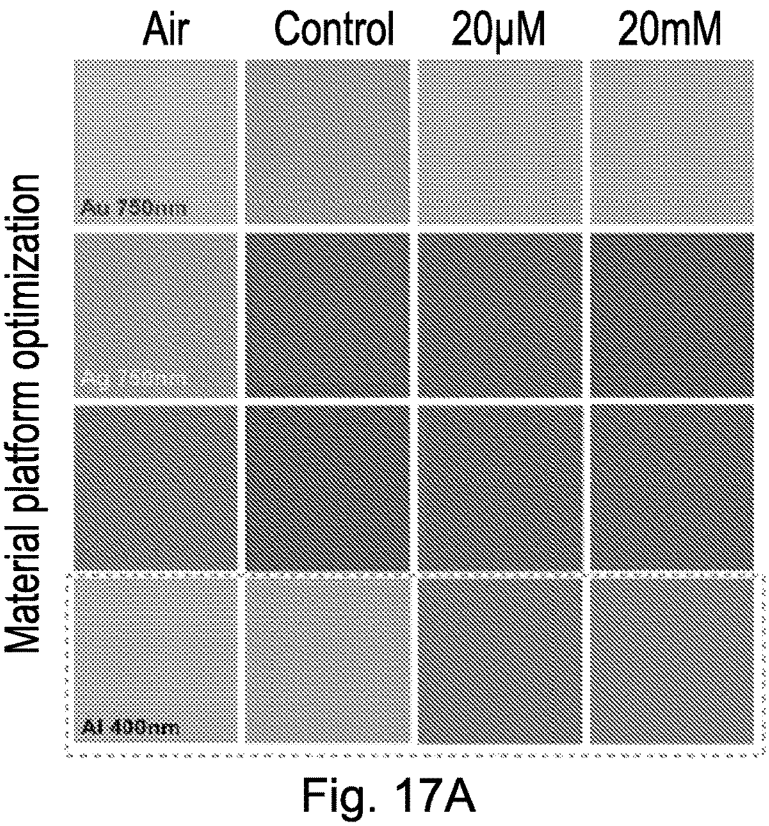
FIG. 17A is a colour matrix of 750 nm patterned platform coated with the three plasmonic materials (Au, Ag and Al) and 400 nm Al in different media (air, control 20 μM and 20 mM $H_2O_2$ in PBS (pH=7.2) solution).
Figure 17B:
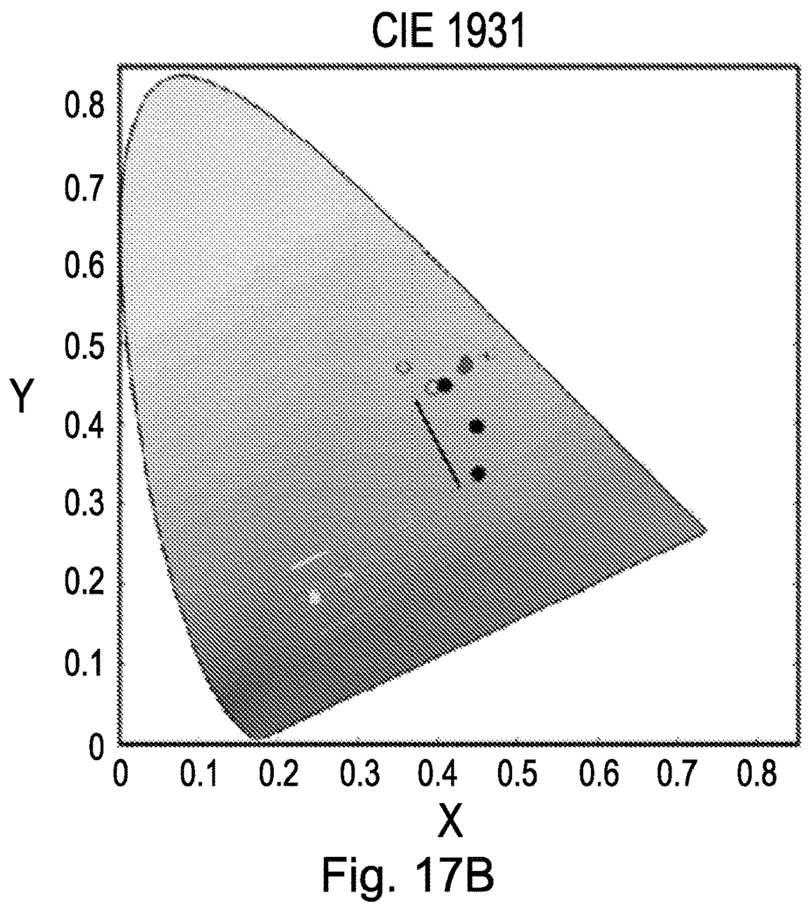
FIG. 17B is a 1931 CIE plot of the gamut of each platform presented in FIG. 17A.
Figure 17C:
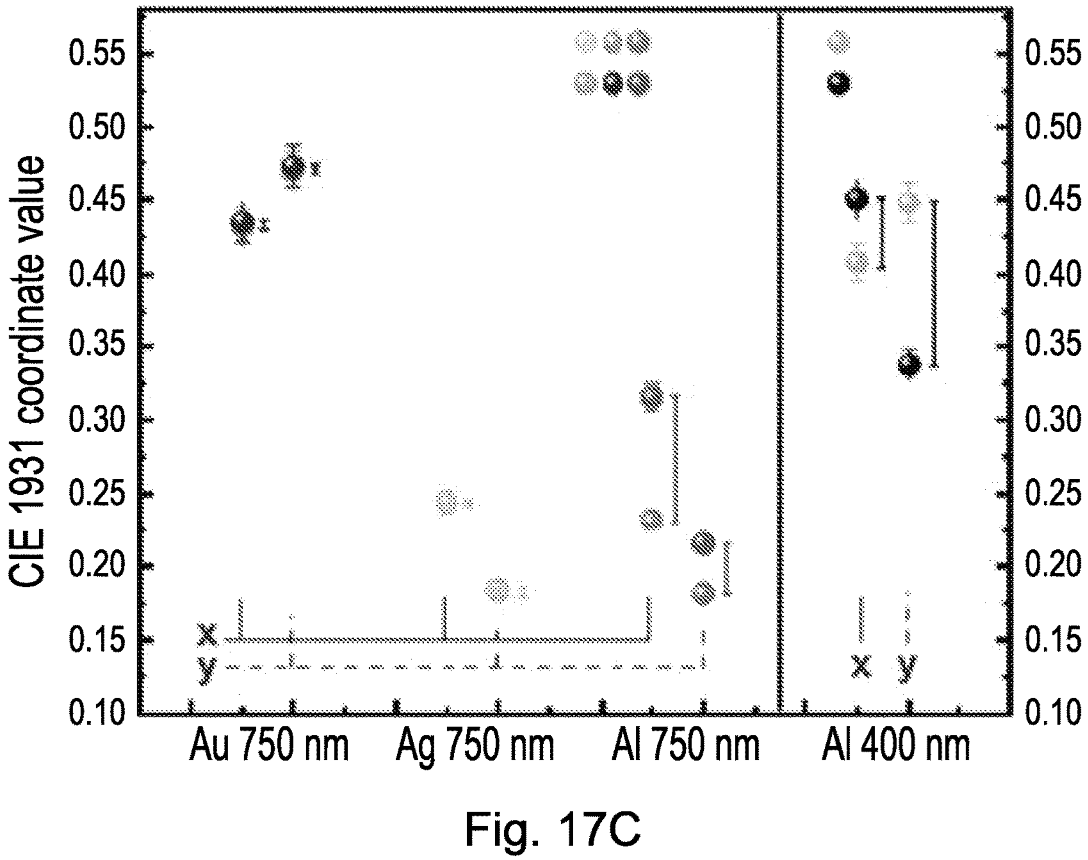
FIG. 17C is a dot plot of the difference in x and y coordinate values for the 1931 CIE plot from FIG. 17B between the Control and the 20 mM in $H_2O_2$ PBS (pH=7.2) solution.

The colour response varied between materials suited for plasmonic applications, thus, gold (Au), silver (Ag) and aluminum (Al) were studied. The materials response was assessed by the colour generated by platforms patterned with 750 nm PS-nanoparticles and deposited with an ultrathin layer of the various materials (Au, Ag, or Al). The metallic-deposited platforms were observed in the presence of four media (air, amplex red working solution (control) and amplex red in presence of 20 μM and 20 mM $H_2O_2$ in PBS (pH 7.2)). The results are presented in the colour matrix in FIG. 17A and the CIE 1931 chromaticity plot (FIG. 17B), a more in-depth analysis of the colour was achieved by studying the CIE 1931 coordinates (FIG. 17C). Among the plasmonic materials, the gold response showed no drastic color difference was observed across the media (blue labels in FIGS. 17A-17C). Silver, despite having a pronounced color change from the air to the solutions (green labels in FIGS. 17A-17C), between these last, the color change was not as noticeable as it was observed for the aluminum (red labels in FIGS. 17A-17C). Aluminum showed a difference between these media; hence, the material was selected, and further optimization was performed. The plasmonic colour properties, such as hue and gamut, can be modified by the geometry and size of the pattern. Thus, a 400 nm PS-nanoparticles patterned platform was investigated following the same conditions to assess the possibility of widening the gamut offered by the platform in response to the surrounding media. The 400 nm Al platform presented a wider gamut, showing clear distinctions between the colours for the $H_2O_2$ concentrations and the control media (black label in FIGS. 17A-17C). The qualitative colour gamut observed across the different platforms was generated by the plasmonic enhancer platform as a sensitive colour response to the medium's refractive index changes. Furthermore, the alterations of the refractive index of the medium were attributed to the change in the analyte concentration.

Figure 18A:
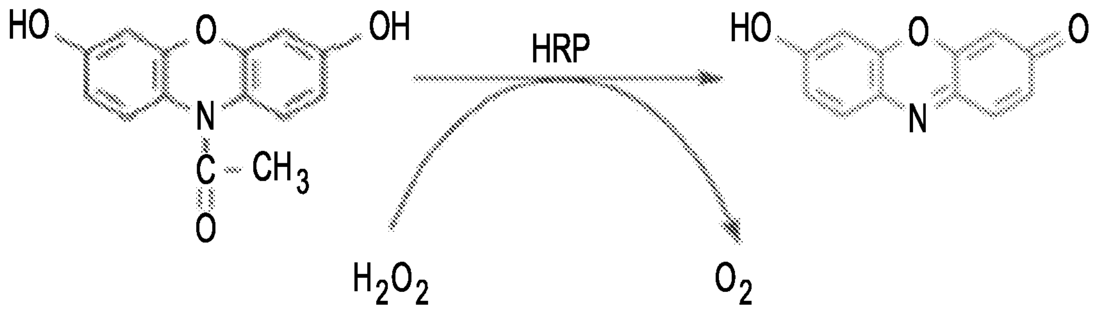
FIG. 18A shows the reaction of Amplex™ Red colour turning into resorufin.
Figure 18B:
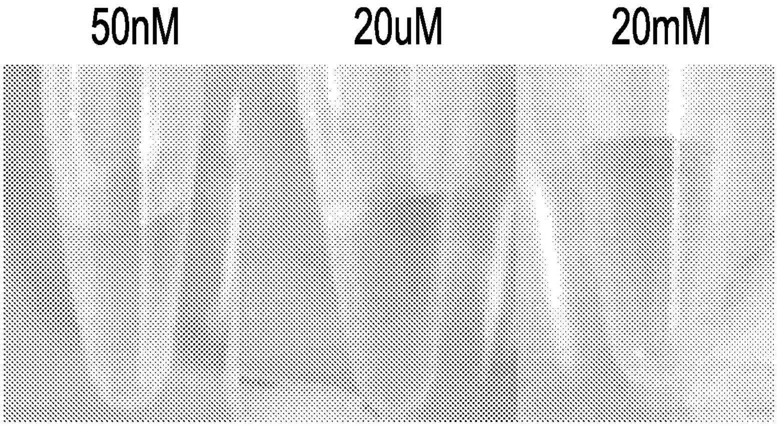
FIG. 18B is a photograph of Eppendorf tubes showing the colour observed at concentrations of 50 nM, 20 μM, and 20 mM resorufin.
Figure 18C:
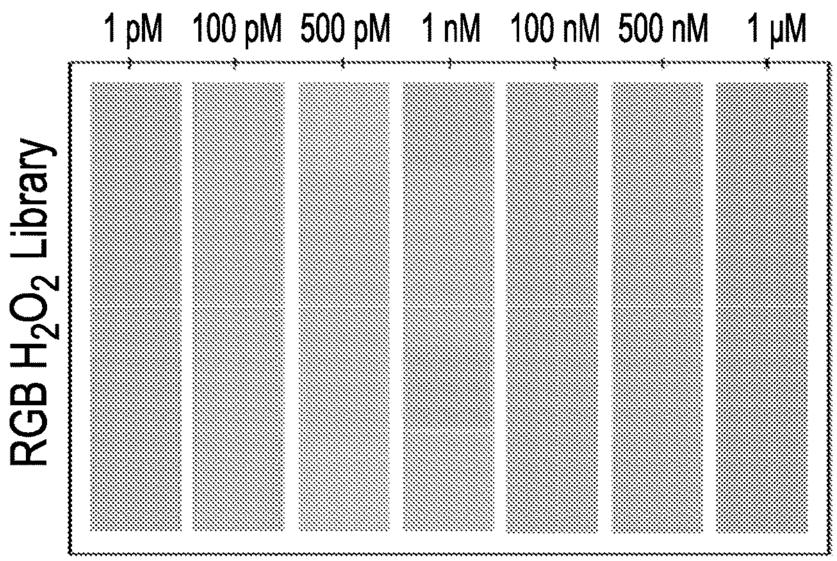
FIG. 18C is a RGB colour library of Amplex™Red in presence of $H_2O_2$.

Amplex red reagent is a colourless substrate, that in presence of an enzyme (horse radish peroxidase (HRP)), reacts with ($H_2O_2$) with a 1:1 stoichiometry to produce highly fluorescent pink resorufin, providing a colorimetric indicator. Detection of $H_2O_2$ is based on peroxidase-catalyzed oxidation of amplex red to resorufin (FIG. 18A). As a common colorimetric assay, the chromogenic indicator colour change was dependent on the concentration of the analyte. An extended range and sensitivity have been reported when compared to classic colorimetric oxidase assays. However, as observed in FIG. 18B, to the naked eye there is a limit of the colour change that can be distinguished while LOD of amplex red assay fluorescence has been reported to be 50 nM, the naked-eye response becomes indistinguishable at ~5 μM, a concentration at which the solution appears colourless to the observer. When the reaction takes place on top of the plasmonic nanosurface 105*p*, 105*p*' (FIG. 18C) the plasmonic free electrons oscillation enhances the colour change, produced by the media permittivity variation. The colour change was registered through a series of images capture through a set-up including bright-field microscopy and a colour camera. An RGB colour library, as observed in FIG. 18C was built with $H_2O_2$ concentrations ranging from 1 μM to 1 μM in a biocompatible PBS (pH=7.2) medium, rendering a colour gamut from lilac towards orange as the analyte concentration increases caused by a decrease in the R channel.

Figure 18D:
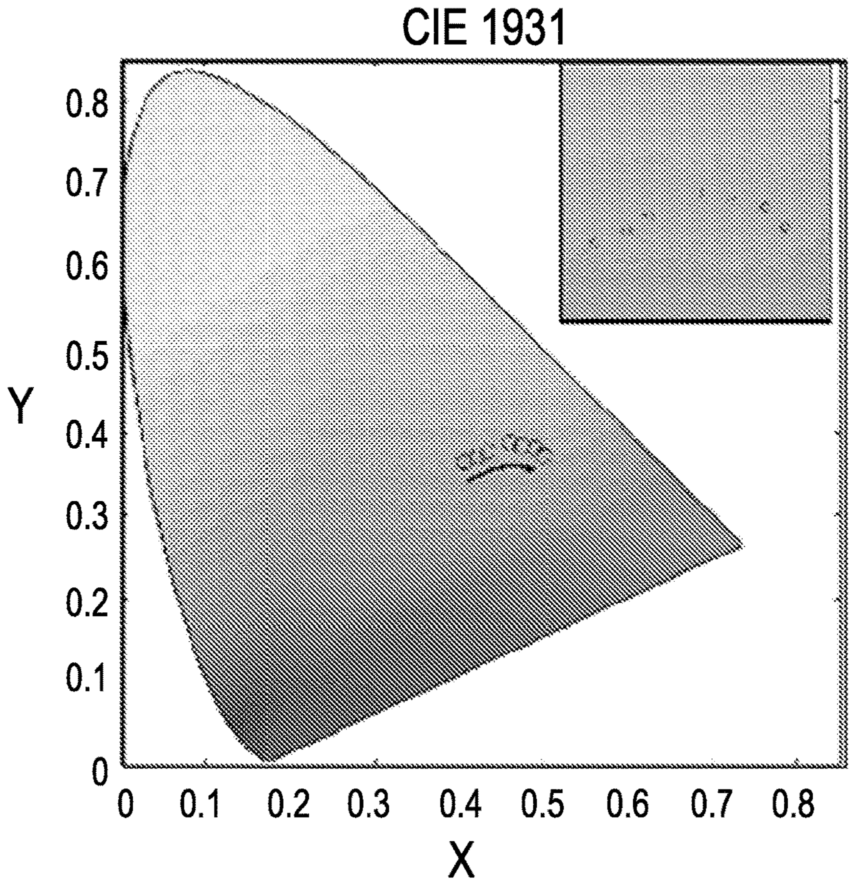
FIG. 18D is an Amplex™Red-$H_2O_2$ colour library in CIE 1931 colour space.
Figure 18E:
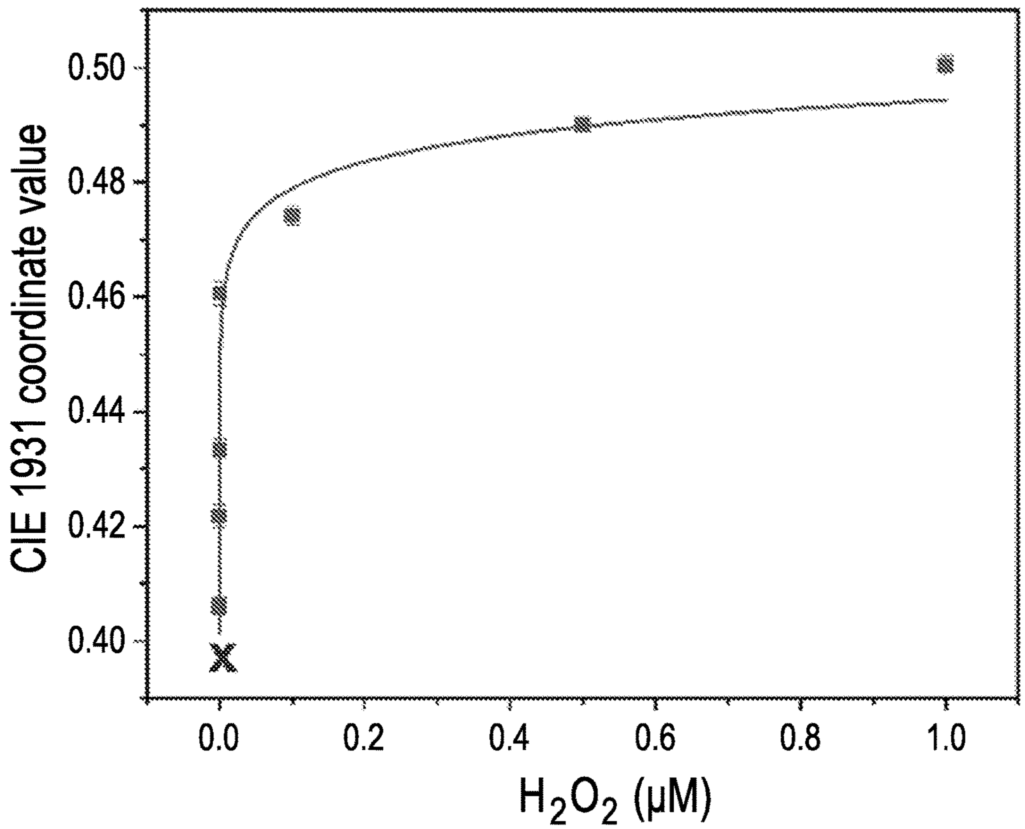
FIG. 18E is a plot of the $H_2O_2$ concentration versus the x value of CIE 1931 colour space.
Figure 18F:
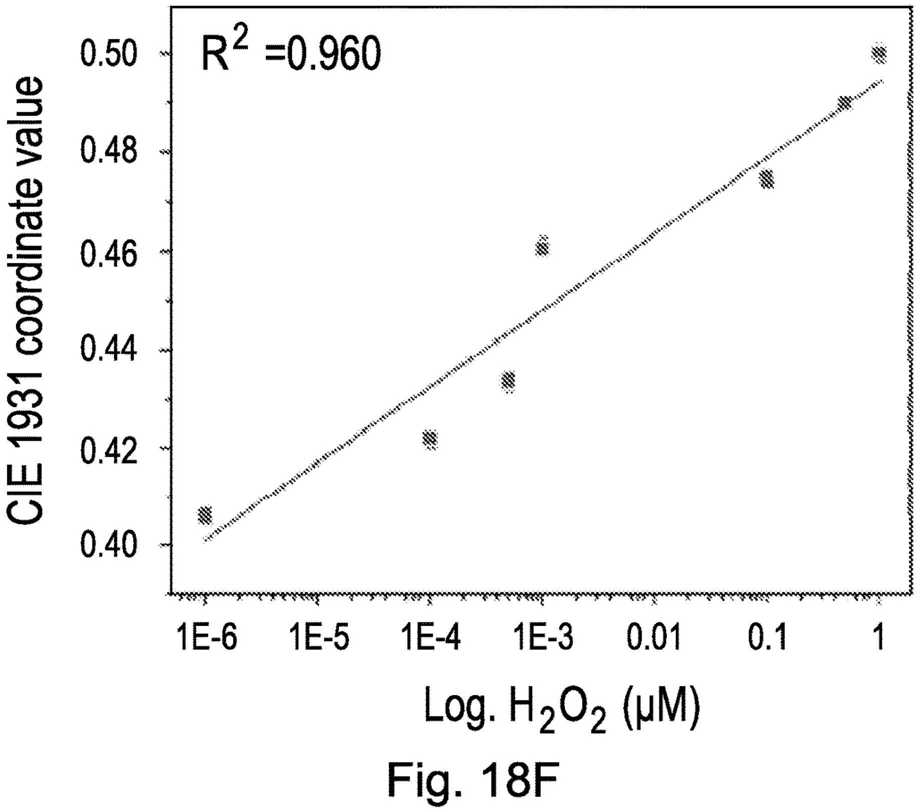
FIG. 18F is a plot showing the linear regression analysis of the plot of FIG. 18E with $R^2=0.960$.

To facilitate image analysis, the microscopy images were translated into numerical values through a MATLAB code. The code reads in RGB colour space, then they were transformed into a CIE 1931 colour space, for interpretation through chromaticity plot. The gamut shown in FIG. 18D confirmed a trend, gradually changing its x coordinate value, as shown by the black arrow. To independently analyze the x coordinate, the scattered plot in FIG. 18E was generated. The behaviour of the colour assay correlated to the exponential variation of the tested $H_2O_2$ concentrations. The enhanced colour readout allowed a limit of detection of 1 μM, furthermore, a linear regression analysis was performed, the data presented a linear fit ($y=m \cdot x+b$) with a $R^2=0.960$ value. The enhanced colour readout allowed a limit of detection of 1 μM, Here, the linear fit describes the concentration of $H_2O_2$ detected by the reduction of the amplex red assay.

Figure 19A:
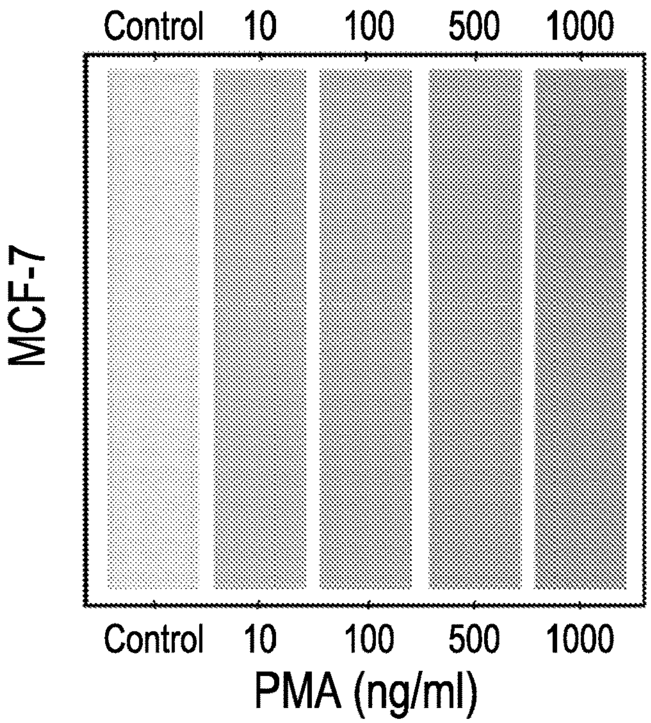
FIG. 19A shows RGB colours of MCF-7 cancer cell resuspended in a biocompatible pH media (PBS (pH 7.2)) exposed to different concentrations of PMA and control, where no PMA was added.
Figure 19B:
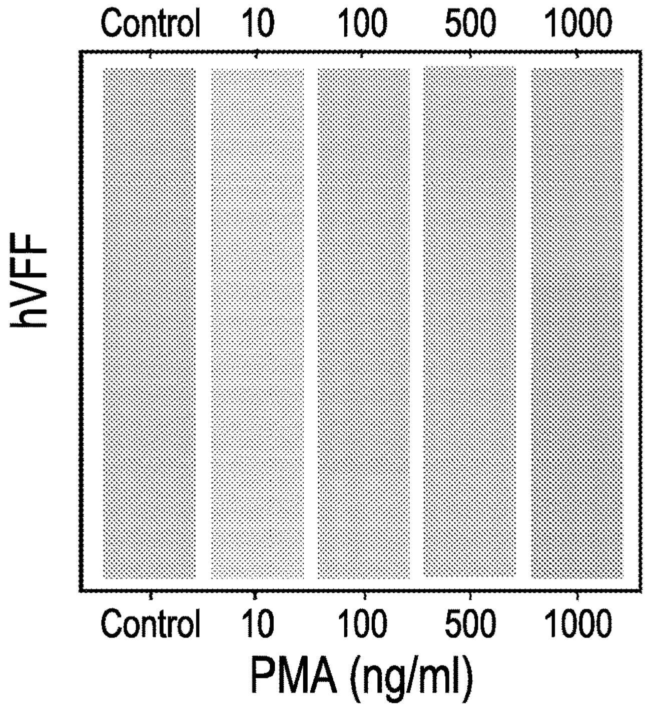
FIG. 19B shows RGB colours of hVFF non-cancer cells resuspended in a biocompatible pH media (PBS (pH 7.2)) exposed to different concentrations of PMA and control, where no PMA was added.

After successful detection of amplex red assay in the biocompatible PBS (pH=7.2) medium, an experiment for direct detection of $H_2O_2$ released from human cells was performed as seen in FIGS. 19A-19B. Cells were first studied in a biocompatible environment (PBS (pH=7.2). In order to stimulate the release of $H_2O_2$ from the cells, a concentration of PMA needed to be added prior to measurement.

Figure 19C:
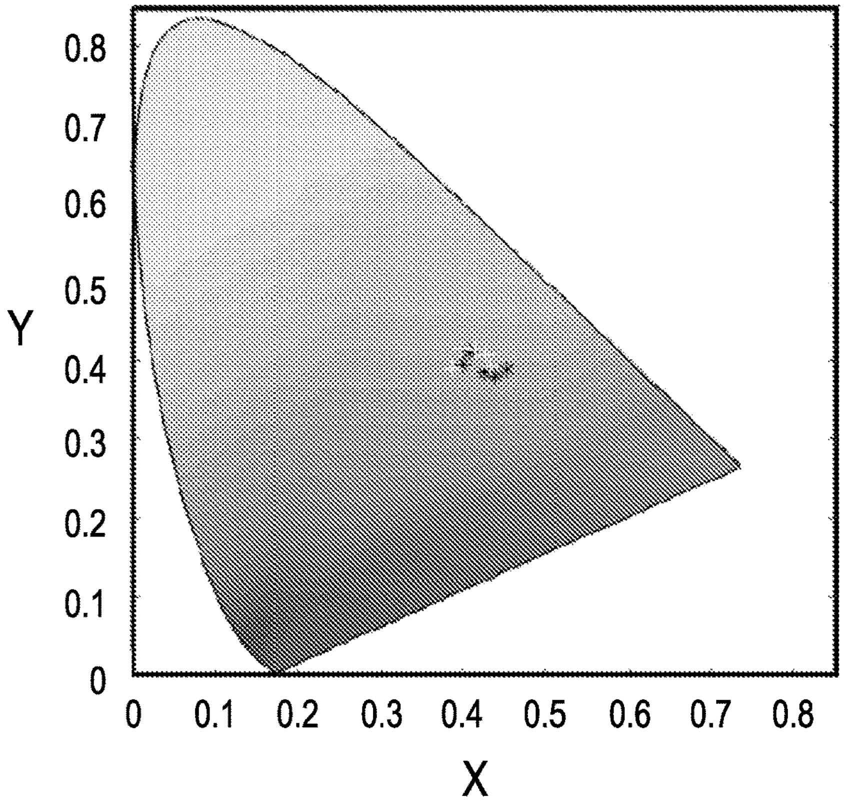
FIG. 19C is a CIE 1931 plot for both MCF-7 and hVFF(+) (FIGS. 19A-19B).
Figure 19D:
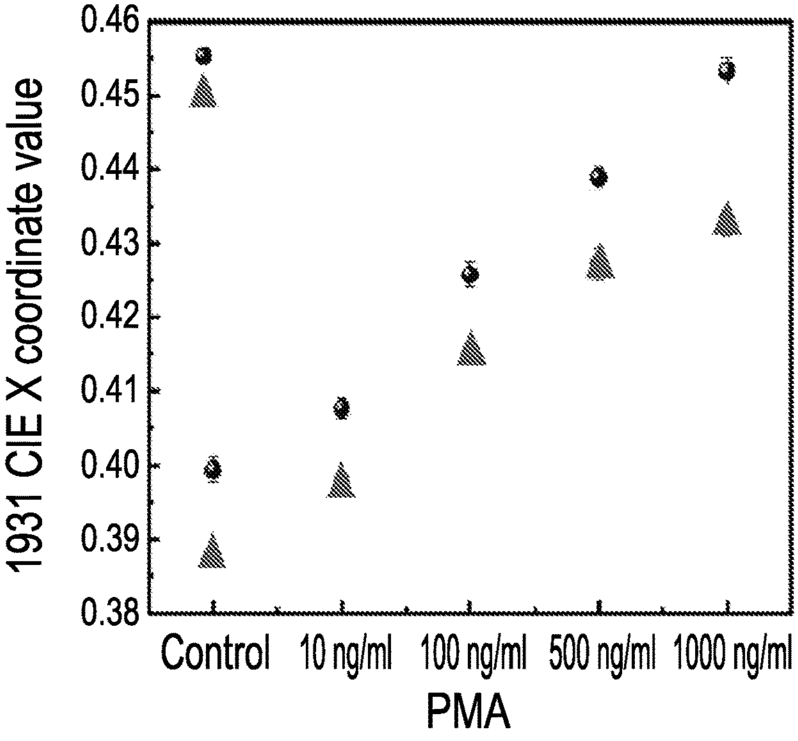
FIG. 19D is a dot-plot of x coordinate values of CIE plot comparing both types of cells (MCF-7 and hVFF(+)).
Figure 19E:
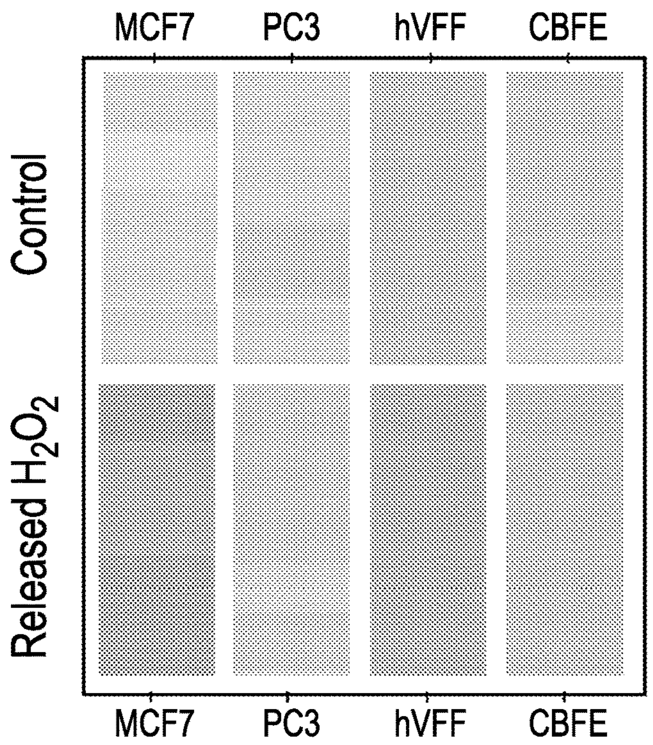
FIG. 19E shows RGB values of 4 different cell lines: 2 cancer cells (MCF-7 and PC3) and 2 non-cancer cells (hVFF and CBFE) both in control state and after a 1000 ng/ml injection of PMA to stimulate the release of $H_2O_2$. Cells were resuspended in 1:100 Plasma-PBS dilution.
Figure 19F:
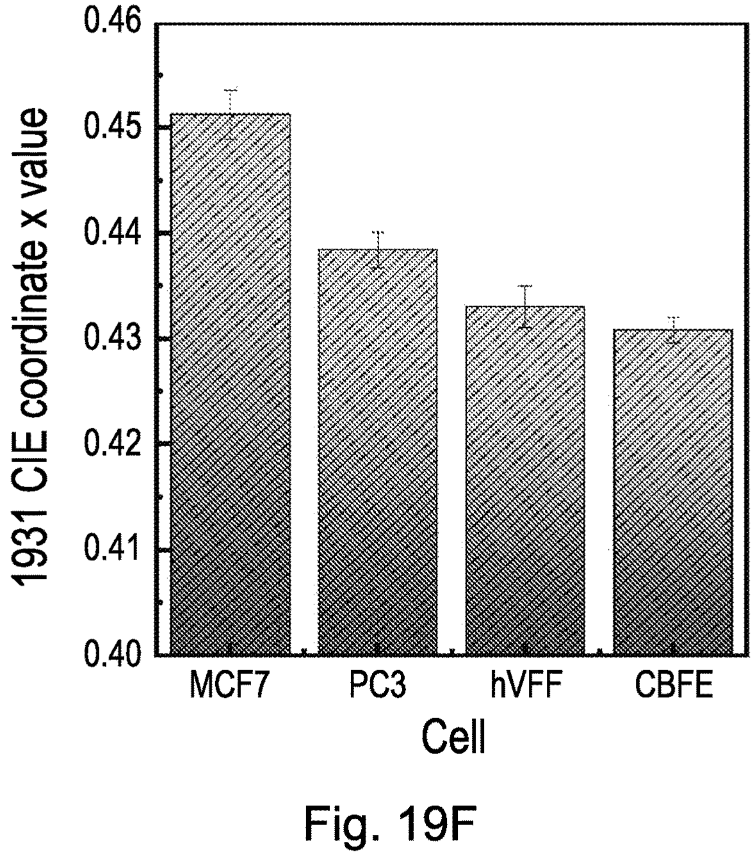
FIG. 19F is bar graph showing the value of the CIE 1931 x coordinate shown by the cells of FIG. 19E after the release of $H_2O_2$.

The microfluidic chip effectively changed the color of the sample in the presence of the analyte, as seen in the control samples presenting a light colour with a low value of x coordinate in the CIE 1931 colour space (FIG. 19C) while the cells media present a browner colour (FIGS. 19A-19D)) due to the increment of the R-value, also seen as an increase of the x coordinate value in FIGS. 19C-19D. As the reading of the sensor was successful for the PBS environment, 4 cell lines were tested in a 1:100 human plasma solution to simulate real conditions (FIGS. 19E-19F). The cell lines were 2 cancer cells: breast and prostate cancer (MCF-7 and PC3, respectively) and 2 non-cancer cells fibroblast and epithelial (hVFF and CBFE, respectively). FIG. 19E presents the RGB values collected from the bright-field microscopy and processed through the MATLAB code. Showing an evident difference between the control colour and the colour achieved once the cells were stimulated to release their $H_2O_2$ into the media for all the cell lines, the MCF-7 cancer cell showed a drastic change. In FIG. 19F a bar plot shows the x coordinate values of released $H_2O_2$ from FIG. 19E. As observed in FIG. 19E the values are bigger for both cancer cells.

To conclude the present Example III, different concentrations of $H_2O_2$ via amplex red colorimetric assay were evaluated in a buffer solution, from which a calibration curve was constructed. Consequently, the detection of $H_2O_2$ released from stimulated cells resuspended in human plasma was studied. MCF-7 and PC3 were the cancerous samples, while HvFF and CBFE healthy cell lines were used as a control. The results showed an increased production of $H_2O_2$ derived from the cancer group, as compared to the control groups.

While the present disclosure has been described in connection with specific embodiments thereof, it will be understood that it is capable of further modifications and this application is intended to cover any variations, uses, or adaptations, including such departures from the present disclosure as come within known or customary practice within the art and as may be applied to the essential features hereinbefore set forth, and as follows in the scope of the appended claims.

What is claimed is:

1. A microfluidic chip for sensing an analyte in a sample by colorimetry, the microfluidic chip comprising:

an inlet adapted to receive the sample, an incubation chamber having an incubation chamber inlet fluidly connected to the inlet downstream thereof, to incubate the analyte in the sample;

a filter barrier fluidly connected to the incubation chamber, downstream of the incubation chamber inlet;

a sensing chamber fluidly connected to the incubation chamber, downstream of the filter barrier, the sensing chamber having a plasmonic nanosurface, the plasmonic nanosurface including nanostructures protruding from the plasmonic nanosurface, the nanostructures having a size that is smaller than that of the diffraction limit of light, the nanostructures having a metallic layer that is plasmon-supported on top of a back reflector layer; and an outlet fluidly connected to the sensing chamber downstream thereof.

2. The microfluidic chip of claim 1, wherein the nanostructures have a diameter between 200 nm and 1000 nm.

3. The microfluidic chip of claim 1, wherein nanocavities are defined in between the nanostructures, the nanocavities define an interparticle gap of between 20 nm and 500 nm between the nanostructures.

4. The microfluidic chip of claim 1, wherein the plasmonic nanosurface is free of color pigments.

5. The microfluidic chip of claim 1, wherein the filter barrier comprises at least two rows of micropillars.

6. The microfluidic chip of claim 1, wherein the filter barrier is enclosed in the incubation chamber and occupies a portion of a total volume thereof.

7. The microfluidic chip of claim 1, wherein the nanostructures comprise a monolayer of polystyrene nanoparticles coated by the back reflector layer and further coated by the metallic layer.

8. The microfluidic chip of claim 1, wherein the microfluidic chip further comprises a heating element.

9. The microfluidic chip of claim 1, wherein the back reflector layer is selected from the group consisting of ZnO, $TiO_2$, hydrogen silsesquioxane (HSQ), AZ MiR™, and polymethyl methacrylate (PMMA).

10. The microfluidic chip of claim 1, wherein the metallic surface comprises at least one of Al, Ag and Au.

11. The microfluidic chip of claim 7, wherein the polystyrene nanoparticles have a diameter of between 200 nm to 1000 nm.

12. The microfluidic chip of claim 1, wherein the back reflector has a thickness of 10 to 500 nm.

13. The microfluidic chip of claim 1, wherein the metallic surface has a thickness of 5 to 100 nm.

14. The microfluidic chip of claim 1, wherein the inlet, the incubation chamber, the sensing chamber and the outlet are defined in a layer of negative photoresist forming part of the microfluidic chip.

15. The microfluidic chip of claim 1, wherein the microfluidic chip includes a silicon base layer, an epoxy-based negative photoresist layer onto the silicon base layer, and a curable transparent polymer layer, the incubation chamber and the sensing chamber defined in the epoxy-based negative photoresist layer.

16. A method of sensing an analyte in a sample comprising:

providing a microfluidic chip as defined in claim 1;

providing the sample at the inlet;

incubating the sample in the incubation chamber for a predetermined period of time;

flowing the sample across the filter barrier to the sensing chamber; and analyzing a plasmonic color change of the sample.

17. The method according to claim 16, wherein further comprising providing a colorimetric sensor at a second inlet of the microfluidic chip.

18. The method according to claim 17, further comprising mixing the colorimetric sensor and the sample in microchannels of the microfluidic device.

19. The method according to claim 16, further comprising, before providing the sample at the inlet, mixing the sample with a colorimetric sensor.

20. The method according to claim 16, wherein the incubating of the sample in the incubation chamber comprises heating the microfluidic chip to induce a nucleic acid amplification of the analyte being a nucleic acid sequence.

* * * * *